(12) United States Patent
Shelton, IV et al.

(10) Patent No.: US 9,687,232 B2
(45) Date of Patent: Jun. 27, 2017

(54) SURGICAL STAPLES

(71) Applicant: Ethicon Endo-Surgery, Inc., Cincinnati, OH (US)

(72) Inventors: Frederick E. Shelton, IV, Hillsboro, OH (US); Chester O. Baxter, III, Loveland, OH (US); Jerome R. Morgan, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 344 days.

(21) Appl. No.: 14/138,489

(22) Filed: Dec. 23, 2013

(65) Prior Publication Data
US 2015/0173751 A1 Jun. 25, 2015

(51) Int. Cl.
| A61B 17/08 | (2006.01) |
| A61B 17/064 | (2006.01) |
| A61B 17/072 | (2006.01) |
| A61B 17/068 | (2006.01) |
| A61B 17/00 | (2006.01) |

(52) U.S. Cl.
CPC ........ *A61B 17/0644* (2013.01); *A61B 17/068* (2013.01); *A61B 17/07207* (2013.01); *A61B 17/064* (2013.01); *A61B 17/0682* (2013.01); *A61B 17/072* (2013.01); *A61B 2017/00398* (2013.01); *A61B 2017/00526* (2013.01); *A61B 2017/00734* (2013.01); *A61B 2017/07228* (2013.01); *A61B 2017/07271* (2013.01); *A61B 2017/07278* (2013.01); *A61B 2017/07285* (2013.01); *Y10T 29/49995* (2015.01)

(58) Field of Classification Search
CPC . A61B 17/064; A61B 17/0644; A61B 17/068; A61B 17/0682; A61B 17/072; A61B 17/07207; A61B 2017/07228; A61B 2017/07278
See application file for complete search history.

(56) References Cited

U.S. PATENT DOCUMENTS

| 5,366,479 | A | * | 11/1994 | McGarry | .......... A61B 17/0684 227/902 |
| 7,845,537 | B2 | | 12/2010 | Shelton, IV et al. | |
| 7,980,443 | B2 | | 7/2011 | Scheib et al. | |
| 8,317,070 | B2 | | 11/2012 | Hueil et al. | |
| 8,561,870 | B2 | | 10/2013 | Baxter, III et al. | |
| 2008/0082126 | A1 | * | 4/2008 | Murray | .............. A61B 17/0644 606/221 |
| 2012/0074198 | A1 | | 3/2012 | Huitema et al. | |
| 2012/0080336 | A1 | | 4/2012 | Shelton, IV et al. | |
| 2012/0080344 | A1 | | 4/2012 | Shelton, IV | |
| 2012/0080498 | A1 | | 4/2012 | Shelton, IV et al. | |
| 2012/0298719 | A1 | | 11/2012 | Shelton, IV et al. | |

OTHER PUBLICATIONS

U.S. Appl. No. 14/138,554, filed Dec. 23, 2013.
U.S. Appl. No. 14/138,465, filed Dec. 23, 2013.
(Continued)

*Primary Examiner* — Robert Lynch

(57) ABSTRACT

A surgical staple. The staple can define a seamless unitary piece. In various instances, the staple can be formed and/or stamped from a sheet of material. The staple can include a base and staple legs. A staple drive surface can be integrally formed in the base, and a sled can directly contact the staple drive surface to directly drive the staple.

22 Claims, 55 Drawing Sheets

(56) References Cited

OTHER PUBLICATIONS

U.S. Appl. No. 14/138,485, filed Dec. 23, 2013.
U.S. Appl. No. 14/138,475, filed Dec. 23, 2013.
U.S. Appl. No. 14/138,481, filed Dec. 23, 2013.
U.S. Appl. No. 29/477,488, filed Dec. 23, 2013.
U.S. Appl. No. 14/138,518, filed Dec. 23, 2013.
U.S. Appl. No. 14/138,530, filed Dec. 23, 2013.
U.S. Appl. No. 14/138,507, filed Dec. 23, 2013.
U.S. Appl. No. 14/138,497, filed Dec. 23, 2013.
U.S. Appl. No. 14/138,516, filed Dec. 23, 2013.
U.S. Appl. No. 14/138,474, filed Dec. 23, 2013.
U.S. Appl. No. 14/138,505, filed Dec. 23, 2013.
U.S. Appl. No. 13/851,676, filed Mar. 27, 2013.

* cited by examiner

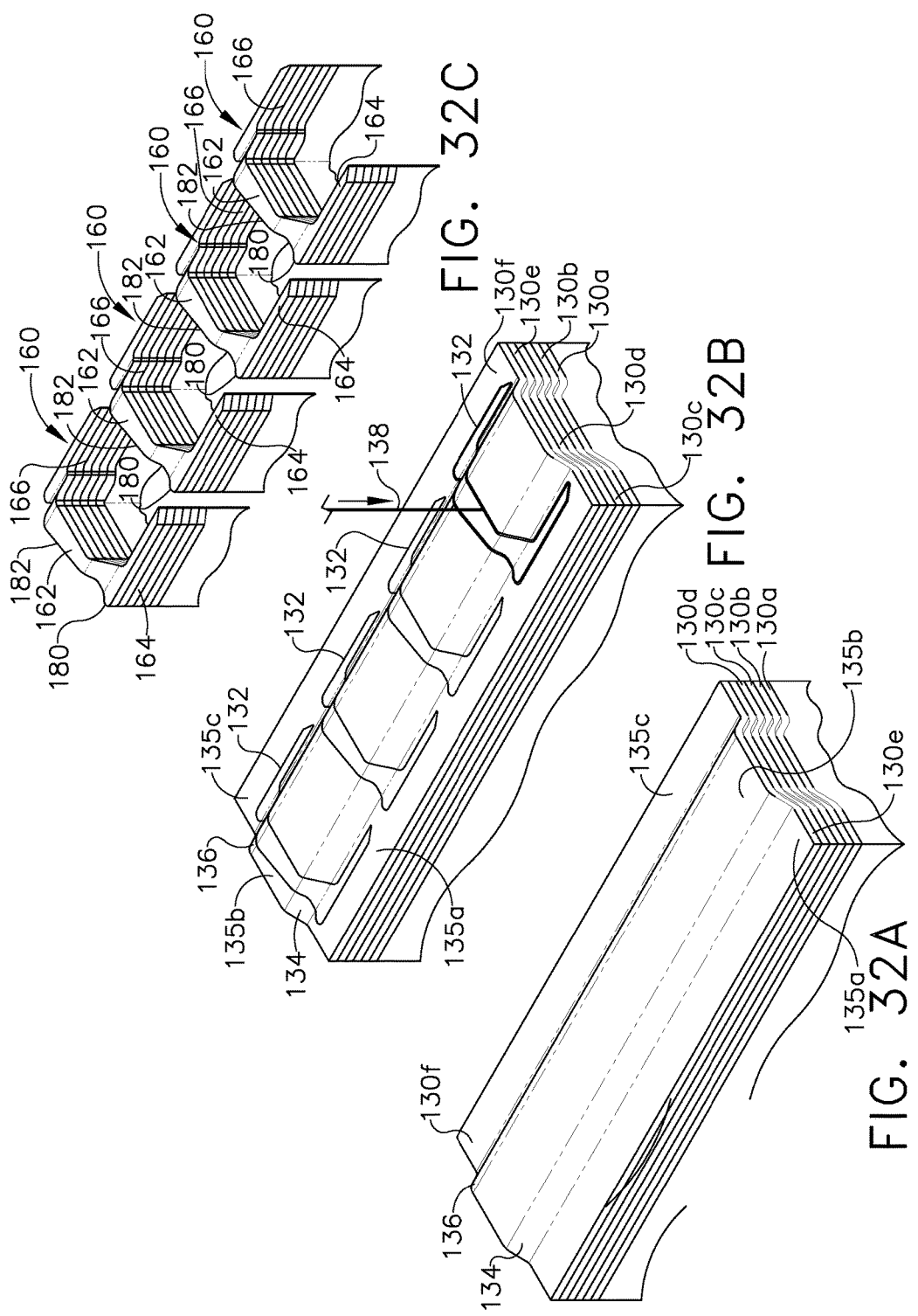

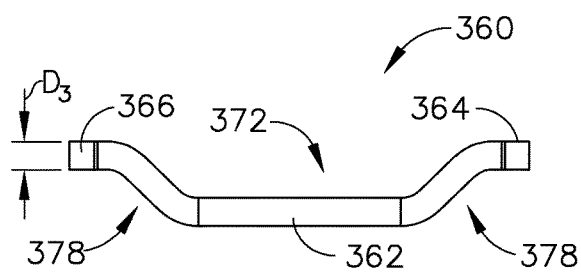
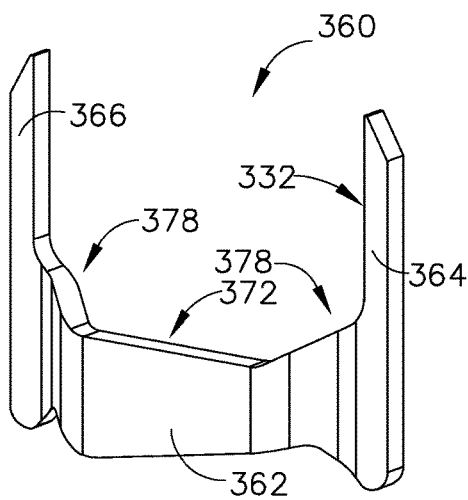
FIG. 42
FIG. 41
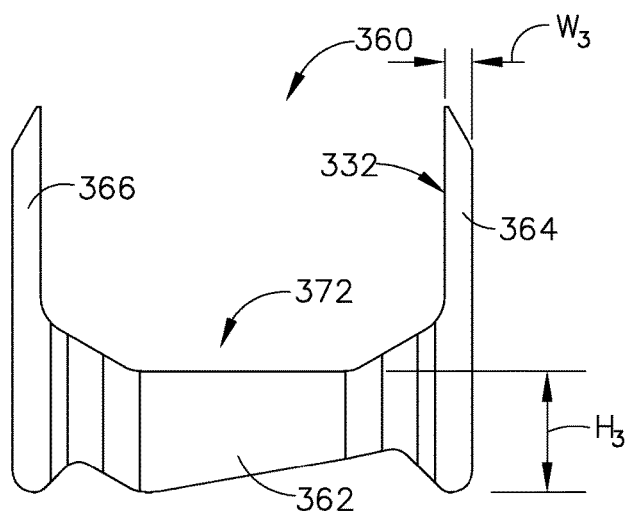
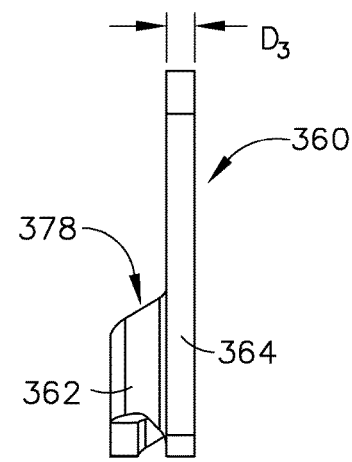
FIG. 43
FIG. 44

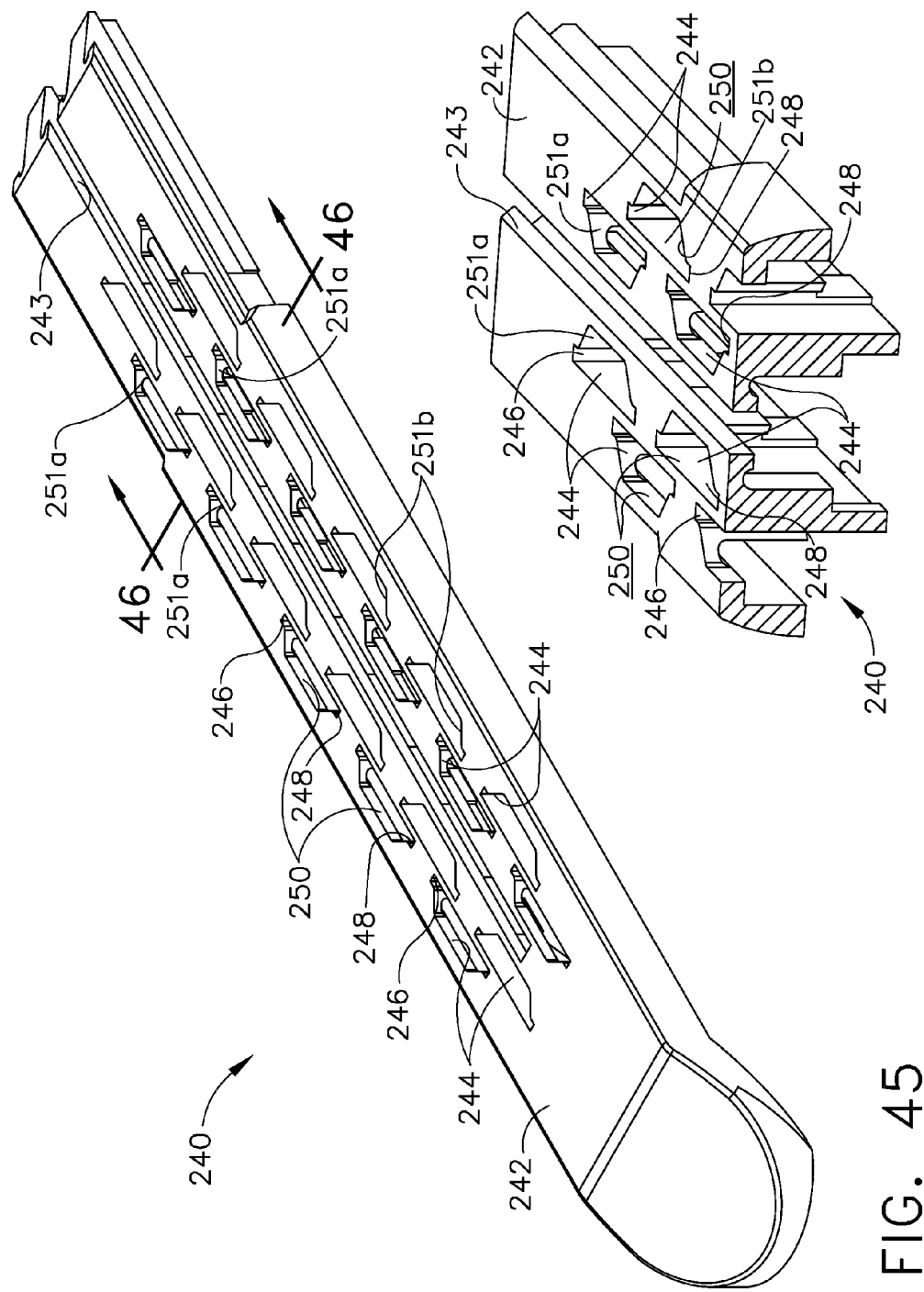

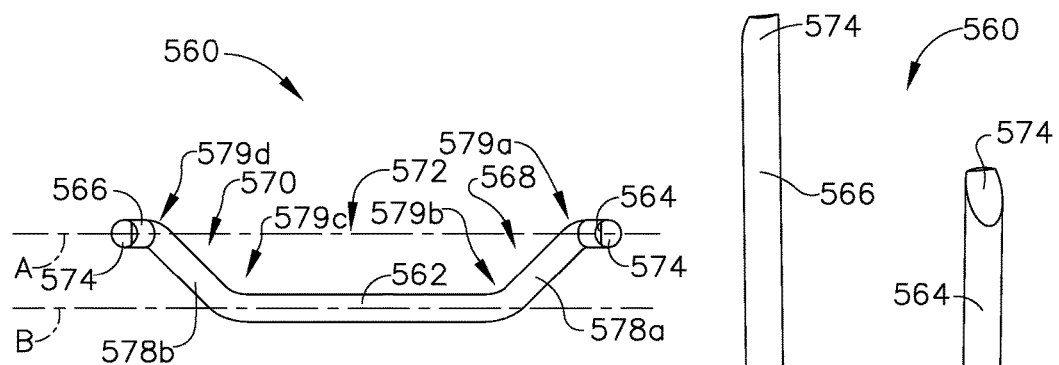
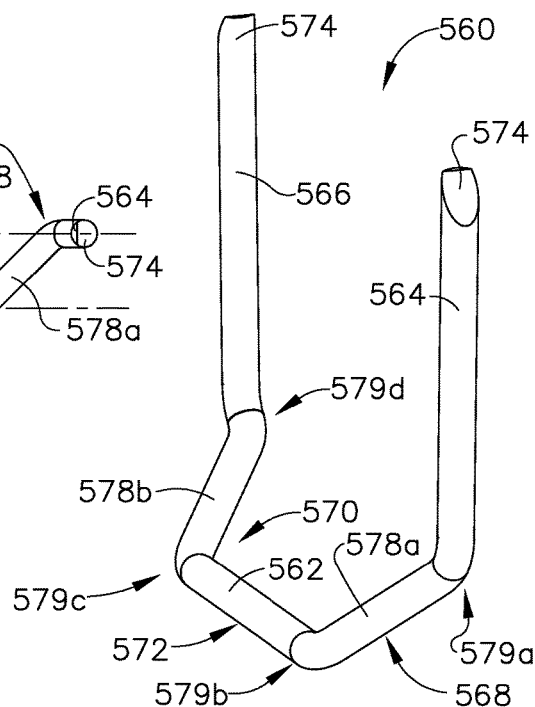
FIG. 53
FIG. 52
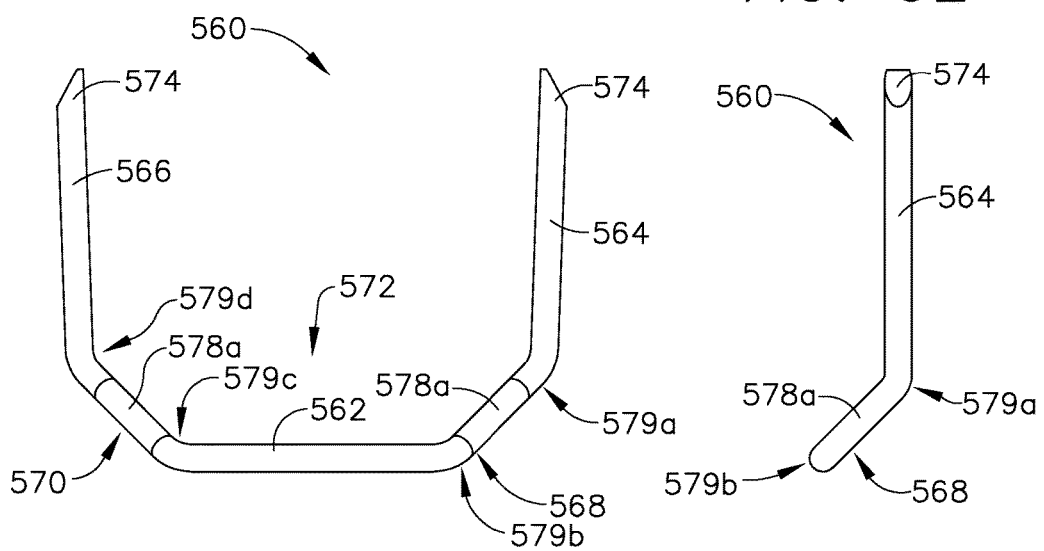
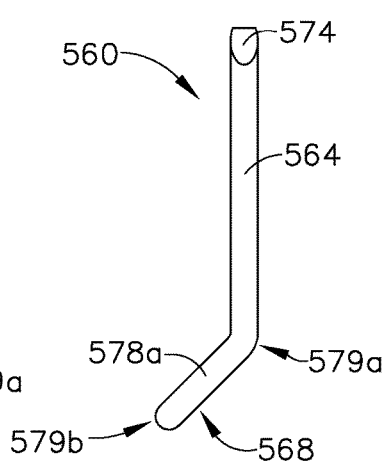
FIG. 54
FIG. 55

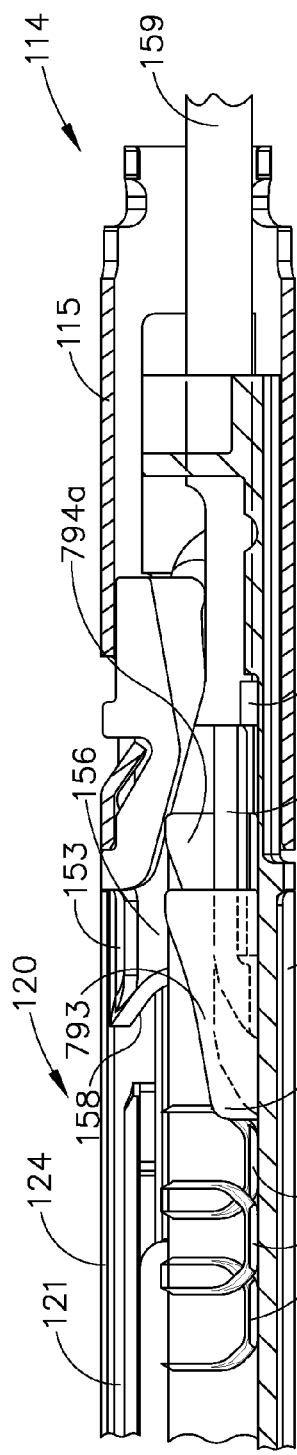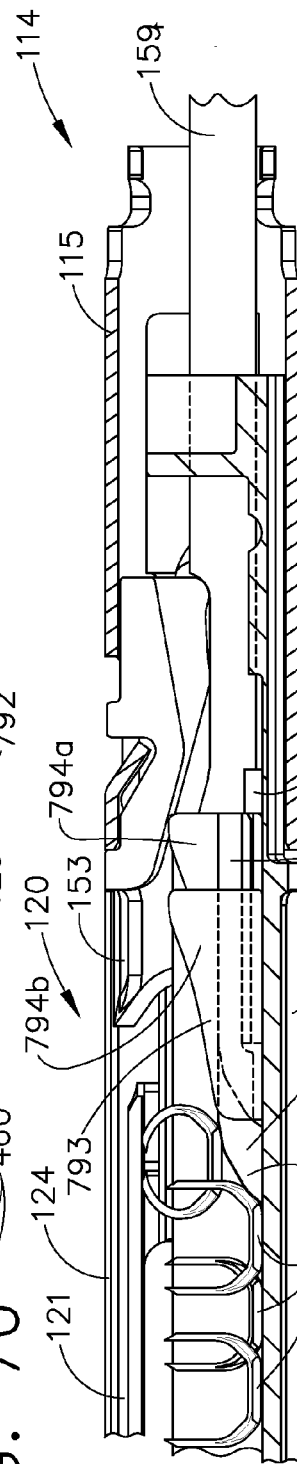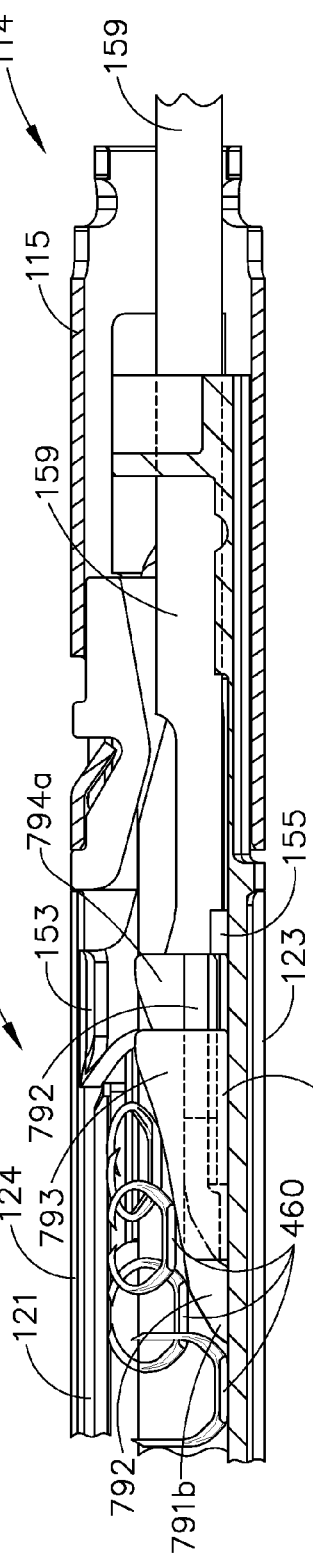

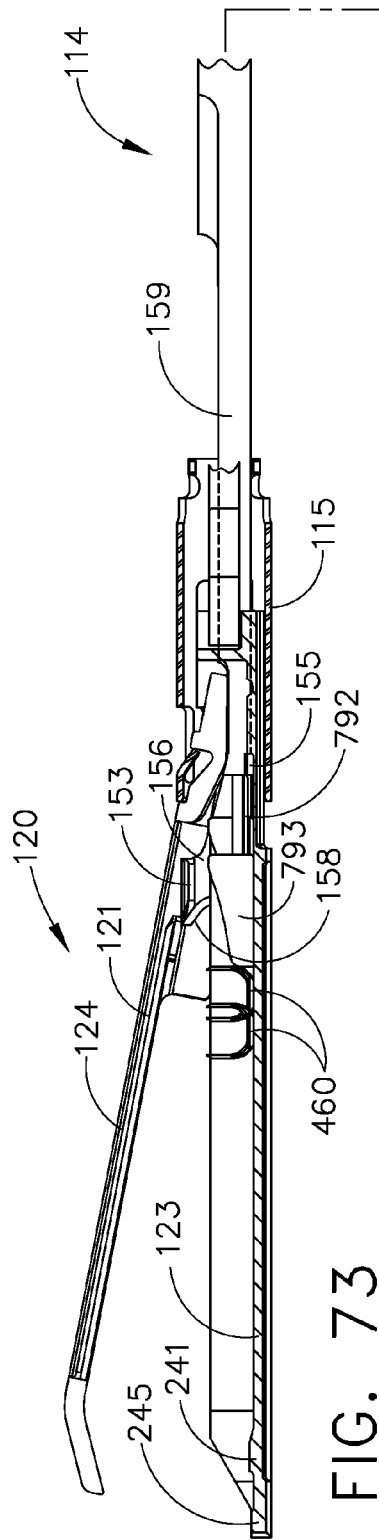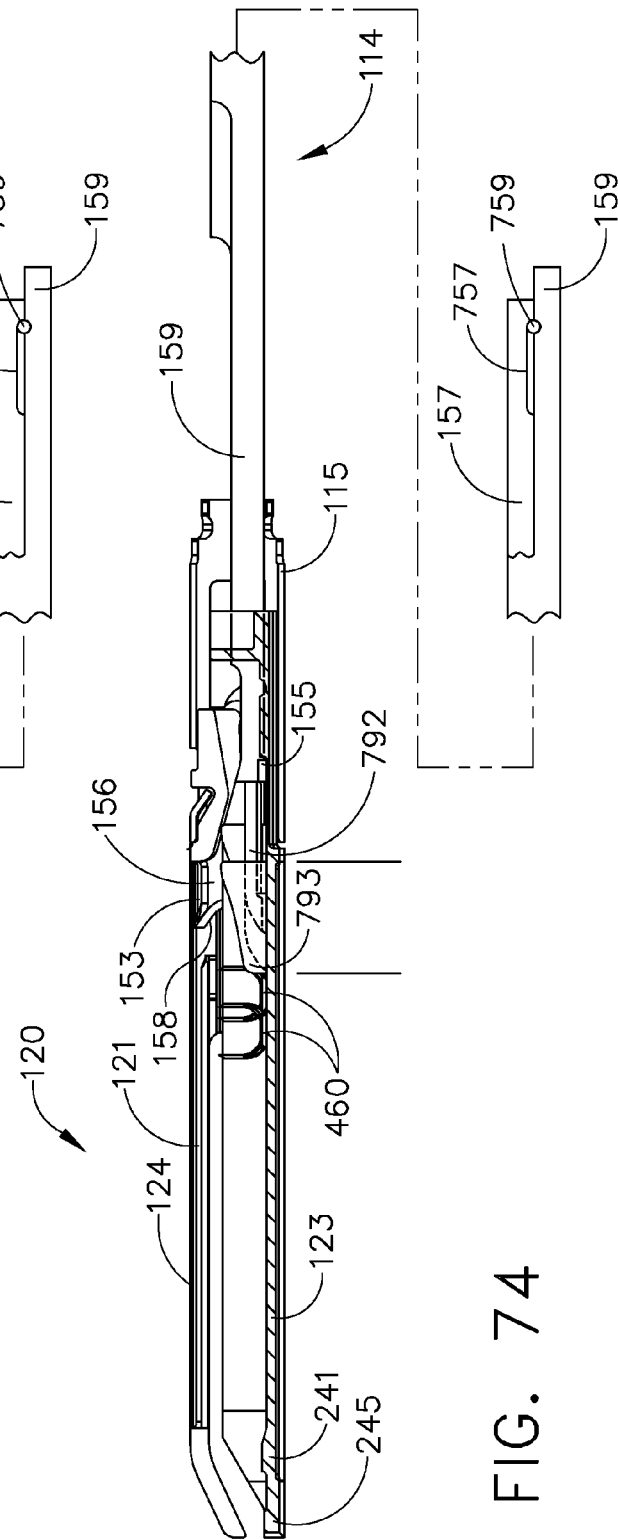

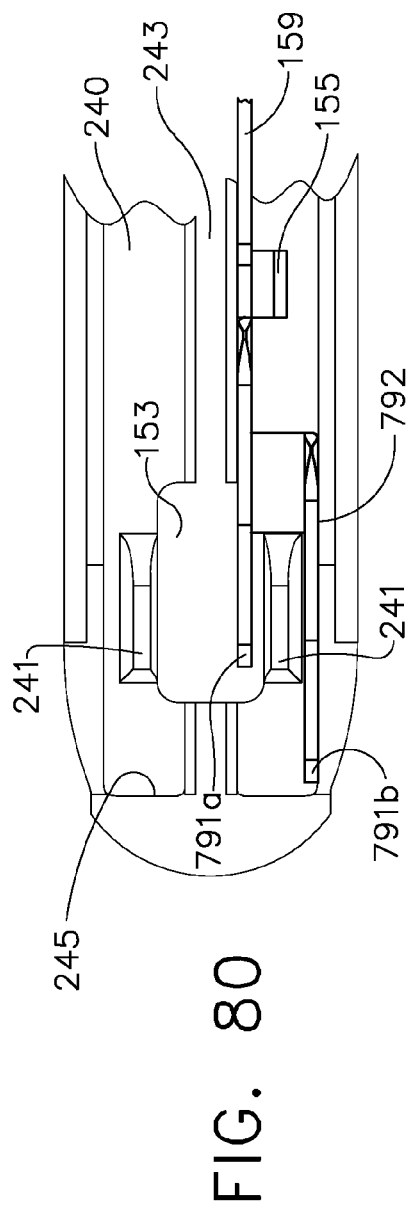
FIG. 80
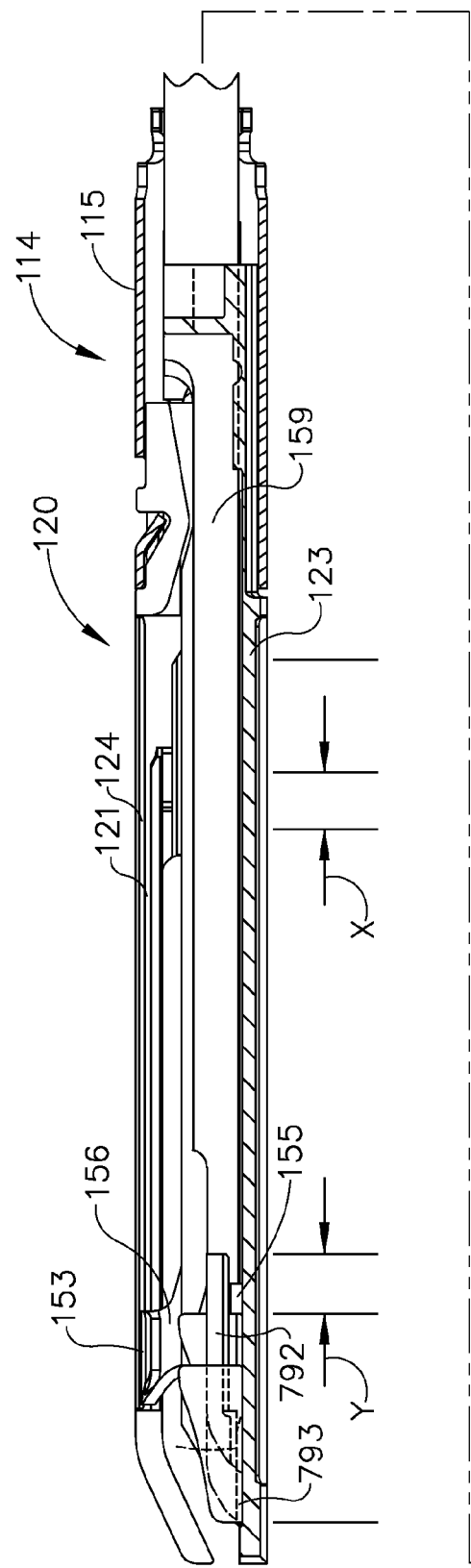
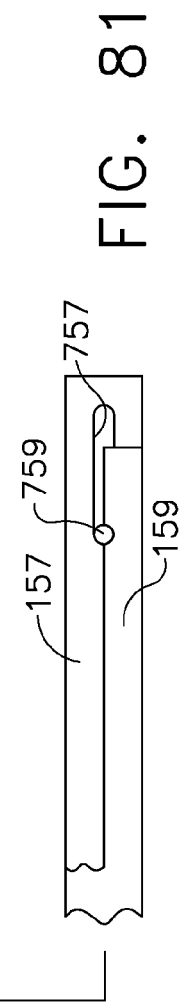
FIG. 81

SURGICAL STAPLES

FIELD

The present invention relates to surgical instruments and, in various arrangements, to surgical cutting and fastening instruments that are designed to cut and fasten tissue, fastener cartridges therefor, and surgical fasteners that are designed for use therewith.

BACKGROUND

Surgical staplers are often used to deploy staples into soft tissue to reduce or eliminate bleeding from the soft tissue, especially as the tissue is being transected, for example. Surgical staplers, such as an endocutter, for example, can comprise an end effector which can be moved, or articulated, with respect to an elongated shaft assembly. End effectors are often configured to secure soft tissue between first and second jaw members where the first jaw member often includes a staple cartridge which is configured to removably store staples therein and the second jaw member often includes an anvil. Such surgical staplers can include a closing system for pivoting the anvil relative to the staple cartridge.

Surgical staplers, as outlined above, can be configured to pivot the anvil of the end effector relative to the staple cartridge in order to capture soft tissue therebetween. In various circumstances, the anvil can be configured to apply a clamping force to the soft tissue in order to hold the soft tissue tightly between the anvil and the staple cartridge. If a surgeon is unsatisfied with the position of the end effector, however, the surgeon must typically activate a release mechanism on the surgical stapler to pivot the anvil into an open position and then reposition the end effector. Thereafter, staples are typically deployed from the staple cartridge by a sled which traverses a channel in the staple cartridge and causes the staples to be deformed against the anvil and secures layers of the soft tissue together. The sled can engage drivers positioned between the staples and the sled to deploy the staples from the staple cartridge. Often, as known in the art, the staples are deployed in several staple lines, or rows, in order to more reliably secure the layers of tissue together. Staples are typically deformed to a "B-form" by the anvil of the end effector. The end effector may also include a cutting member, such as a knife, for example, which is advanced between rows of the staples to resect the soft tissue after the layers of the soft tissue have been stapled together.

Such surgical staplers and end effectors may be sized and configured to be inserted into a body cavity through a trocar or other access opening. The end effector is typically coupled to an elongated shaft that is sized to pass through the trocar or opening. The elongated shaft assembly is often operably coupled to a handle that supports control systems and/or triggers for controlling the operation of the end effector. To facilitate proper location and orientation of the end effector within the body, many surgical instruments are configured to facilitate articulation of the end effector relative to a portion of the elongated shaft.

The foregoing discussion is intended only to illustrate various aspects of the related art in the field of the invention at the time, and should not be taken as a disavowal of claim scope.

DESCRIPTION OF THE FIGURES

The features and advantages of this invention, and the manner of attaining them, will become more apparent and the invention itself will be better understood by reference to the following description of embodiments of the invention taken in conjunction with the accompanying drawings, wherein:

FIGS. 32A-32C illustrate a method for forming staples from a sheet of material according to various embodiments of the present disclosure;

FIG. 41 is a perspective view of a staple according to various embodiments of the present disclosure;

FIG. 42 is a plan view of the staple of FIG. 41;

FIG. 43 is a front elevation view of the staple of FIG. 41;

FIG. 44 is a side elevation view of the staple of FIG. 41;

FIG. 45 is a perspective view of a staple cartridge according to various embodiments of the present disclosure;

FIG. 46 is a cross-sectional perspective view of the staple cartridge of FIG. 45 taken along the plane indicated in FIG. 45;

FIG. 52 is a perspective view of a staple according to various embodiments of the present disclosure;

FIG. 53 is a plan view of the staple of FIG. 52;

FIG. 54 is a front elevation view of the staple of FIG. 52;

FIG. 55 is a side elevation view of the staple of FIG. 52;

FIG. 70 is a cross-sectional view of the end effector of FIG. 65 illustrating the firing actuator in an unfired, unextended condition;

FIG. 71 is a cross-sectional view of the end effector of FIG. 65 illustrating the firing actuator in an extended condition;

FIG. 72 is a cross-sectional view of the end effector of FIG. 65 illustrating the firing actuator in an extended, advanced condition;

FIG. 73 is a cross-sectional view of the end effector of FIG. 65 illustrating an anvil of the end effector in an open position and the firing actuator in an unfired, unextended condition;

FIG. 74 is a cross-sectional view of the end effector of FIG. 65 illustrating the anvil in a closed position and the firing actuator in an unfired, unextended condition;

FIG. 80 is a partial cross-sectional plan view of the end effector of FIG. 65 illustrated in a fully-fired condition;

FIG. 81 is a cross-sectional elevational view of the end effector of FIG. 65 illustrated in the configuration depicted in FIG. 80;

DETAILED DESCRIPTION

Figure 1:
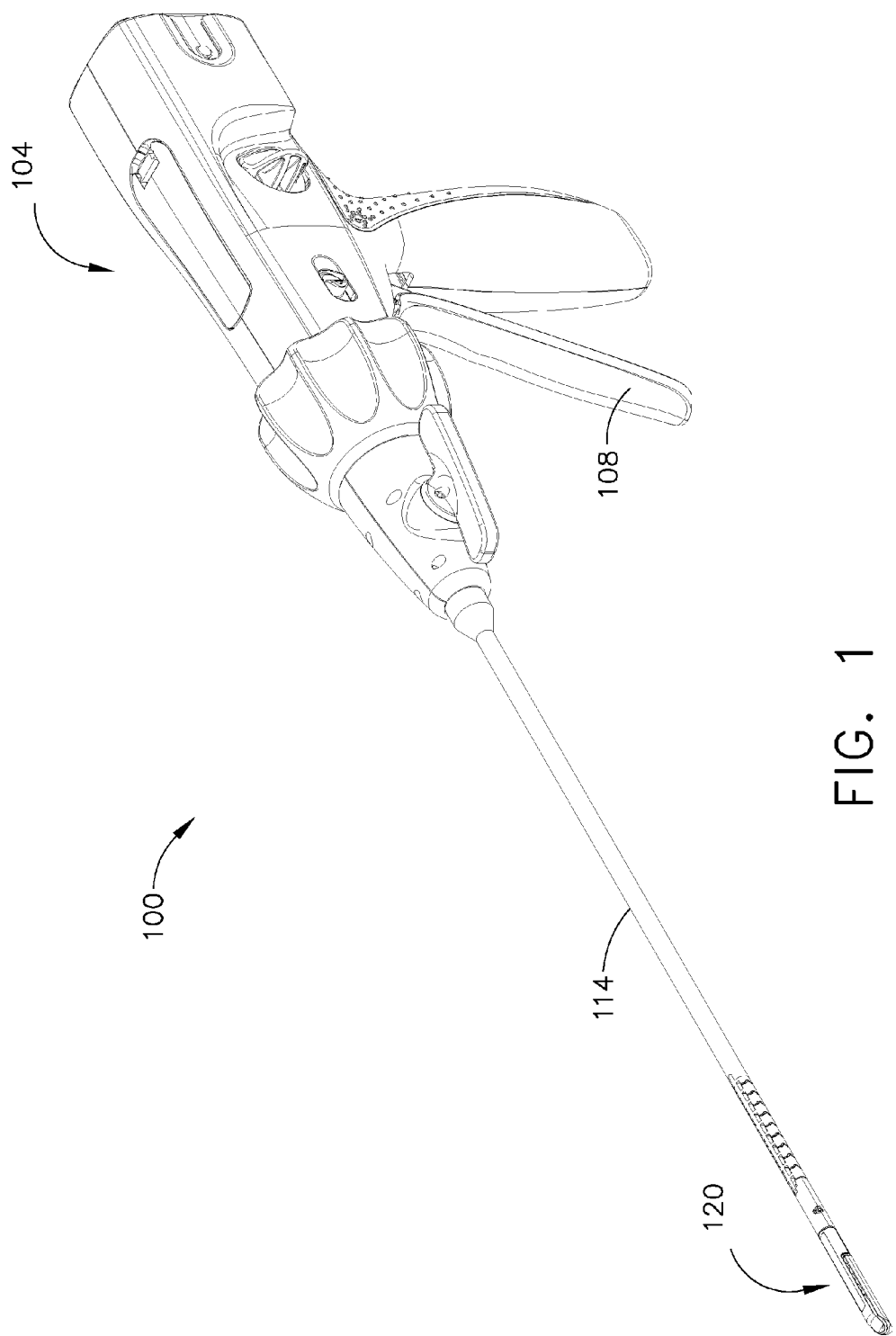
FIG. 1 is a perspective view of a surgical instrument according to various embodiments of the present disclosure.

Applicant of the present application also owns the following patent applications that were filed on Dec. 23, 2013 and which are each incorporated by reference herein in their respective entireties:

U.S. patent application Ser. No. 14/138,554, entitled SURGICAL INSTRUMENTS WITH ARTICULATABLE SHAFT ARRANGEMENTS, now U.S. Patent Application Publication No. 2015/0173789;

U.S. patent application Ser. No. 14/138,465, entitled SURGICAL STAPLES AND STAPLE CARTRIDGES, now U.S. Patent Application Publication No. 2015/0173744;

U.S. patent application Ser. No. 14/138,474, entitled ARTICULATABLE SURGICAL INSTRUMENTS WITH SEPARATE AND DISTINCT CLOSING AND FIRING SYSTEMS, now U.S. Patent Application Publication No. 2015/0173745;

U.S. patent application Ser. No. 14/138,485, entitled SURGICAL CUTTING AND STAPLING INSTRUMENTS WITH INDEPENDENT JAW CONTROL FEATURES, now U.S. Patent Application Publication No. 2015/0173746;

U.S. patent application Ser. No. 14/138,475, entitled SURGICAL STAPLES AND STAPLE CARTRIDGES, now U.S. Patent Application Publication No. 2015/0173749;

U.S. patent application Ser. No. 14/138,481, entitled SURGICAL STAPLES AND METHODS FOR MAKING THE SAME, now U.S. Patent Application Publication No. 2015/0173750;

U.S. Design Patent Application Serial No. 29/477,488, entitled SURGICAL FASTENER;

U.S. patent application Ser. No. 14/138,505, entitled FASTENER CARTRIDGE COMPRISING AN EXTENDABLE FIRING MEMBER, now U.S. Patent Application Publication No. 2015/0173760;

U.S. patent application Ser. No. 14/138,518, entitled FASTENER CARTRIDGE COMPRISING A FIRING MEMBER CONFIGURED TO DIRECTLY ENGAGE AND EJECT FASTENERS FROM THE FASTENER CARTRIDGE, now U.S. Patent Application Publication No. 2015/0173761;

U.S. patent application Ser. No. 14/138,530, entitled FASTENER CARTRIDGE COMPRISING A FIRING MEMBER INCLUDING FASTENER TRANSFER SURFACES, now U.S. Patent Application Publication No. 2015/0173762;

U.S. patent application Ser. No. 14/138,507, entitled MODULAR SURGICAL INSTRUMENTS, now U.S. Patent Application Publication No. 2015/0173747;

U.S. patent application Ser. No. 14/138,497, entitled SURGICAL CUTTING AND STAPLING INSTRUMENTS WITH ARTICULATABLE END EFFECTORS, now U.S. Patent Application Publication No. 2015/0173755; and U.S. patent application Ser. No. 14/138,516, entitled SURGICAL CUTTING AND STAPLING METHODS, now U.S. Patent Application Publication No. 2015/0173756.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 2:
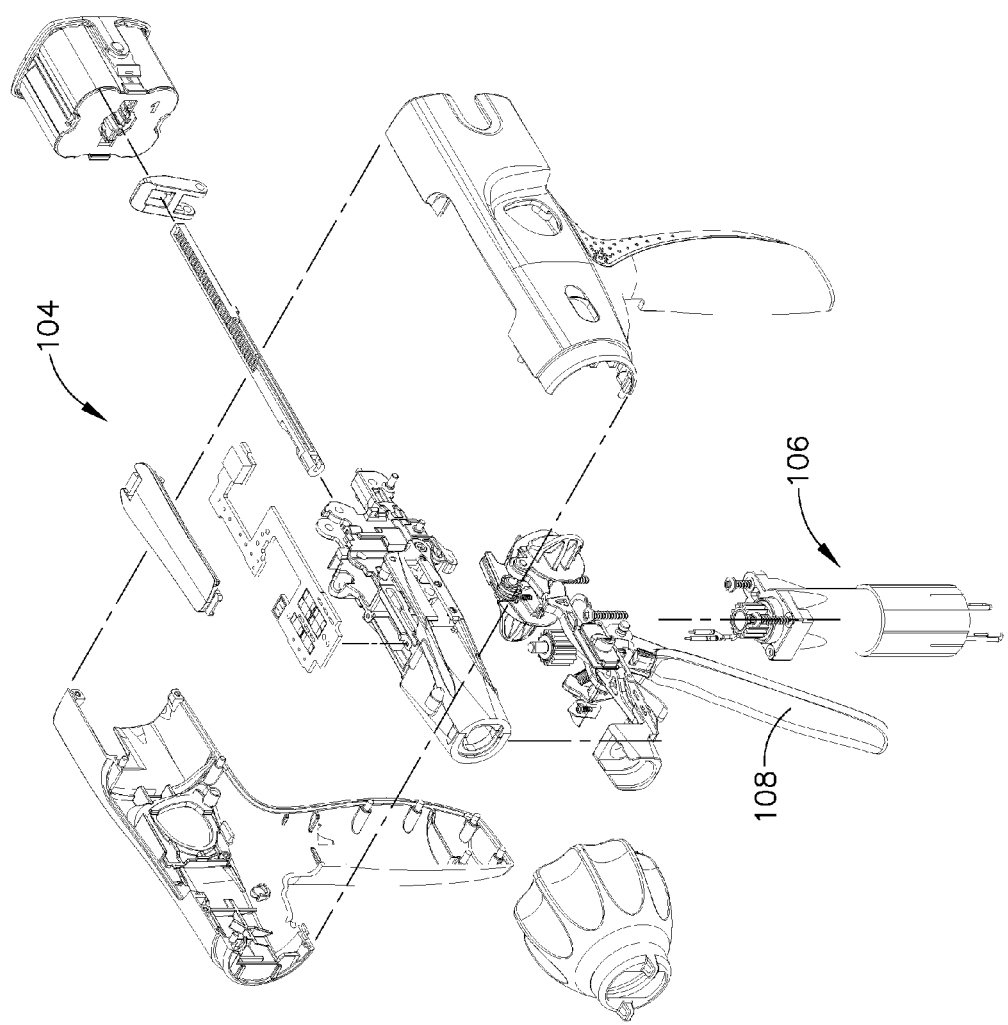
FIG. 2 is an exploded perspective view of a handle assembly of the surgical instrument of FIG. 1 according to various embodiments of the present disclosure.
Figure 3:
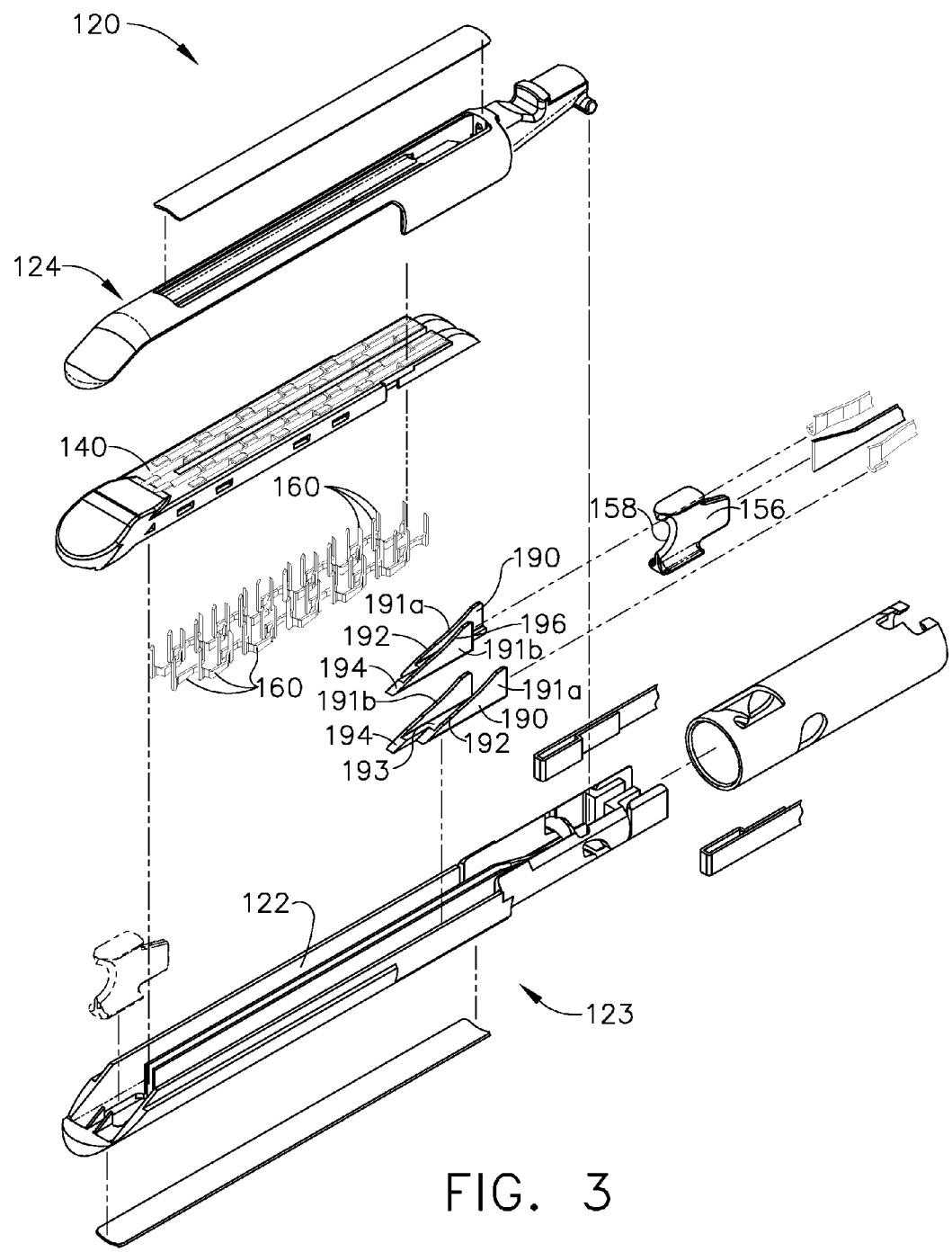
FIG. 3 is an exploded perspective view of an end effector of the surgical instrument of FIG. 1 according to various embodiments of the present disclosure.

Referring to an exemplary embodiment depicted in FIGS. 1-3, a surgical instrument 100 can include a handle assembly 104, a shaft 114 extending from the handle assembly 104, and an end effector 120 extending from the shaft 114. Referring primarily to FIG. 3, a staple cartridge 140 can be loaded into an elongate channel 122 of a first jaw 123 of the end effector 120. In certain embodiments, the staple cartridge 140 can be disposable and/or replaceable, for example. Additionally or alternatively, the staple cartridge 140 can be integrated into the end effector 120, for example, and/or the end effector 120 can be disposable and/or replaceable, for example. In various embodiments, the surgical instrument 100 can be motor-driven. For example, referring primarily to FIG. 2, a motor 106 can be positioned in the handle assembly 104. The handle assembly 104 of the surgical instrument 100 can also include a trigger 108. Actuation of the trigger 108 can affect closure of the jaws 123, 124 of the end effector 120, firing of staples 160 from the staple cartridge 140, and/or translation of a firing bar 156 and cutting element 158 through the end effector 120, for example.

Figure 4:
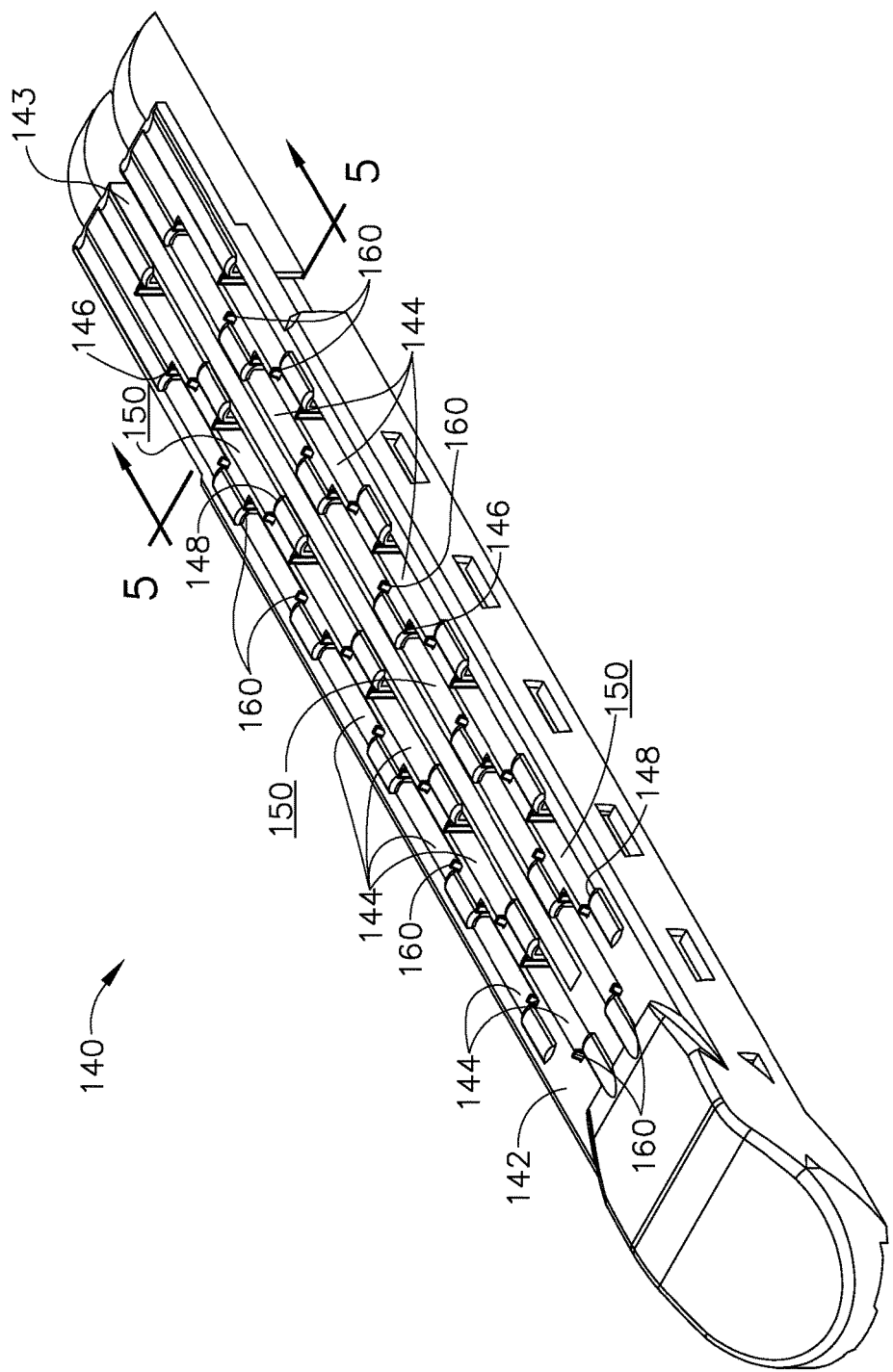
FIG. 4 is a perspective view of a staple cartridge of the end effector of FIG. 3 according to various embodiments of the present disclosure.
Figure 5:
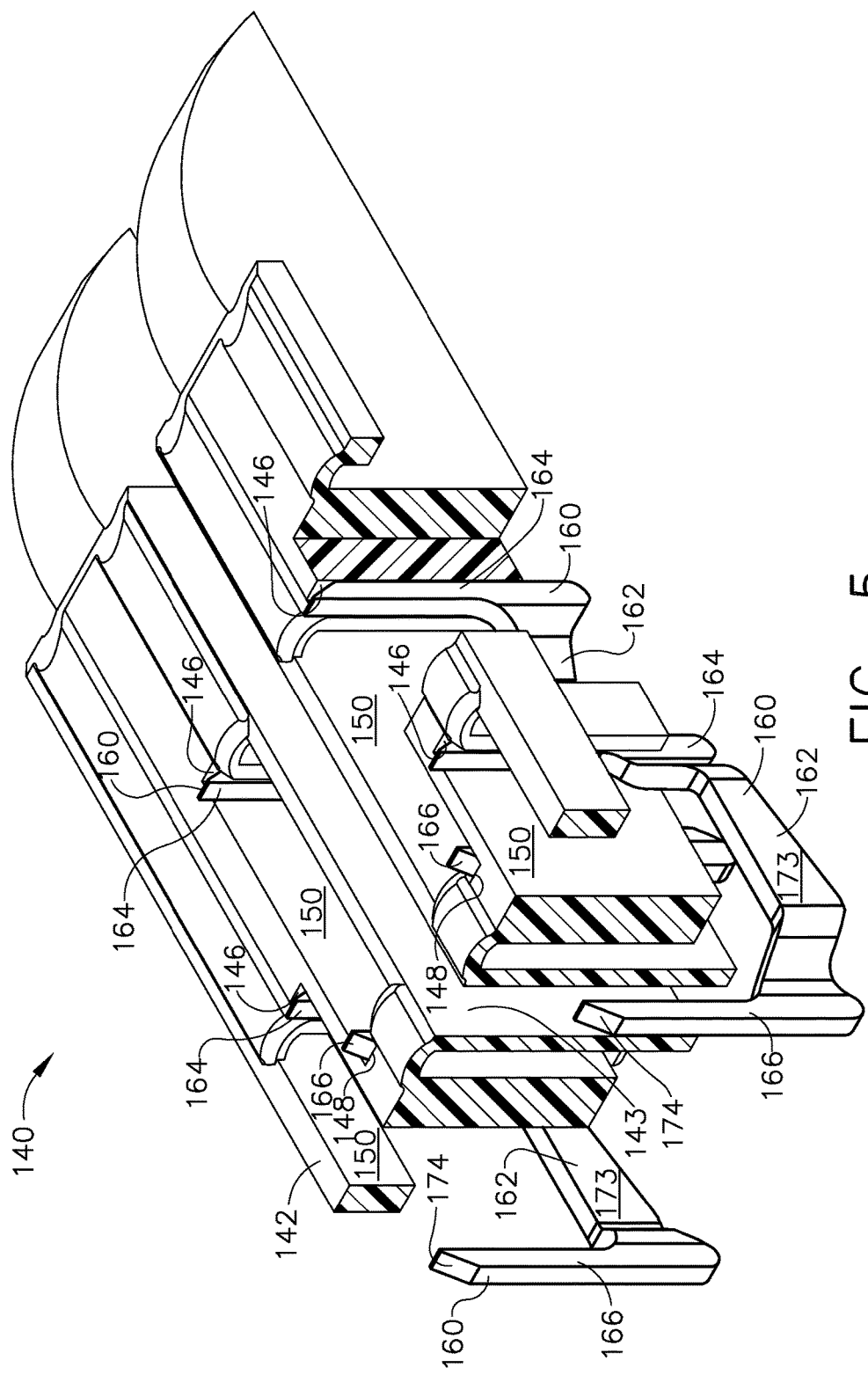
FIG. 5 is a cross-sectional perspective view of the staple cartridge of FIG. 4 taken along the plane indicated in FIG. 4 according to various embodiments of the present disclosure.
Figure 6:
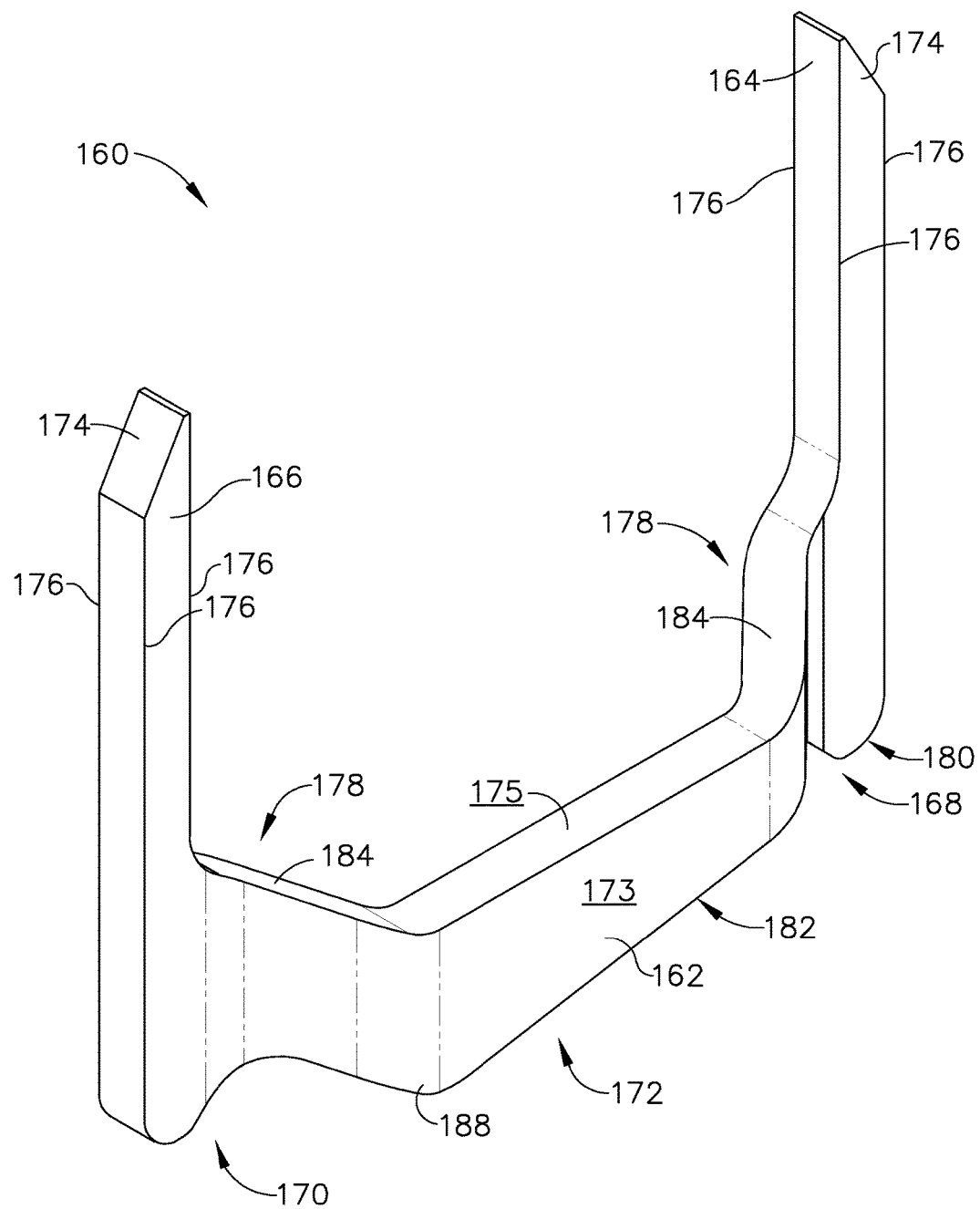
FIG. 6 is a perspective view of the staple depicted in the staple cartridge of FIG. 4 according to various embodiments of the present disclosure.

Referring primarily to FIG. 3, staples 160 can be ejectably positioned in the staple cartridge 140. For example, at least one sled 190 can translate through the staple cartridge 140 to eject the staples 160 from the staple cartridge 140. The firing bar 156 having the cutting element or knife 158 can also translate through the staple cartridge 140 to cut tissue captured between the end effector jaws, 123, 124, for example. As depicted in FIG. 3, the firing bar 156 and cutting element 158 can move from a proximal position in the first jaw 123 to a distal position in the first jaw 123. In various embodiments, tissue positioned intermediate the staple cartridge 140 and the anvil 124 can be stapled by the staples 160, and then cut by the cutting element 158, for example. Referring primarily to FIGS. 4 and 5, the staple cartridge 140 can include a cartridge body 142 and staple cavities 144 defined in the cartridge body 142. Staples, such as staples 160, for example, can be removably positioned in the staple cavities 144. In certain embodiments, each staple cavity 144 can removably store a single staple 160. Each staple cavity 144 can have a proximal end 146 and a distal end 148, for example, and longitudinal sidewalls 150 can extend between the proximal end 146 and the distal end 148 of each staple cavity 144. As described in greater detail herein, the proximal ends 146, the distal ends 148, and/or the longitudinal sidewalls 150 of the staple cavity 144 can guide and/or support the staple 160 during deployment from the staple cavity 144.

Referring now to FIGS. 6-13, the staple 160 can include a base 162, a first staple leg 164 extending from the base 162, and a second staple leg 166 extending from the base 162. The base 162 can have a proximal portion 168 and a distal portion 170, for example, and an intermediate portion 172 of the base 162 can be positioned between the proximal portion 168 and the distal portion 170, for example. As depicted in FIGS. 6-13, the first staple leg 164 can extend from the proximal portion 168 of the base 162, and the second staple leg 166 can extend from the distal portion 170 of the base 162. The staple legs 164, 166 can include a tip 174, for example, which can have a pointed or substantially pointed end. In various embodiments, the tip 174 can facilitate piercing into and/or through tissue, for example. In certain embodiments, the staple legs 164, 166 can include corner edges 176, which can be sharp, or substantially sharp, for example, and can also facilitate piercing into and/or through tissue, for example. In other embodiments, the staple legs 164, 166 can include rounded corner edges.

Referring still to FIGS. 6-13, chamfers 184, 186 can be positioned between the staple legs 164, 166 and the base 162. For example, an upper chamfer 184 can extend between the staple legs 164, 166 and the base 162, and/or a lower chamfer 186 can extend between the staple legs 164, 166 and the base 162. When tissue is captured by the staple 160, the tissue can be compressed between the base 162 and the deformed staple legs 164, 166, and the chamfers 184, 186 may contact the compressed tissue. In various embodiments, the chamfers 184, 186 can compress the captured tissue, for example, and may prevent the base 162 from unintentionally piercing and/or cutting the captured tissue, for example.

In various embodiments, the base 162 of the staple 160 may be asymmetrical relative to the staple legs 164, 166. For example, referring primarily to FIG. 10, a first axis A may be defined between the first and second staple legs 164, 166, and the base 162 can be asymmetrical relative to the first axis A. The base 162 can be non-linear, for example, and can include at least one laterally contoured portion 178 that bends or curves away from the axis A. The base 162, or at least a portion of the base 162, can be defined by a second axis B. The contoured portion 178 can be include straight and/or curved regions, and may be generally non-parallel to the first axis A and the second axis B, for example. For example, the contoured portion 178 can bend or curve away from the first axis A, include a straight or substantially straight portion, and bend or curve toward the second axis B (FIG. 10).

Figure 10:
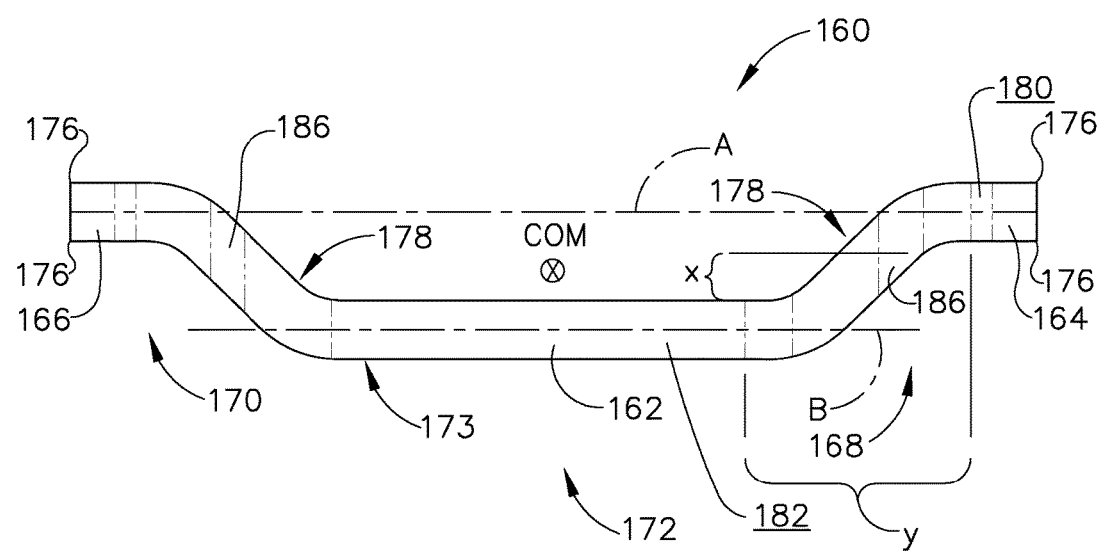
FIG. 10 is a bottom plan view of the staple of FIG. 6.
Figure 11:
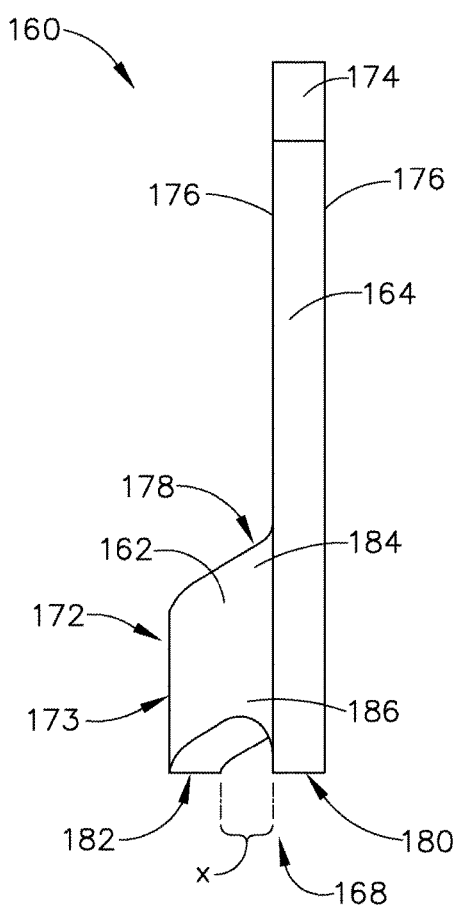
FIG. 11 is a right elevation view of the staple of FIG. 6.
Figure 12:
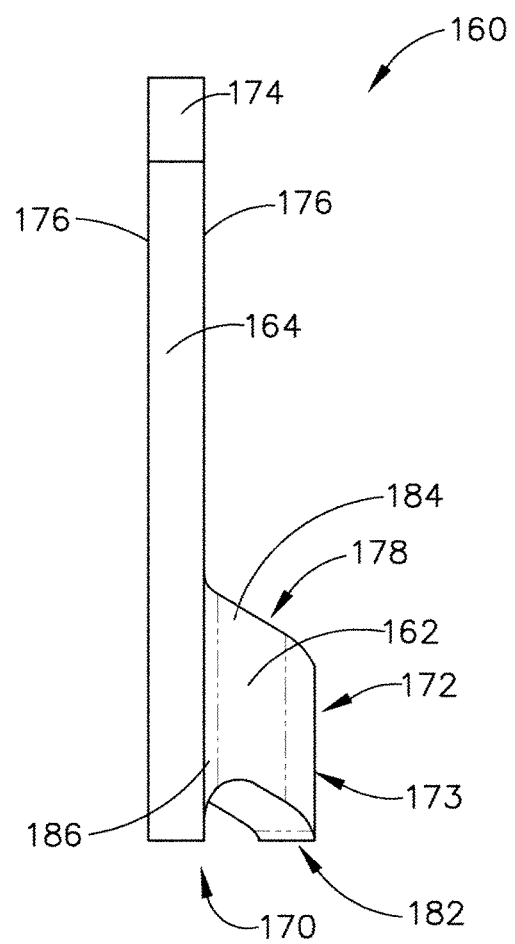
FIG. 12 is a left elevation view of the staple of FIG. 6.
Figure 13:
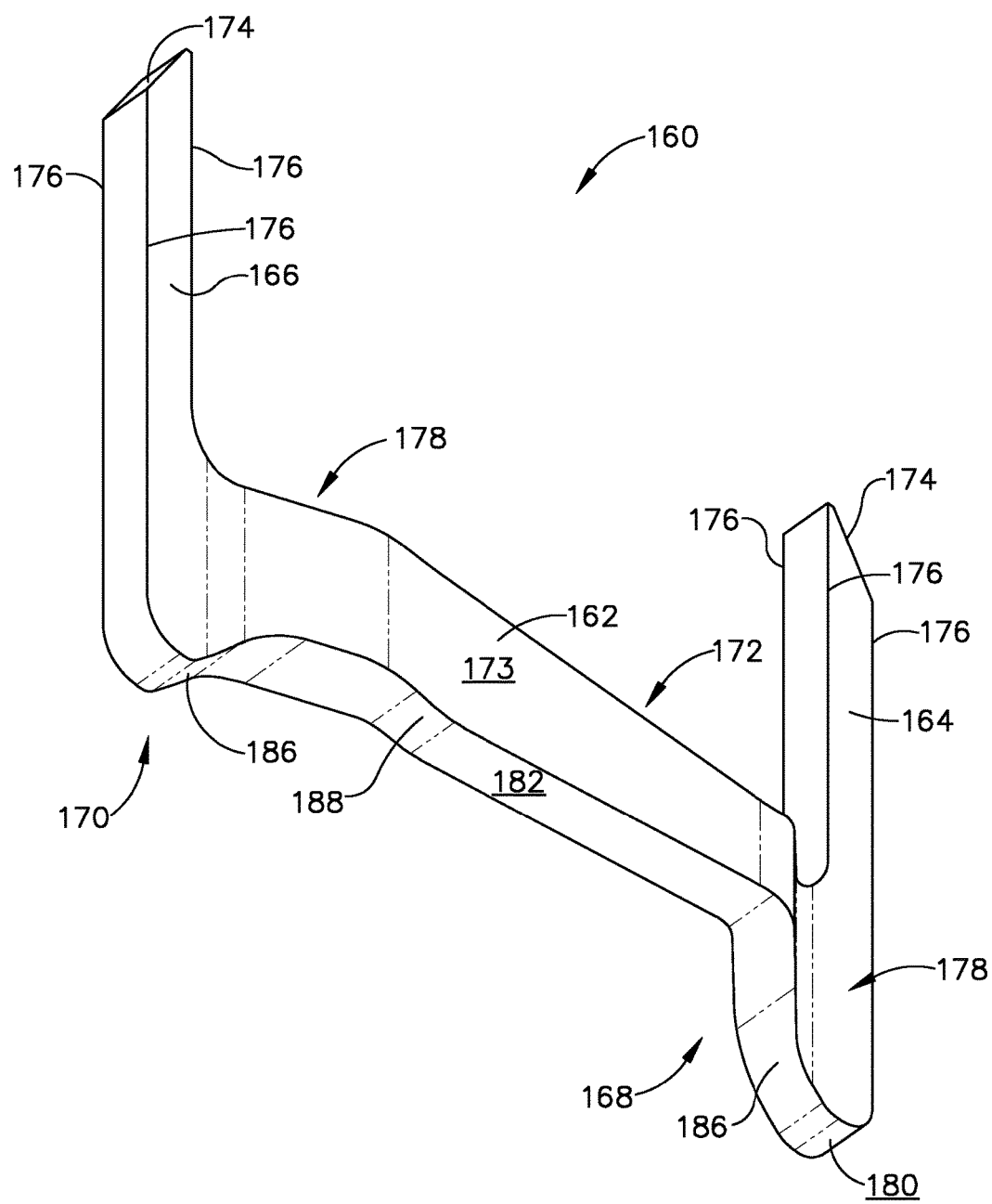
FIG. 13 is a perspective view of the staple of FIG. 6.

Referring still to FIG. 10, the center of mass (COM) of the staple 160 can be offset from the first axis A. In various embodiments, a portion of the base 162 can extend along the second axis B, for example, which can be parallel or substantially parallel to the first axis A. For example, the intermediate portion 172 of the base 162 can be parallel or substantially parallel to the first axis A. A contoured portion 178 can be positioned between the proximal portion 168 and the intermediate portion 172, for example, and another contoured portion 178 can be positioned between the distal portion 170 and the intermediate portion 172, for example. The contoured portions 178 can laterally offset the intermediate portion 172 of the base 162 from the staple legs 164, 166 and from the first axis A, for example. In certain embodiments, the staple legs 164, 166 can be positioned in a first plane defined by the first axis A, for example, and the intermediate portion 172 of the base 162 can be positioned in a second plane defined by the second axis B. The second plane can be parallel, or substantially parallel, to the first plane, for example, and the center of mass (COM) of the staple 160 can be positioned between the first plane and the second plane. In such embodiments, the staple 160 can include a leg formation plane, e.g., the plane defined by the first axis A, which can be offset from the COM of the staple 160. For example, deformation of the staple 160 can form a modified "B-form", for example, and the staple legs 164, 166 may be non-coplanar and/or laterally offset from the intermediate portion 172 of the staple base 162. In various instances, the modified "B-form" staple formation can engage, capture, compress, and/or affect a greater volume of tissue, for example. Additionally, in certain instances, the modified "B-form" staple formation can exert forces on the engaged tissue in different and/or divergent directions, for example. Modified "B-form" can define a tissue entrapment area extending in three different directions. For instance, a portion of the tissue entrapment area can be defined in two directions by the legs 164 and 166 and another portion of the tissue entrapment area can be defined in a third direction between the base 162 and the legs 164, 166.

In various embodiments, the intermediate portion 172 of the staple base 162 can include a longitudinal guide surface 173. For example, as described in greater detail herein, the longitudinal guide surface 173 can slide and/or move against a guide surface 150 in the staple cavity 144 (FIGS. 4 and 5) as the staple 160 is fired and/or ejected from the cartridge body 142 (FIGS. 4 and 5), for example. In such embodiments, the longitudinal guide surface 173 can balance and/or stabilize the staple 160 during deployment. Furthermore, the intermediate portion 172 of the staple base 162 can include a tissue-contacting surface 175 (FIG. 9), which can be flat or substantially flat, for example. In various instances, the tissue-contacting surface 175 of the base 162 can form a flat surface for contacting captured tissue, which can provide a broad and/or smooth surface for applying and/or distributing pressure on the captured and/or compressed tissue. In such embodiments, tissue tearing and/or trauma within the staple 160 may be reduced and/or minimized, for example.

In various embodiments, the base 162 of the staple 160 can include one of more drive surfaces. For example, the base 162 can include an initial drive surface 180 and a secondary drive surface 182. Referring still to FIGS. 6-13, the proximal portion 168 of the base 162 can include the initial drive surface 180, for example, and/or the intermediate portion 172 of the base 172 can include the secondary drive surface 182. For example, the proximal portion 168 can include a nub having the first drive surface 180. The nub of the first drive surface 180 can include a rounded and/or sloped surface, for example. The secondary drive surface 182 can comprise a ramp on the intermediate portion 172 of the base 162. For example, the secondary drive surface 182 can be positioned distal to the initial drive surface 180 and/or between the proximal portion 168 and the distal portion 170 of the base 162, for example. The secondary drive surface 182 can include an inclined surface or plane, for example, and can slope downward in the direction of the distal portion 170 (see FIGS. 7 and 8).

Figure 7:
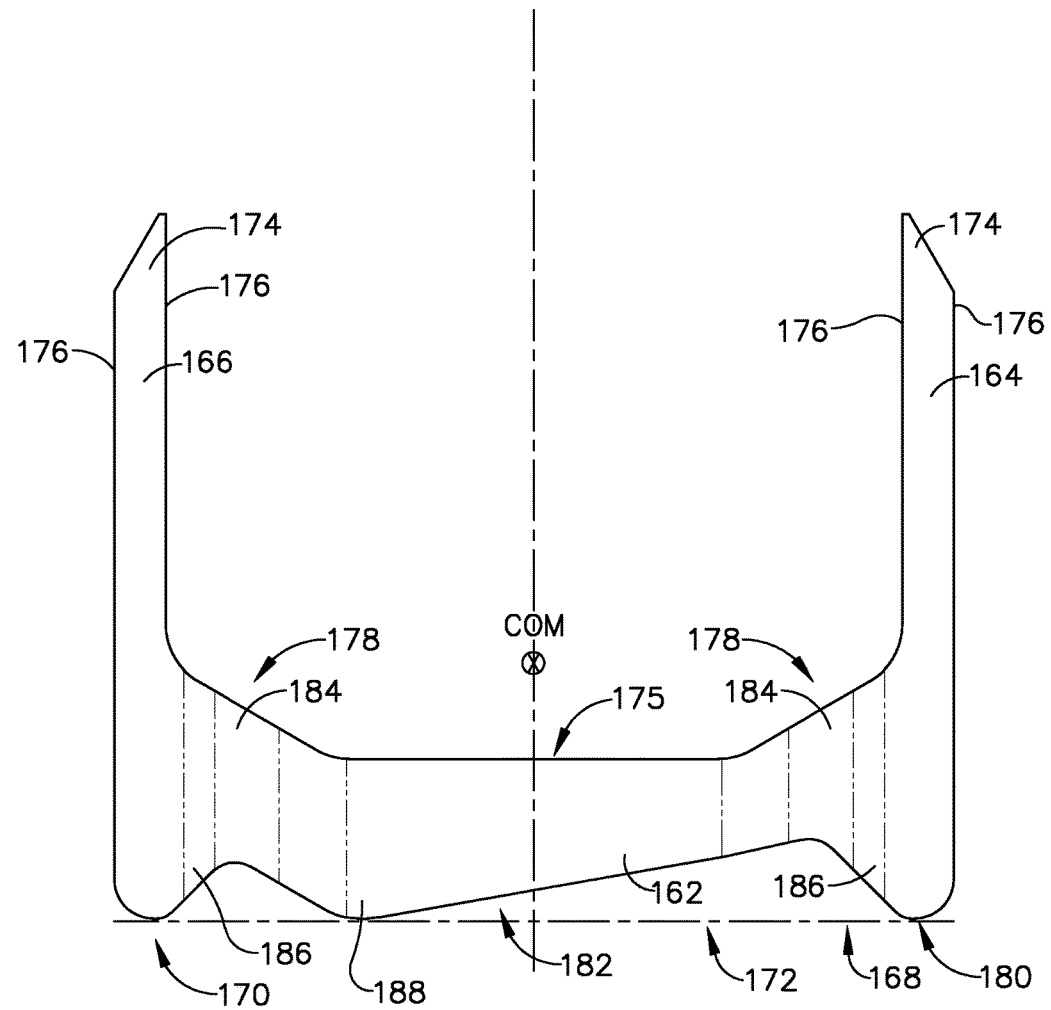
FIG. 7 is a front elevation view of the staple of FIG. 6.
Figure 8:
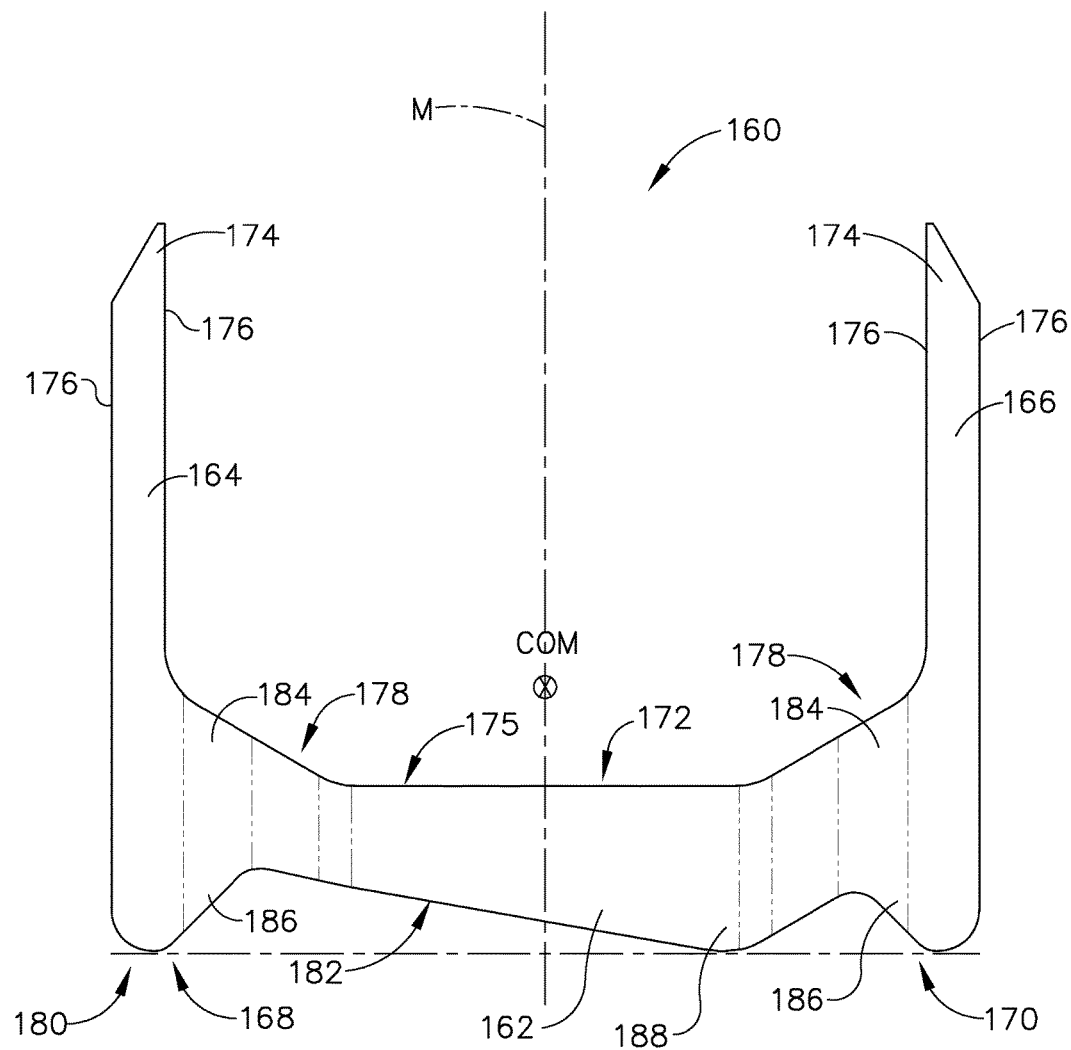
FIG. 8 is a rear elevation view of the staple of FIG. 6.
Figure 9:
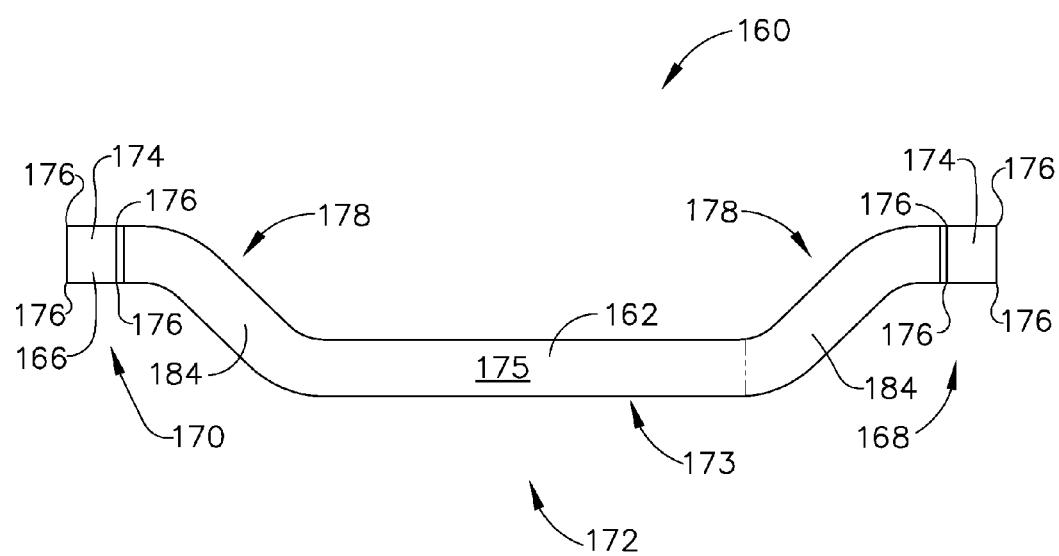
FIG. 9 is a top plan view of the staple of FIG. 6.

Referring primarily to FIGS. 7 and 8, a staple midline M can be defined intermediate the first staple leg 164 and the second staple leg 166. The staple midline M can bisect the staple 160, and can pass through the center of mass (COM) of the staple 160, for example. In various embodiments, the secondary drive surface 182 can extend across the midline M. For example, the secondary drive surface 182 can extend along the intermediate portion 172 of the base 162, and can cross from a proximal side of the midline M to a distal side of the midline M. In such embodiments, during deployment of the staple 160 via the sled 190, as described in greater detail herein, a ramp 192 of the sled 190 can drive the staple 160 at and/or near the midline M of the staple 160 during a portion of the staple's deployment. In various embodiments, the distal end of the secondary drive surface 182 can also include a staple overdrive 188, which is described in greater detail herein. Referring primarily to FIG. 7, the staple overdrive 188 can include the lowest point of the intermediate portion 172 of the base 162 and, in some embodiments, can be vertically aligned with the lowest point of the proximal portion 168 and/or the distal portion 170 of the base 162, for example. In other embodiments, the staple overdrive 188 may be positioned vertically below or above the lowest portion of the proximal portion 168 and/or the distal portion 170 of the base 162.

In various embodiments, the drive surfaces 180, 182 of the staple 160 can be separate and distinct. For example, the drive surfaces 180, 182 can be laterally and/or longitudinally offset, such that the drive surfaces 180, 182 are unconnected and/or nonadjacent. Each drive surface can be discrete, for example. The initial drive surface 180 can overlap a first plane (see axis A in FIG. 10), for example, and the secondary drive surface 182 can overlap a second plane (see axis B in FIG. 10), for example. In certain embodiments, the drive surfaces 180, 182 can be parallel. For example, the initial drive surface 180 can extend along the first axis A (FIG. 10), and the secondary drive surface 180 can extend along the second axis B (FIG. 10). In various embodiments, a lateral gap having a width x (FIGS. 10 and 11) can be defined between the initial drive surface 180 and the secondary drive surface 182, for example. In some embodiments, a longitudinal gap having a width y (FIG. 10) can be defined between the initial drive surface 180 and the secondary drive surface 182, for example. The initial drive surface 180 can be proximal to the secondary drive surface 182, for example. Furthermore, a non-driven portion of the base, such as the lower chamfer 186 of the contoured portion 178 between the proximal portion 168 and the intermediate portion 172, for example, can separate the initial drive surface 180 and the secondary drive surface 182, for example. In various embodiments, the contoured portions 178 can traverse between the first plane defined by axis A and the second plane defined by axis B, for example.

Referring still to FIGS. 6-13, at least one of the drive surfaces 180, 182 of the staple 160 can be integrally formed with the staple 160. For example, the drive surfaces 180, 182 can be defined in the base 162 of the staple 160. The staple 160 can comprise a single, unitary piece, for example, which may integrally include the drive surfaces 180, 182. The drive surfaces 180, 182 can comprise a boundary or perimeter surface of the single, unitary piece, for example. In various circumstances, the staple 160 can be seamless, for example, and many not include any adhered and/or overmolded features, for example. Furthermore, the base 162 and the staple legs 164, 166 can be a contiguous part, and the base 162 can integrally define the drive surfaces 180, 182, for example. In certain instances, as described in greater detail herein, the staple 160 can be stamped or otherwise formed from a single piece of material, for example, and can remain a single piece of material, for example. In various instances, the drive surfaces 180, 182 can comprise a surface or flat of the formed piece.

Referring now to FIGS. 14-17, the sled 190 can drive the staples 160 from the cavities 144 in the cartridge body 142 (FIG. 3). In various instances, the sled 190 can directly contact the staples 160 and/or can directly drive the staples 160. For example, the sled 190 can include a ramp or inclined surface 192, which can contact at least one drive surface 180, 182 of the staple 160. As the sled 190 translates relative to the staple 160, the ramp 192 can push the drive surfaces 180, 182 to lift the staples 160. In various embodiments, the degree of incline of the ramp 192 can vary along the length thereof. For example, the ramp 192 can be designed to lift the staple 160 faster and/or slower during at least part of the staple's deployment. Moreover, the degree of incline of the ramp 192 can be designed and/or selected based on the degree of incline of a staple drive surface 180, 182. For example, the ramp 192 can define an incline that is greater than, less than, and/or equal to the incline of the initial drive surface 180 and/or the secondary drive surface 182. The relationship between the ramp 192 incline and the drive surface 180, 182 incline can affect the speed of staple deployment, for example.

Figure 14:
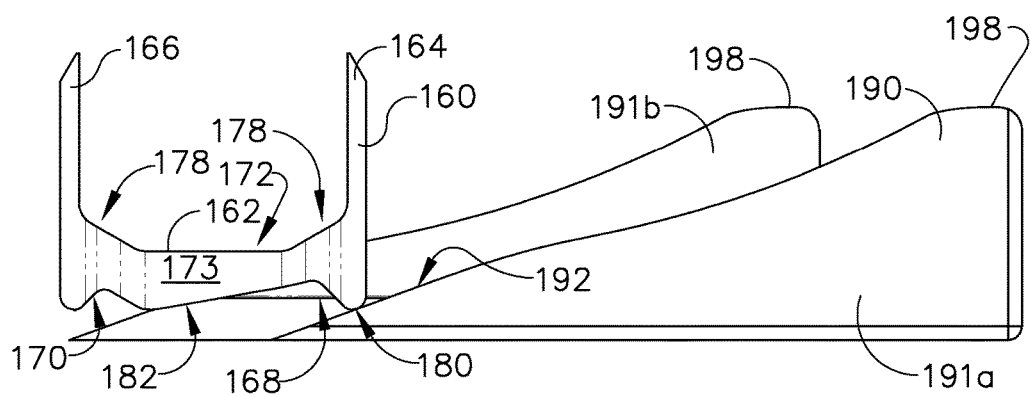
FIG. 14 is an elevation view of the staple of FIG. 6 and a sled of the end effector of FIG. 3, depicting a leading surface of the sled contacting an initial drive surface of the staple, according to various embodiments of the present disclosure.
Figure 15:
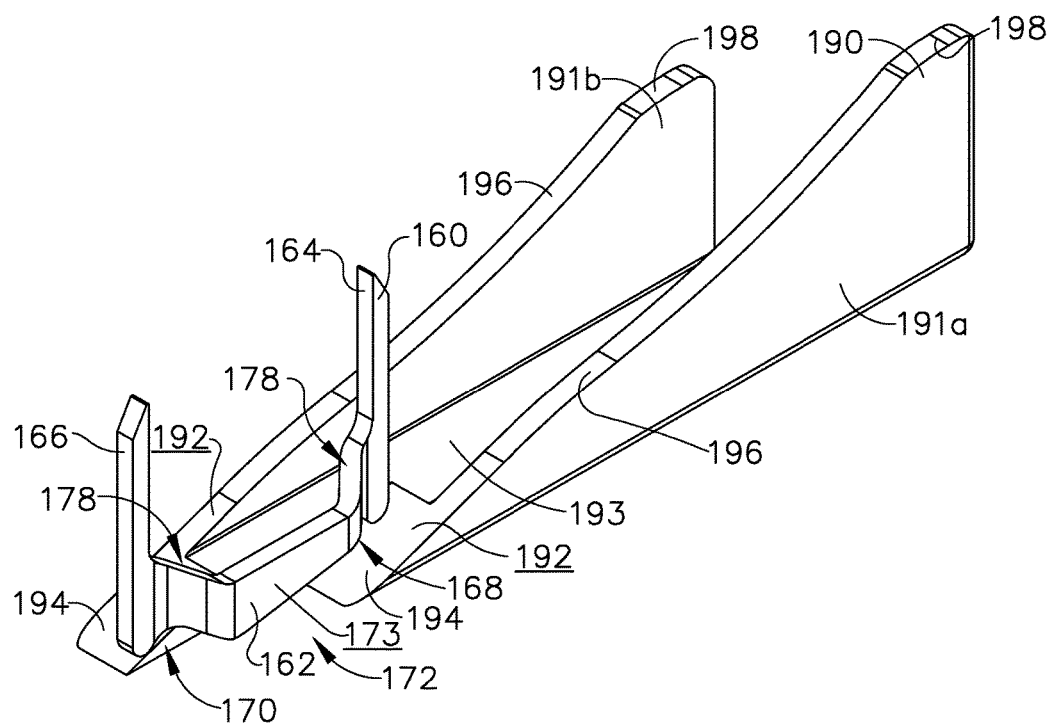
FIG. 15 is a perspective view of the staple and the sled of FIG. 14, depicting the leading surface of the sled contacting the initial drive surface of the staple.
Figure 16:
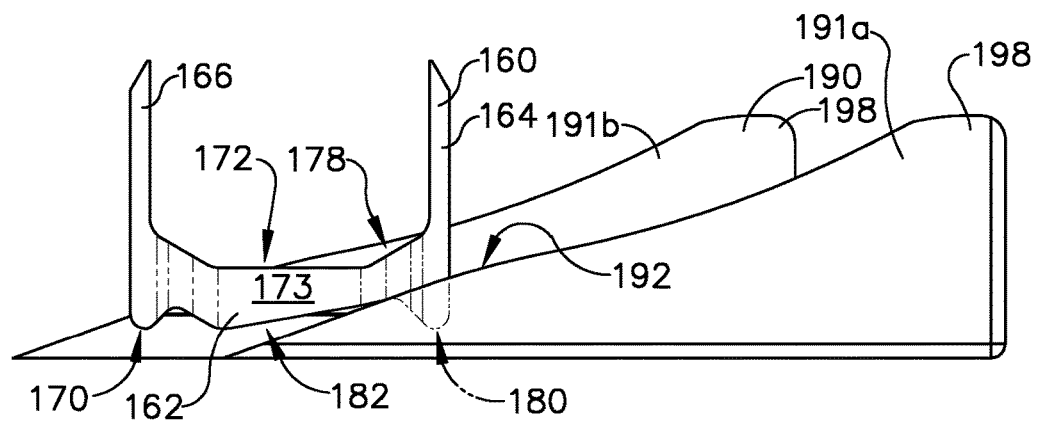
FIG. 16 is an elevation view of the staple and the sled of FIG. 14, depicting a trailing surface of the sled contacting a secondary drive surface of the staple, according to various embodiments of the present disclosure.
Figure 17:
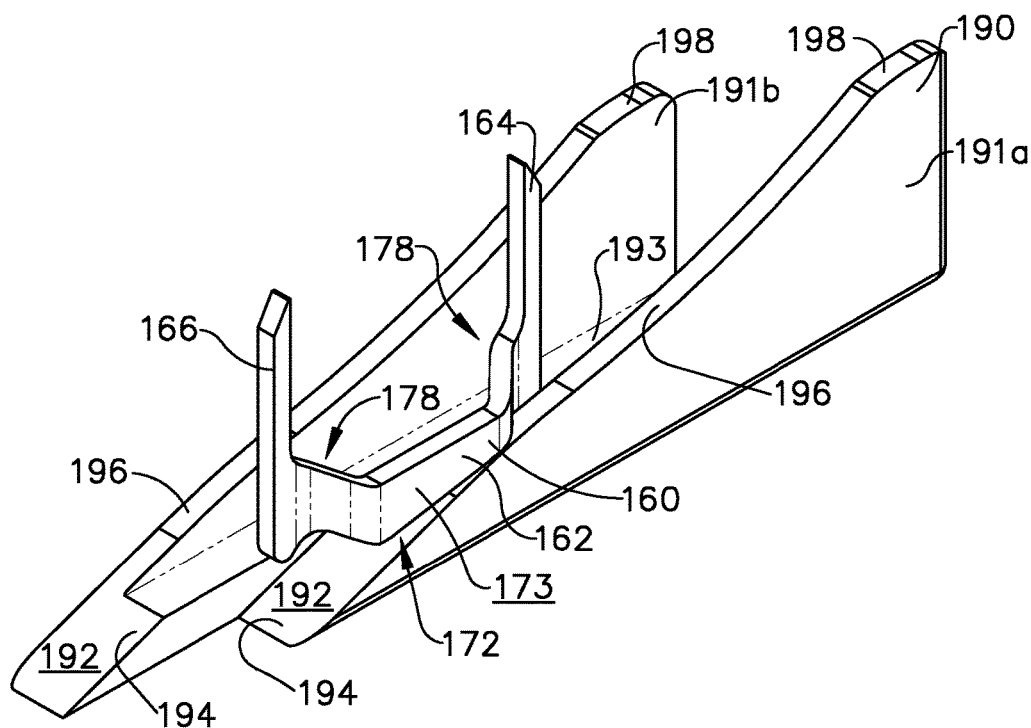
FIG. 17 is a perspective view of the staple and the sled of FIG. 14, depicting the trailing surface of the sled contacting the secondary drive surface of the staple.

Referring still to FIGS. 14-17, the sled 190 can include at least one lateral portion 191*a*, 191*b*. For example, the sled 190 can include a single lateral portion, a pair of lateral portions, and/or more than two lateral portions. In various instances, each lateral portion 191*a*, 191*b* can correspond to a row of staples 160 removably positioned in the cartridge body 142. As further depicted in FIGS. 14-17, the lateral portions 191*a*, 191*b* can be longitudinally staggered. For example, in certain embodiments, the first lateral portion 191*a* can lag behind or follow the second lateral portion 191*b* by a length of distance L (FIGS. 14 and 16). In other embodiments, the lateral portions 191*a*, 191*b* can be longitudinally aligned and/or the second lateral portion 191*b* can lag or follow the first lateral portion 191*a*, for example. In embodiments where the sled 190 comprises multiple lateral portions 191*a*, 191*b*, an intermediate portion 193 can connect and/or bridge the lateral portions 191*a*, 191*b*, for example.

Referring primarily to FIGS. 14-17, the sled 190 can transfer between the drive surfaces 180, 182 of the staple 160. Stated differently, the sled 190 can exert a driving force on the initial driving surface 180 of the staple 160, for example, and can then transition to exert a driving force on the second, or secondary, driving surface 182 of the staple 160. In certain embodiments, the sled ramp 192 can include a leading surface 194 and a trailing surface 196. The leading surface 194 can be adjacent to and/or connected to the trailing surface 196, for example, and the staple 160 can smoothly transition between the leading surface 194 and the trailing surface 196. For example, the leading surface 194 can contact the staple 160 and begin to lift the staple 160, and the trailing surface 196 can move into contact with the staple 160 and continue to lift the staple 160. In certain instances, the trailing surface 196 can smoothly lift the staple 160 out of and/or away from engagement with the leading surface 194, for example.

Referring still to FIGS. 14-17, the leading surface 194 can be aligned with the initial drive surface 180 and the trailing surface 196 can be aligned with the secondary drive surface 182, for example. In operation, the leading surface 194 of the ramp 192 can initially contact the staple 160. For example, referring to FIGS. 14 and 15, as the sled 190 translates, the leading surface 194 can contact the initial drive surface 180 of the staple 160. The inclined leading surface 194 can exert a driving force on the initial drive surface 180, which can begin to the lift the base 162 of the staple 160. For example, the staple 160 can be lifted a first distance or height by the leading surface 194. As the sled 190 continues to translate, referring now to FIGS. 16 and 17, the trailing surface 196 can move into contacting engagement with the secondary drive surface 182 of the staple 160, for example. The inclined trailing surface 196 can exert a driving force on the secondary drive surface 182, for example, which can continue to the lift the base 162 of the staple 160. For example, the staple 160 can be lifted a second distance or height by the trailing surface 194.

In various instances, the trailing surface 196 can lift the initial drive surface 180 away from and/or out of contact with the leading surface 194 of the ramp 192, for example. For example, the trailing surface 196 can contact the secondary drive surface 182 and immediately lift the staple 160 such that the primary drive surface 180 is moved out of driving contact with the leading surface 194. In other embodiments, the leading surface 194 can drive the initial drive surface 180 and the trailing surface 196 can drive the secondary drive surface simultaneously for at least a portion of the staple's deployment. As the sled 190 continues to translate, the trailing surface 196 can lift the base 162 out of the staple cavity 144 (FIGS. 4 and 5) and/or can eject the staple 160 from the cartridge 140 (FIGS. 4 and 5). For example, the proximal portion of the trailing surface 196 can include a sled overdrive 198. In various embodiments, the sled overdrive 198 can extend out of the staple cavity 144 and can lift the staple overdrive 188, i.e., the lowest portion of the intermediate portion 172 of the base 162 (see FIG. 7), out of the staple cavity 144.

Deployment of multiple staples 160 according to an exemplary application of the present disclosure is depicted in FIGS. 18-21. In certain embodiments, multiple rows of staple cavities 144 can be defined in the cartridge body 142. For example, multiple rows of staple cavities 144 can be defined on a first side of the cartridge slot 143 (FIG. 3), and multiple rows of staple cavities 144 can be defined on a second side of the cartridge slot 143. FIGS. 18-21 depict two rows of staples 160 positioned in two rows of staples cavities 144 in the cartridge body 142. Referring still to FIGS. 18-21, the staples 160*a*, 160*c*, and 160*e* can be positioned in a more inner row of staple cavities 144, for example, and the staples 160*b*, 160*d*, and 160*f* can be positioned in a more outer row of staple cavities 144, for example. In various embodiments, the first inner staple 160*a* can be positioned nearer to the cartridge slot 143 than the first outer staple 160*b*. For example, the first inner staple 160*a* can be adjacent to the cartridge slot 143, and the first outer staple 160*b* can be intermediate the first inner staple 160*a* and the side of the cartridge body 142, for example. In various embodiments, additional rows of staples 160 can be defined in the cartridge body 142. For example, at least one row of staples can be positioned intermediate the first staple 160*a* and the cartridge slot 143, and/or at least one row of staples 160 can be positioned intermediate the first outer staple 160*b* and the side of the cartridge body 142, for example.

Figure 18:
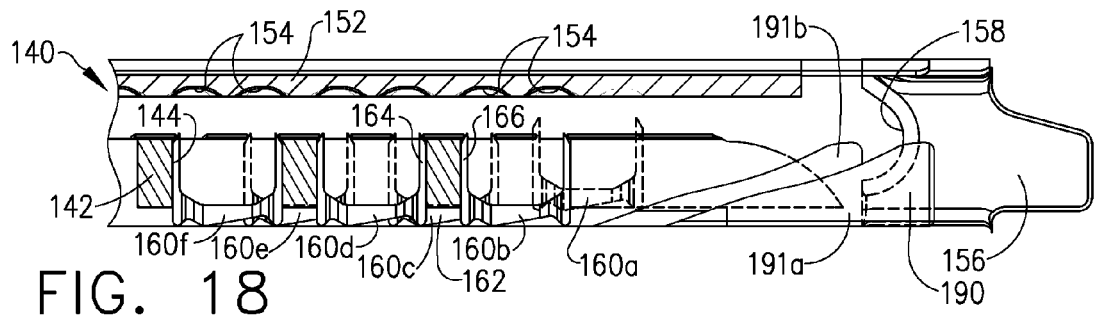
FIGS. 18-21 are cross-sectional elevation views of the end effector of FIG. 3, depicting a firing progression of staples from the staple cartridge, according to various embodiments of the present disclosure.
Figure 19:
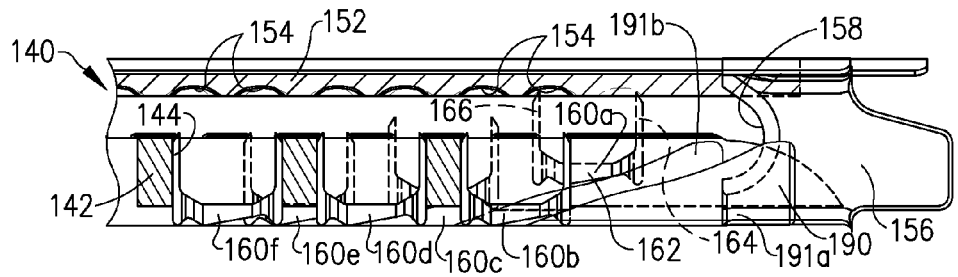

Referring primarily to FIG. 18, as the sled 190 moves distally, the second lateral portion 191b can contact the first inner staple 160a. The leading surface 194 (FIGS. 14-17) of the second lateral portion 191b can begin to lift the first inner staple 160a, for example. Referring now to FIG. 19, as the sled 190 continues to move distally, the trailing surface 196 (FIGS. 14-17) of the second lateral portion 191b can continue to lift the first inner staple 160a, and can move the first inner staple 160a into forming contact with the anvil 152 of the end effector 120, for example. Additionally, the leading surface 194 of the second lateral portion 191b can move into contact with the second inner staple 160c, for example. In various instances, the first lateral portion 191a can move into contact with the first outer staple 160b at the same time that the second lateral portion 191b moves into contact with the second inner staple 160c, for example. In certain embodiments, the longitudinal lag or offset between the first lateral portion 191a and the second lateral portion 191b can correspond to the longitudinal distance between the first outer staple 160b and the second inner staple 160c. For example, the first lateral portion 191a can lag behind the second lateral portion 191b a length L (FIGS. 14 and 16), and the first outer staple 160b can be longitudinally offset from the second inner staple 160c by the length L. In such embodiments, deployment of the first outer staple 160b and the second inner staple 160c can be simultaneous and/or synchronized, for example.

Figure 20:
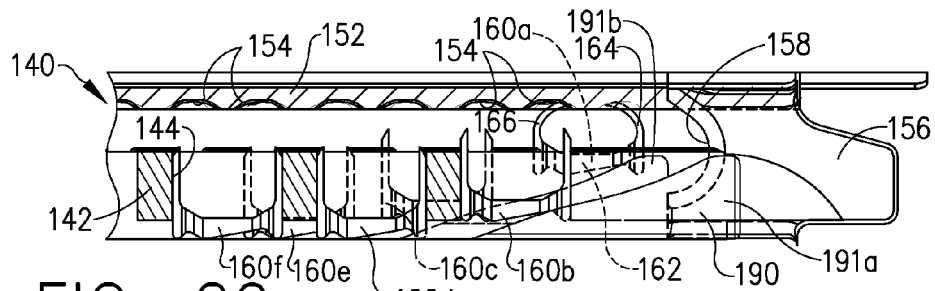
Figure 21:
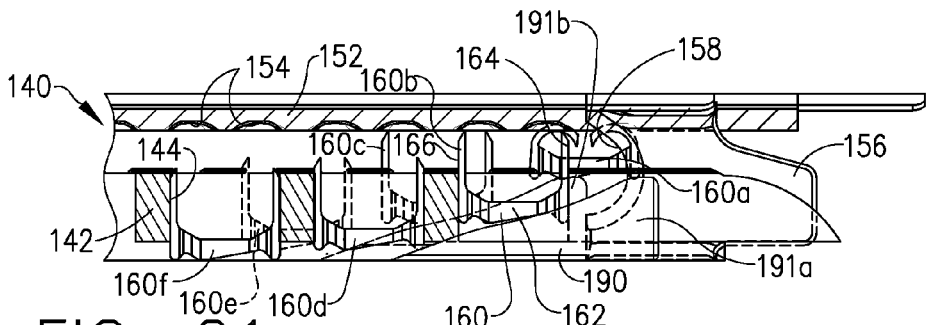

Referring now to FIG. 20, as the sled 190 continues to progress, the trailing surface 196 of the second lateral portion 191b can continue to lift the first inner staple 160a toward the anvil 152. The staple forming pockets 154 defined in the anvil 152 can catch the staple legs 164, 166, and can deform the first inner staple 160a. Furthermore, the second lateral portion 191b can continue to lift the second inner staple 160c, and the first lateral portion 191a can continue to lift the first outer staple 160b, for example. Referring now to FIG. 21, as the sled 190 continues to move distally, the second lateral portion 191b can eject the first inner staple 160a from the staple cavity 144. In various instances, the sled overdrive 198 (FIGS. 14-17), can lift the staple overdrive 188 to clear the staple base 162 over the cartridge body 142, for example. As the staple forming pockets 154 of the anvil 124 continue to form the first inner staple 160a, the second lateral portion 191b can continue to lift the second inner staple 160c, for example, and the first lateral portion 191a can continue to lift the first outer staple 160b. Additionally, the second lateral portion 191b can move into contact with the third inner staple 160e, for example, and the first lateral portion 191a can move into contact with the second outer staple 160d, for example. In various instances, similar to the above, the second outer staple 160d can be longitudinally offset from the third inner staple 160e by the length L (FIGS. 14 and 16).

As described herein, the staples 160 can be sequentially fired from the cartridge 140. For example, as the sled 190 moves distally, the sled 190 can sequentially fire staples 160 from a proximal portion of the cartridge body 142 toward a distal portion of the cartridge body 142. As described herein, the sled 190 can fire a first, more proximal, inner staple 160a before firing a second, more distal, inner staple 160c. In other embodiments, the sled 190 may translate proximally to fire staples 160 from a staple cartridge. In such embodiments, the sled 190 can sequentially fire staples 160 from a distal portion of the staple cartridge 140 toward a proximal portion of the staple cartridge 140. Moreover, firing of the staples 160 from the staple cartridge 140 can be paced or synchronized. For example, the first outer staple 160b and the second inner staple 160c can be fired simultaneously, and/or the second outer staple 160d and the third inner staple 160e can be fired simultaneously, for example. For example, the longitudinal offset between the first lateral portion 191a of the sled 190 and the second lateral portion 191b of the sled 190 can correspond to the longitudinal distance between a staple 160 in a first row of staple cavities and a staple 160 in a second, different row of staple cavities. In such embodiments, deployment of the staples 160 can be timed such that a staple 160 in the first row of staple cavities is fired at the same time as a staple 160 in the second row of staple cavities. The timing or pacing of staple deployment can improve tissue positioning and/or placement during firing. For example, sections of the tissue can be held in position by the end effector jaws 123, 124 (FIG. 3), and the sections can be stapled simultaneously. In other instances though, the offset between 191a and 191b may not be the same as the offset between the staples in the staple rows.

Figure 22:
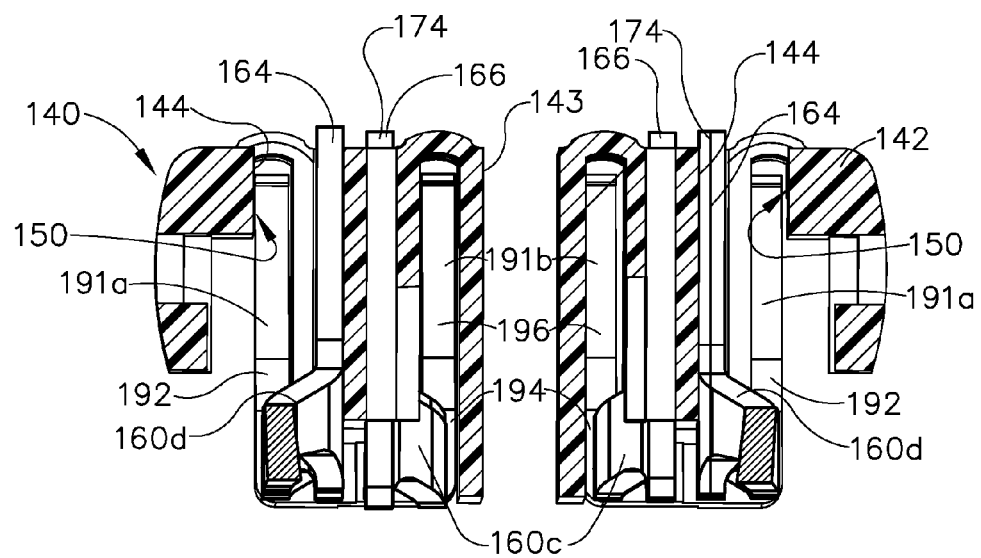
FIG. 22 is a cross-sectional elevation view of the staple cartridge and the sleds of FIG. 3, depicting the staples in unfired positions, according to various embodiments of the present disclosure.
Figure 23:
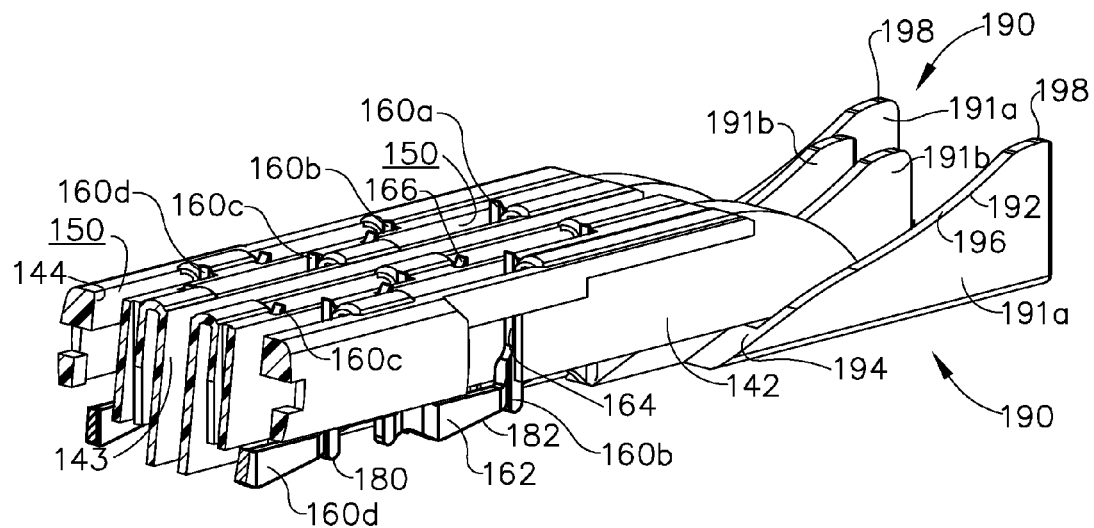
FIG. 23 is a cross-sectional perspective view of the cartridge and the sleds of FIG. 22, depicting the staples in the unfired positions depicted in FIG. 22.

An exemplary embodiment of staple deployment is further illustrated in FIGS. 22-31. For example, the staples 160a, 160b, 160c, and 160d can be positioned on both sides of the cartridge slot 140, and can be ejectably positioned in staple cavities 144 defined in the cartridge body 142. Referring primarily to FIGS. 22 and 23, the staples 160a, 160b, 160c, and 160d can be unfired, and the sleds 190 can be positioned proximal to the cartridge body 142. The sleds 190 can be aligned with the rows of staple cavities 144 in the cartridge body 142. For example, a first sled 190 can be aligned with the staples 160a, 160c in the first inner row of staple cavities 144 and with the staples 160b, 160d in the first outer row of staple cavities 144, and a second sled 190 can be aligned with the staples 160a, 160c in the second inner row of staple cavities 144 and with the staples 160b, 160d in the second outer row of staple cavities 144. The first lateral portions 191a of each sled 190 can be aligned with the outer staples 160b, 160d, and the second lateral portions 191b of each sled 190 can be aligned with the inner staples 160a, 160c, for example.

Figure 24:
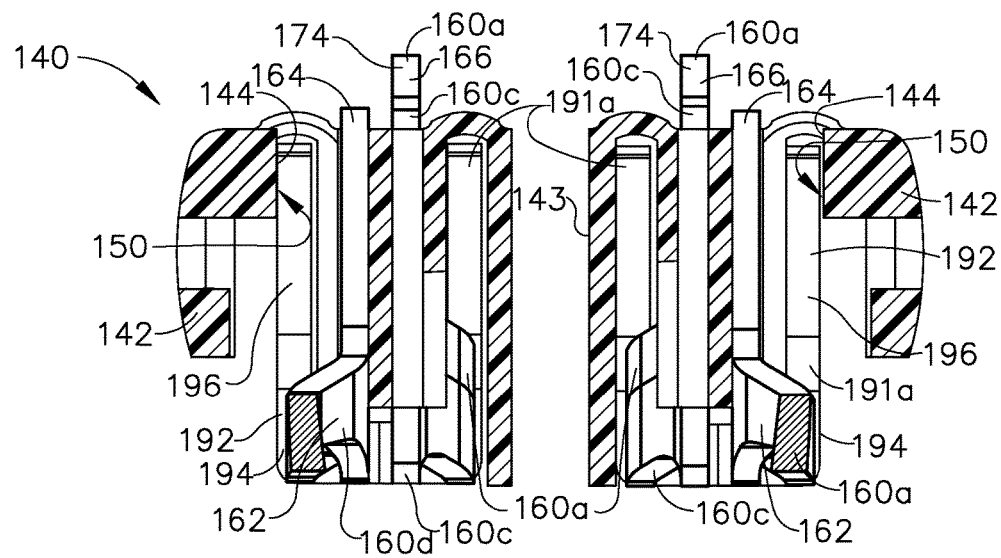
FIG. 24 is a cross-sectional elevation view of the cartridge and the sleds of FIG. 22, depicting a proximal pair of staples in partially fired positions and the remaining staples in unfired positions, according to various embodiments of the present disclosure.
Figure 25:
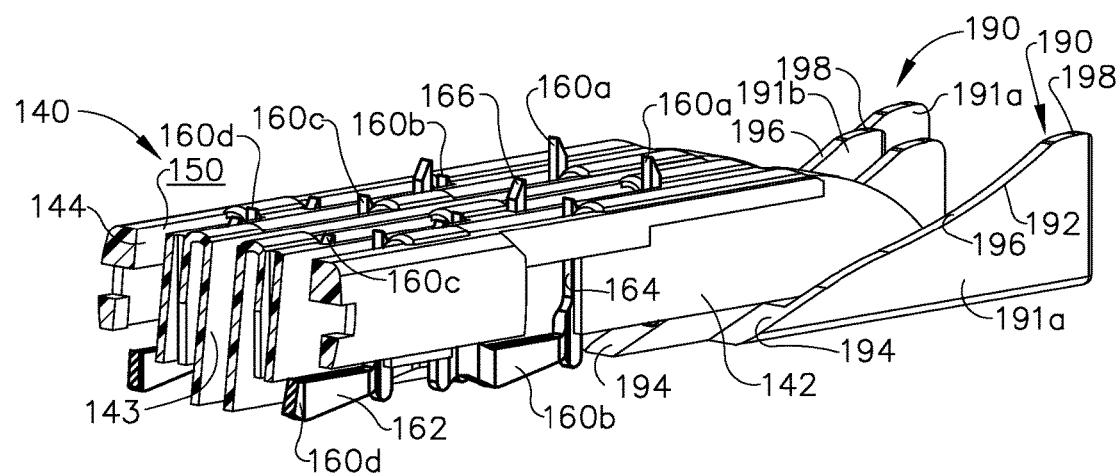
FIG. 25 is a cross-sectional perspective view of the cartridge and the sleds of FIG. 22, depicting the proximal pair of staples in the partially fired positions depicted in FIG. 24 and the remaining staples in the unfired positions depicted in FIG. 24.

Referring primarily to FIGS. 24 and 25, the first inner staples 160a can be moved or lifted to partially fired positions relative to the cartridge body 142. For example, the second lateral portions 191b of each sled 190 can move into engagement with the first inner staples 160a. The leading surfaces 194 of the second lateral portions 191b can lift the first inner staples 160a a first distance. Subsequently, the trailing surfaces 196 can move into engagement with the first inner staples 160a to further lift the first inner staples 160a. In various embodiments, distal translation of the sleds 190 can be coordinated, and the first inner staples 160a on each side of the slot 143 can be fired simultaneously, for example. As the first inner staples 160a are lifted, a portion of each staple 160a can slide or move against a longitudinal guide surface 150 of the staple cavity 144, and the longitudinal guide surface 150 can support and/or balance the torque generated by the sled 190, as described in greater detail herein.

Figure 26:
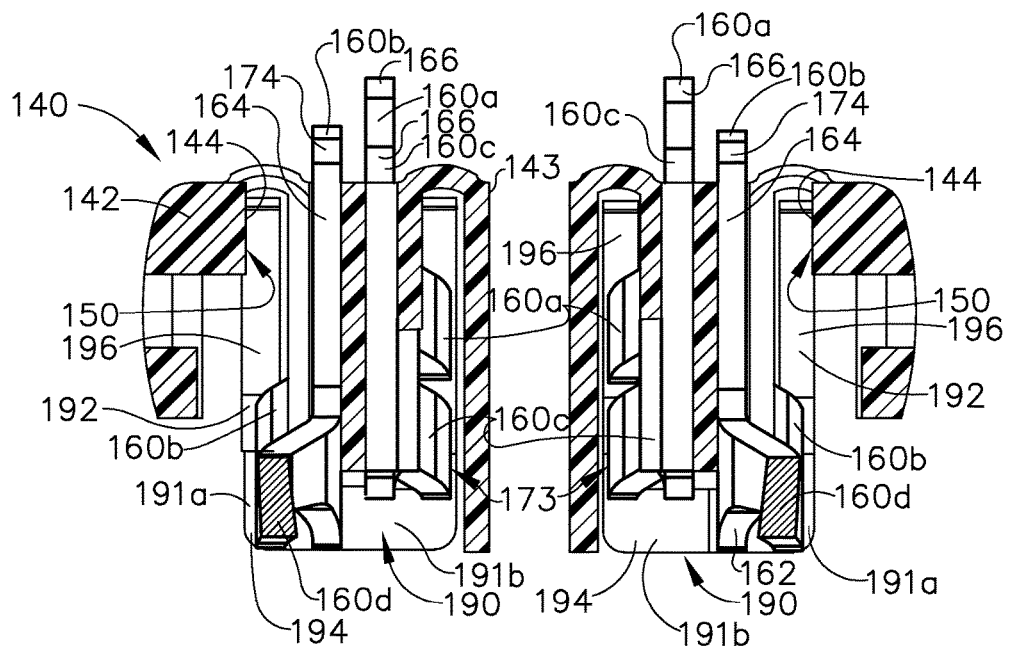
FIG. 26 is a cross-sectional elevation view of the cartridge and the sleds of FIG. 22, depicting multiple pairs of staples in partially fired positions and the proximal pair of staples in partially deformed configurations, according to various embodiments of the present disclosure.
Figure 27:
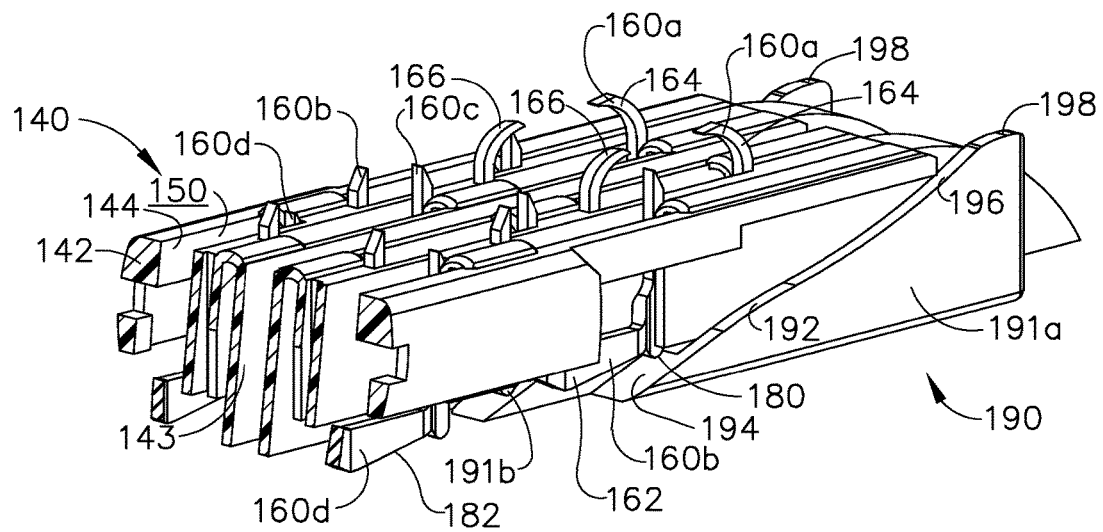
FIG. 27 is a cross-sectional perspective view of the cartridge and the sleds of FIG. 22, depicting the multiple pairs of staples in the partially fired positions of FIG. 26 and the proximal pair of staples in the partially deformed configurations depicted in FIG. 26.

Referring now to FIGS. 26 and 27, as the sleds 190 continue to translate relative to the cartridge 140, the sleds 190 can move into engagement with the first outer staples 160b and the second inner staples 160c. In various instances, the sleds 190 can contact the first outer staples 160b and the second inner staples 160c simultaneously. For example, the first lateral portions 191a of sleds 190 can contact the first outer staples 160b as the second lateral portions 191b of the sleds 190 contact the second inner staples 160c, for example. Referring primarily to FIG. 27, the leading surfaces 194 of the first lateral portions 191a and the second lateral portions 191b of the sleds 190 can engage the initial drive surfaces 180 of the staples 160b, 160c, and can lift the staples 160b, 160c relative to the cartridge body 142. Additionally, the trailing surfaces 196 of the second lateral portions 191b of the sleds 190 can continue to lift the first inner staples 160a, for example. As the first inner staples 160a continue to move out of the staple cavities 144, an anvil 152 (FIGS. 18-21) can begin to deform the first inner staples 160a. For example, staple forming pockets 154 (FIGS. 18-21) can catch, turn and/or bend the legs 164, 166 of the first inner staples 160a. As described herein, the anvil 152 can deform the staples 160a into modified "B-forms", for example.

Figure 28:
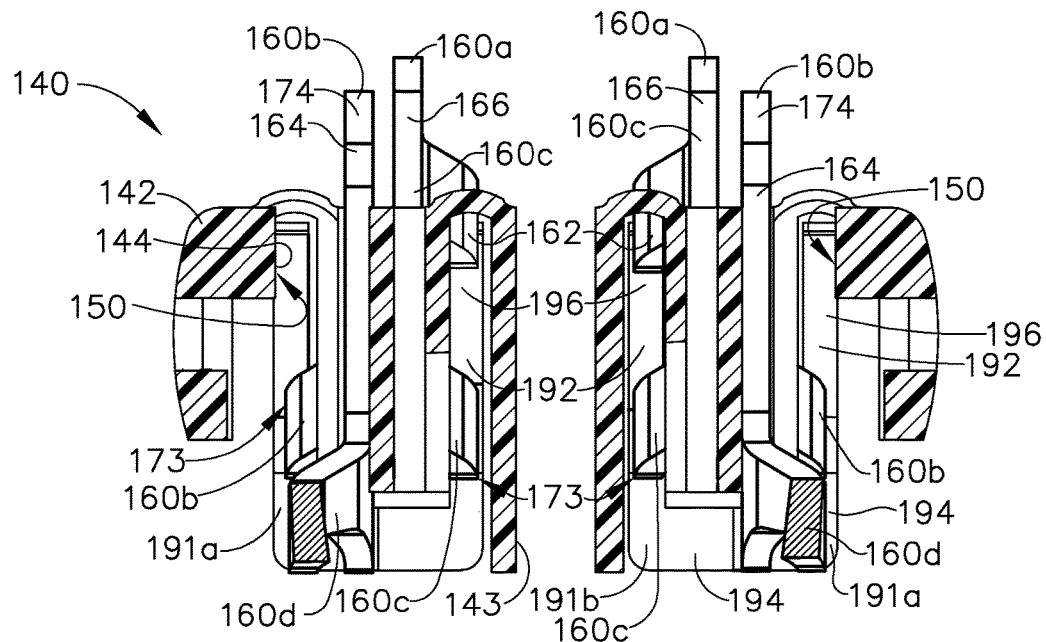
FIG. 28 is a cross-sectional elevation view of the cartridge and the sleds of FIG. 22, depicting multiple pairs of staples in further fired positions and the proximal pair of staples in further deformed configurations, according to various embodiments of the present disclosure.
Figure 29:
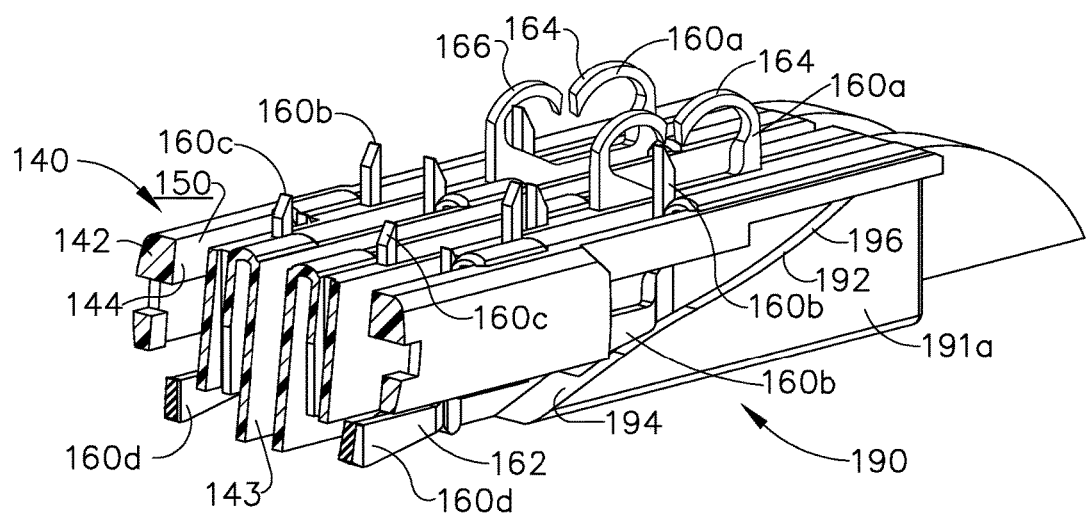
FIG. 29 is a cross-sectional perspective view of the cartridge and the sleds of FIG. 22, depicting the multiple pairs of staples in the partially fired positions depicted in FIG. 28 and the proximal pair of staples in the partially deformed configurations depicted in FIG. 28.

Referring now to FIGS. 28 and 29, as the sleds 190 continue to translate relative to the staple cartridge 140, the second lateral portions 191b of the sleds 190 can continue to lift the first inner staples 160a, for example, and the anvil 152 (FIGS. 18-21) can continue to deform the first inner staples 160a, for example. In various instances, the sleds 190 can also continue to lift the first outer staples 160b and the second inner staples 160c. For example, the trailing surfaces 196 of the sleds 190 can move into engagement with the secondary drive surfaces 182 of the first outer staples 160b and the second inner staples 160c, and can lift the staple bases 162 upward, for example, such that the staples legs 164, 166 continue to move out of the cartridge body 142.

Figure 30:
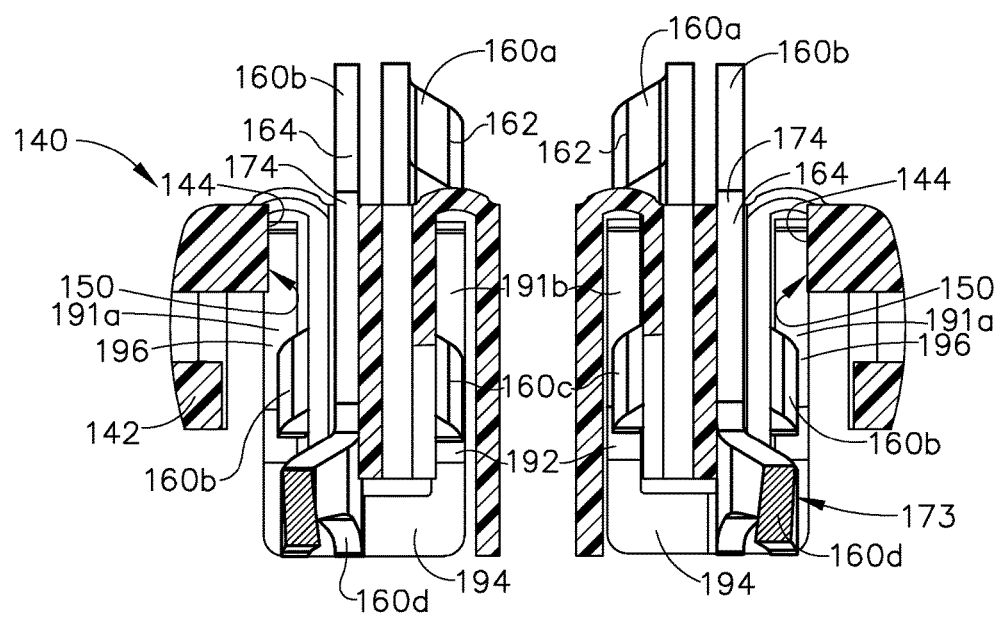
FIG. 30 is a cross-sectional elevation view of the cartridge and the sleds of FIG. 22, depicting multiple pairs of staples in partially fired positions and in partially deformed configurations and the proximal pair of staples in ejected positions and in fully deformed configurations, according to various embodiments of the present disclosure.
Figure 31:
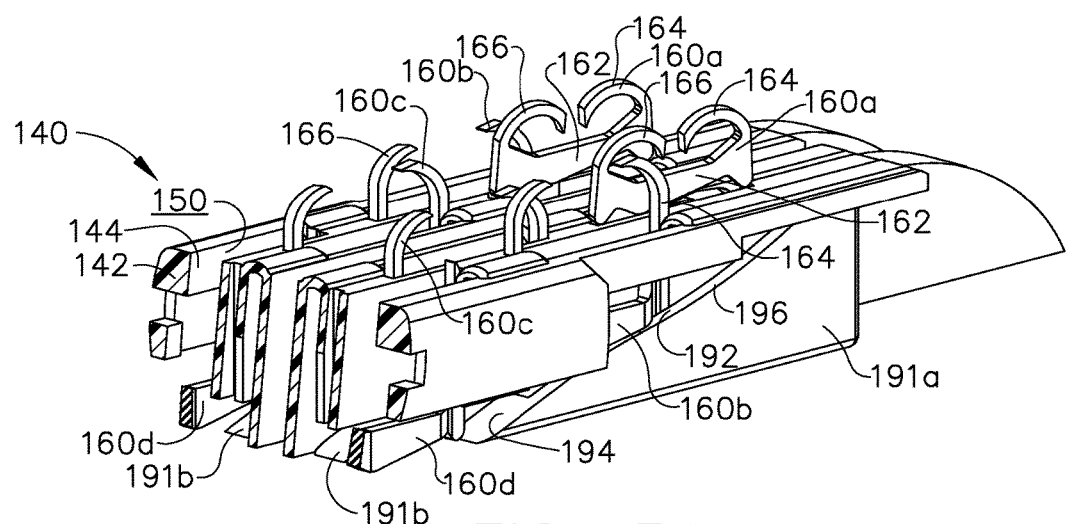
FIG. 31 is a cross-sectional perspective view of the cartridge and the sleds of FIG. 22, depicting the multiple pairs of staples in the partially fired positions and in the partially deformed configurations depicted in FIG. 30 and the proximal pair of staples in the ejected positions and in the fully deformed configurations depicted in FIG. 30.
Figure 34:
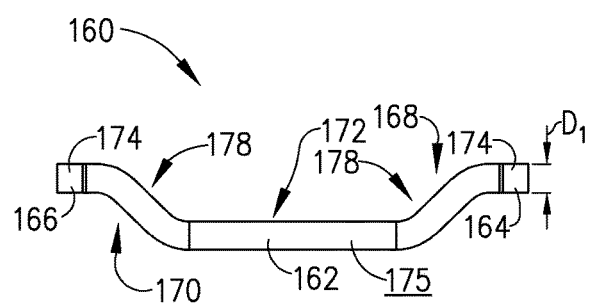
FIG. 34 is a plan view of the staple of FIG. 33.
Figure 33:
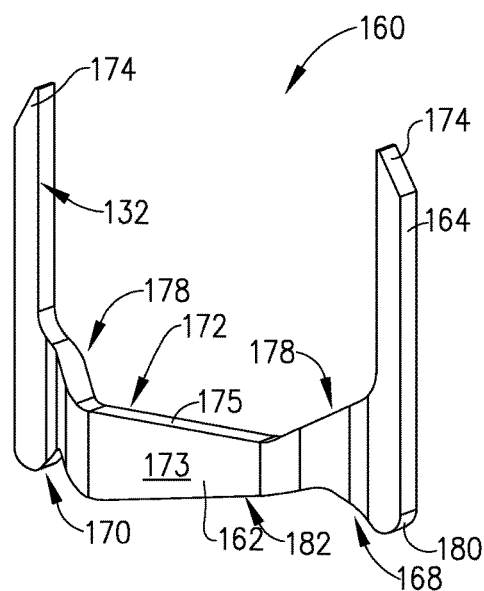
FIG. 33 is a perspective view of the staple formed from the method depicted in FIGS. 32A-32C, according to various embodiments of the present disclosure.
Figure 35:
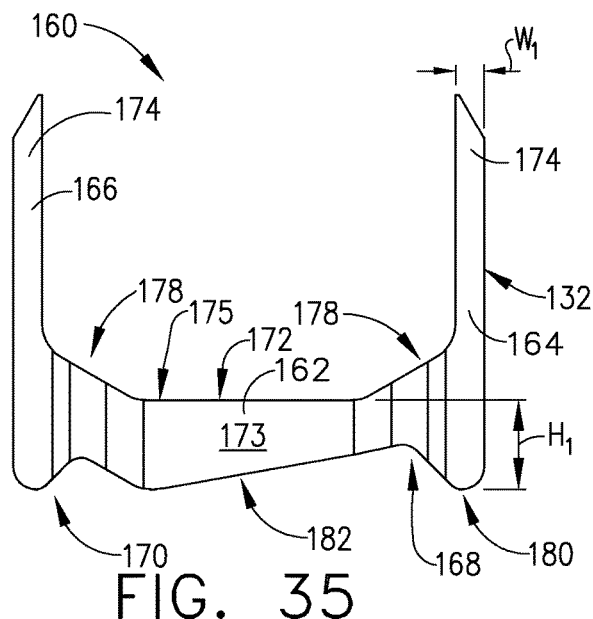
FIG. 35 is a front elevation view of the staple of FIG. 33.
Figure 36:
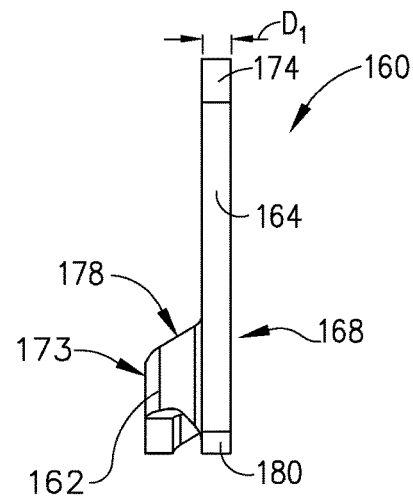
FIG. 36 is a side elevation view of the staple of FIG. 33.
Figure 38:
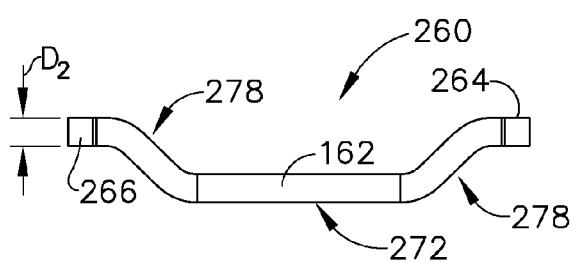
FIG. 38 is a plan view of the staple of FIG. 37.
Figure 37:
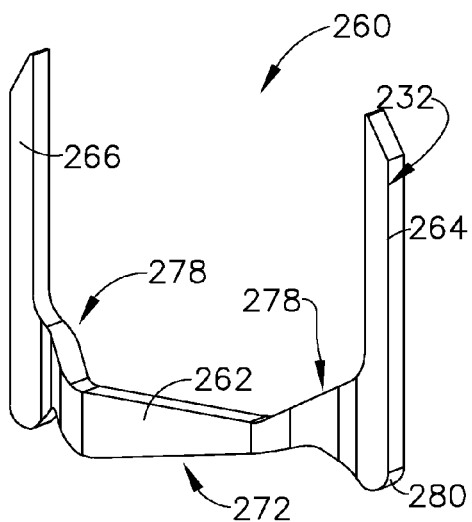
FIG. 37 is a perspective view of a staple according to various embodiments of the present disclosure.
Figure 39:
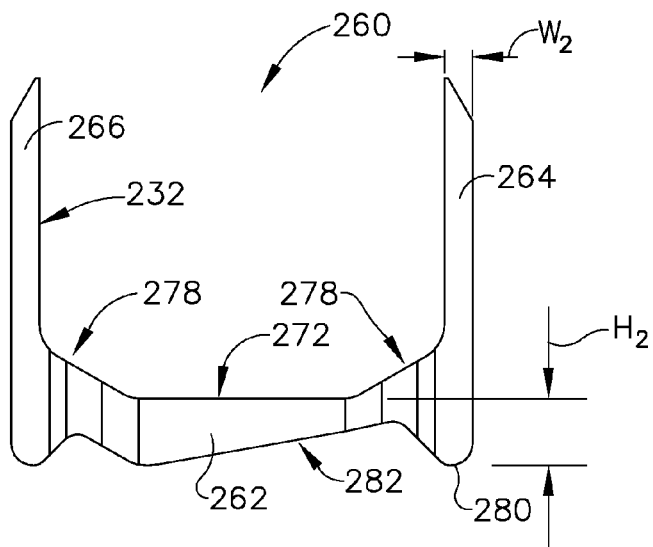
FIG. 39 is a front elevation view of the staple of FIG. 37.
Figure 40:
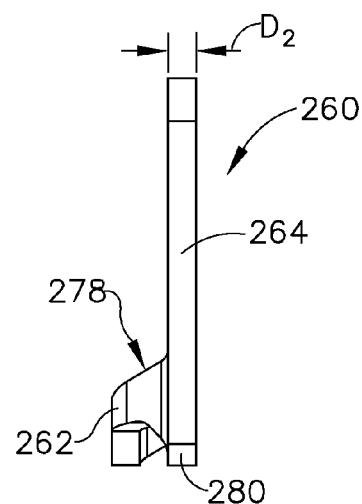
FIG. 40 is a side elevation view of the staple of FIG. 37.

Referring now to FIGS. 30 and 31, as the sleds 190 continue to translate relative to the cartridge 140, the second lateral portions 191b of the sleds 190 can continue to simultaneously lift the first inner staples 160a. For example, the sled overdrives 198 (FIGS. 16 and 17), can lift the first inner staples 160a entirely out of the cartridge body 142, such that the first inner staples 160a are entirely ejected from the staple cartridge 140. In various instances, the anvil 152 (FIGS. 18-21) can continue to deform the first inner staples 160a, for example, and the first inner staples 160a can be fully deformed when lifted entirely out of the cartridge body 142. Additionally, the trailing surfaces 196 of the sleds 190 can also continue to simultaneously lift the first outer staples 160b and the second inner staples 160c. For example, the trailing surfaces 196 of the first lateral portions 191a can lift or drive the first outer staples 160b, and the trailing surfaces 196 of the second lateral portions 191b can lift or drive the second inner staples 160c, for example. Moreover, as the first outer staples 160b and the second inner staples 160c continue to move out of the staple cavities 144, the anvil 152 (FIGS. 18-21) can begin to deform the first outer staples 160b and the second inner staples 160c. For example, staple forming pockets 154 (FIGS. 18-21) can catch, turn and/or bend the legs 164, 166 of the first outer staples 160b and the second inner staples 160c. In various instances, the sleds 190 can continue to translate relative to the cartridge body 142, and the first and second lateral portions 191a, 191b of the sleds 190 can continue to pace and/or time the deployment of the staples 160 from adjacent and/or neighboring staple rows. The sleds 190 can sequentially fire staples 160 from the proximal portion of the staple cartridge 140 to the distal portion of the staple cartridge 140. In other embodiments, the sleds 190 can move proximally, and can fire staples 160 from the distal portion of the staple cartridge 140 toward a proximal portion of the staple cartridge 140, for example. Moreover, in certain instances, the spacing between the staples and the lateral sled portions can affect non-synchronized deployment of the staples, for example.

Figure 56:
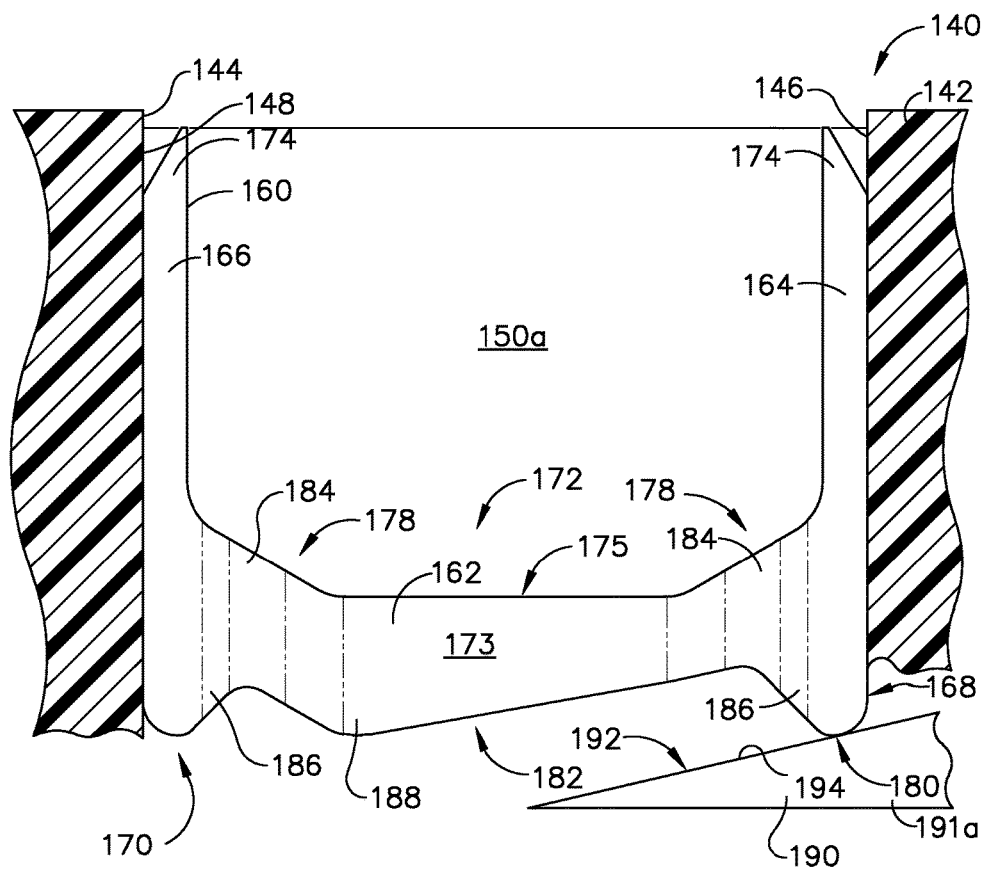
FIG. 56 is a partial, cross-sectional elevation view of the staple cartridge of FIG. 4, depicting a staple in a partially-fired position in a staple cavity, according to various embodiments of the present disclosure.
Figure 57:
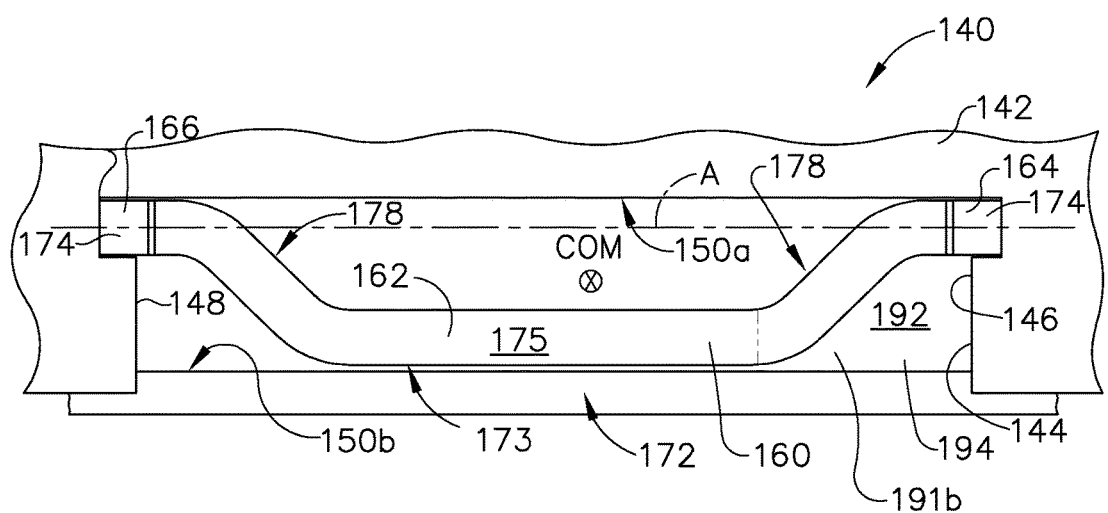
FIG. 57 is a partial plan view of the staple cartridge of FIG. 56, depicting the staple in the partially-fired position depicted in FIG. 56.
Figure 58:
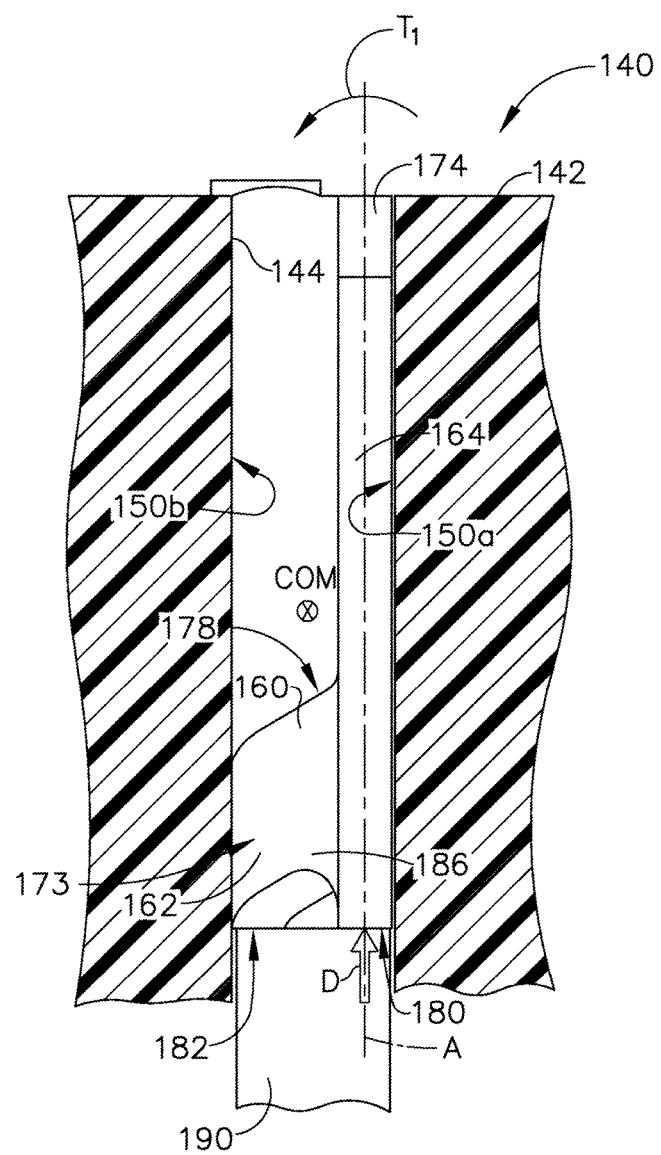
FIG. 58 is a partial, cross-sectional elevation view of the staple cartridge of FIG. 56, depicting the staple in the partially-fired position depicted in FIG. 56.

Referring now to FIGS. 56-64, in various instances, the staple cavity 144 can guide the staple 160 as the sled 190 moves the staple 160 through a firing progression. For example, in various instances, the leading surface 194 of the sled 190 can contact the initial drive surface 180 of the staple 160, and can exert a driving force $D_1$ (FIG. 58) on the staple 160 via the initial drive surface 180 (FIGS. 56-58). The leading surface 194 can lift the staple 160 upward along a plane defined by axis E (FIG. 57) and axis F (FIG. 58). As indicated in FIGS. 57 and 58, the staple's center of mass (COM) can be offset from the axes E and F and, in such embodiments, the driving force $D_1$ (FIG. 58) exerted on the initial drive surface 180 in the plane defined by axes E and F can generate a torque $T_1$ (FIG. 58). As described in greater detail herein, the staple cavity 144 can include a longitudinal sidewall 150 between the proximal end 146 and the distal end 148 of the staple cavity 144. In certain embodiments, the staple cavity 144 can include a first sidewall 150a and a second sidewall 150b. Moreover, as described herein, the sidewalls 150a, 150b can resist torsion of the staple 160 during firing. For example, when the leading surface 194 of the sled 190 drives the initial drive surface 180 of the staple 160 along the plane defined by axes E and F, the second sidewall 150b can resist the counterclockwise torque $T_1$ (FIG. 58) corresponding to the driving force $D_1$ generated by the sled 190. As the staple 160 is lifted a first distance by the leading surface 194 of the sled 190, the second sidewall 150b can guide and support the intermediate portion 172 of the staple base 162. For example, the flat surface 173 of the intermediate portion 172 of the staple base 162 can slide along and/or move against the second sidewall 150b.

Figure 59:
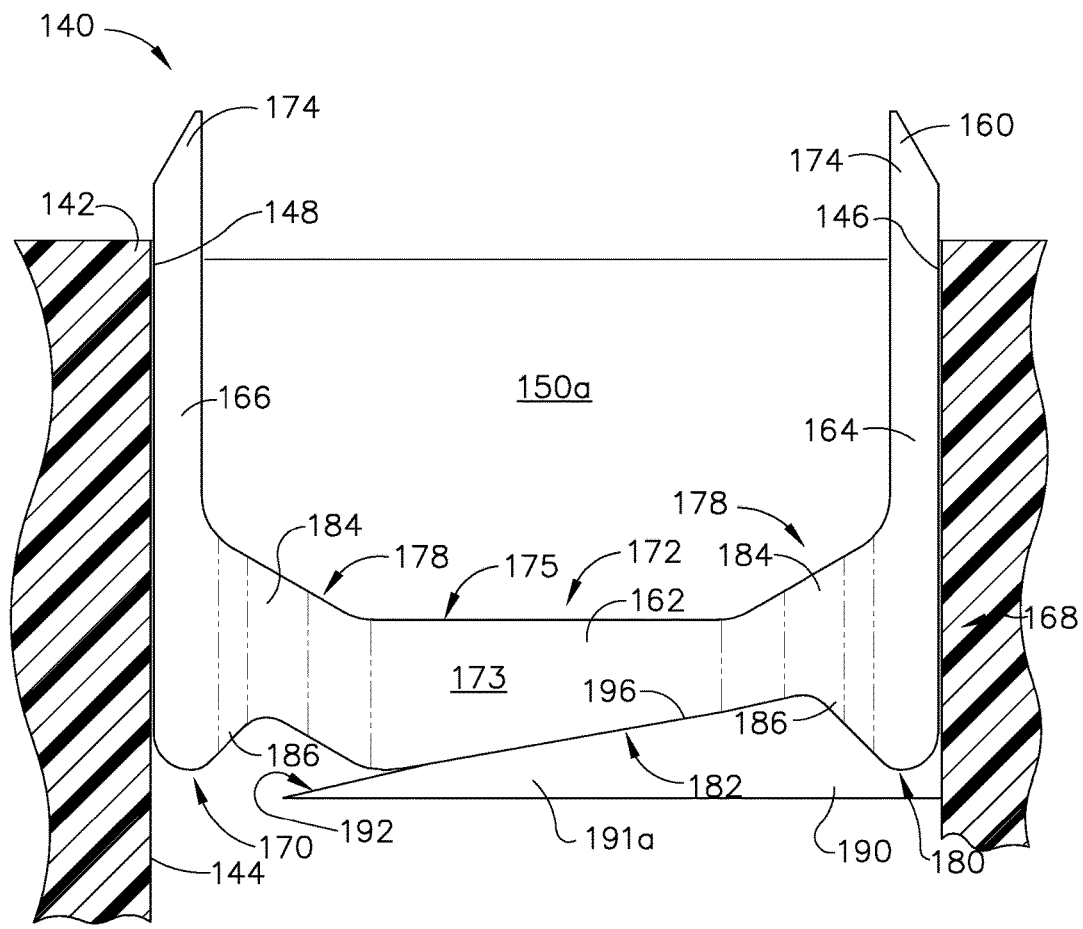
FIG. 59 is a partial, cross-sectional elevation view of the staple cartridge of FIG. 56, depicting the staple in another partially-fired position, according to various embodiments of the present disclosure.
Figure 60:
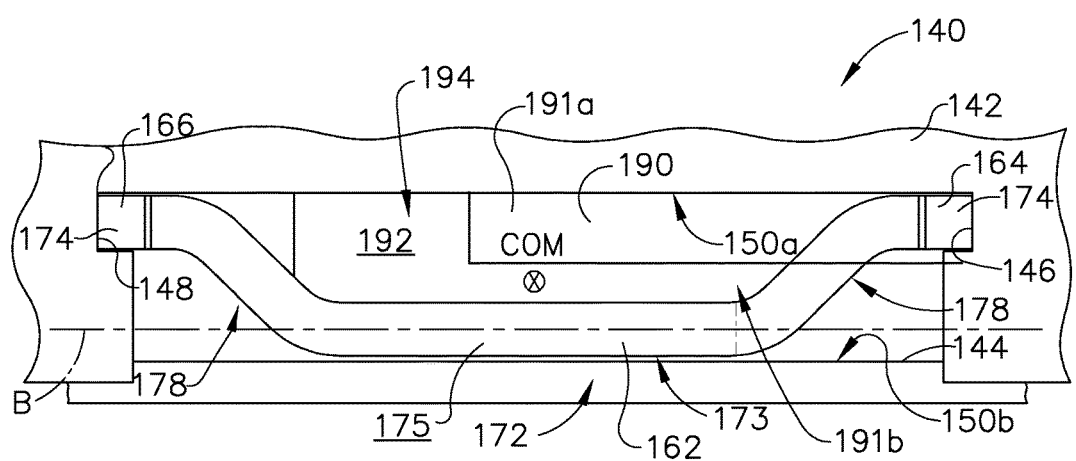
FIG. 60 is a partial, plan view of the staple cartridge of FIG. 56, depicting the staple in the partially-fired position depicted in FIG. 59.
Figure 61:
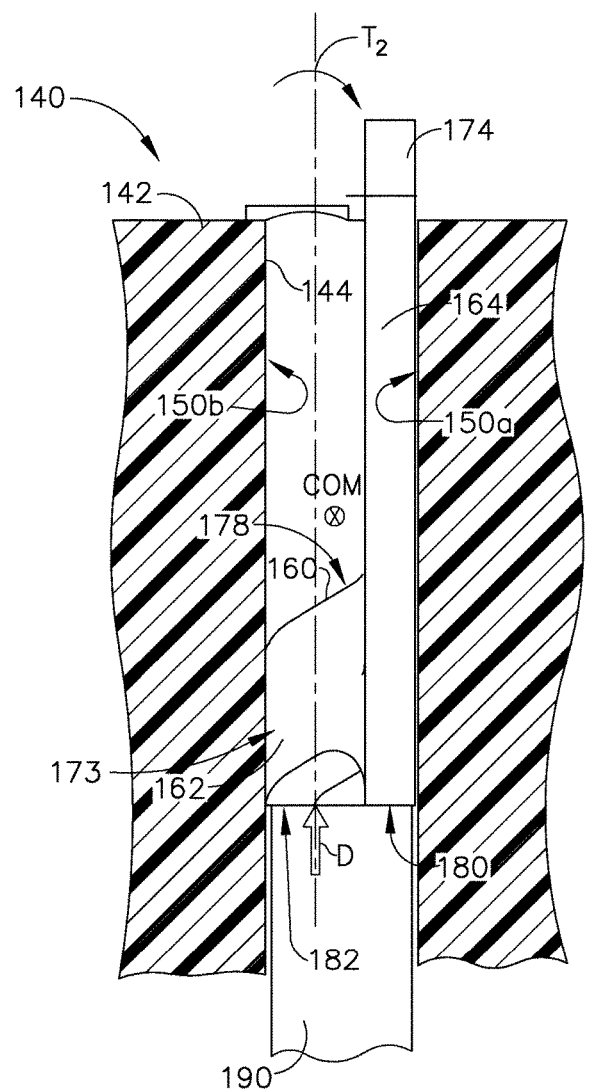
FIG. 61 is a partial, cross-sectional elevation view of the staple cartridge of FIG. 56, depicting the staple in the partially-fired position depicted in FIG. 59.

Referring now to FIGS. 59-61, when the sled 190 transitions between the initial drive surface 180 and the secondary drive surface 182, as described herein, the trailing surface 196 of the sled 190 can exert a driving force $D_2$ (FIG. 61) on the staple 160 via the secondary drive surface 182. In various instances, the trailing surface 196 of the sled 190 can lift the base 162 of the staple 160 upward along a plane defined by axis I (FIG. 60) and axis J (FIG. 61). As indicated in FIGS. 60 and 61, the staple's center of mass (COM) can be offset from the plane defined by axes I and J and, in such embodiments, the driving force $D_2$ (FIG. 61) exerted on the secondary drive surface 182 by the trailing surface 196 of the sled 190 can generate a torque $T_2$ (FIG. 61). Upon comparing FIGS. 58 and 61, it can be seen that the driving force $D_1$ is applied to the staple 160 on a first side of the COM and the driving force $D_2$ is applied on the opposite side of the COM. In various instances, the torque $T_1$ can be in a first direction, and the torque $T_2$ can be in second direction, and the second direction can be opposite to the first direction, for example. When the trailing surface 196 drives the secondary drive surface 182 of the staple 160 along the plane defined by axes I and J, the first sidewall 150a can resist the clockwise torque $T_2$ (FIG. 61). As the staple 160 is lifted the second distance by the trailing surface 194, the first sidewall 150a can guide and support the proximal and distal ends 168, 170 of the staple base 162. For example, the proximal and distal ends 168, 170 of the base 162 can slide along and/or move against the first sidewall 150a.

The reader will appreciate that, in certain embodiments, various staples and/or features thereof, which are described herein with respect to the staple's COM, can be similarly applicable to the staple's center of geometry. In various instances, a staple, such as staple 160, for example, can comprise a single material and/or can have a uniform composition. In such embodiments, the COM of the staple can correspond to the center of geometry of the staple. In other embodiments, a staple can comprise multiple materials and/or a non-uniform composition. For example, the staple can be formed from multiple pieces and/or materials that have been welded and/or otherwise joined together. In certain embodiments, multiple sheets of at least two different materials can be welded together, for example, and the staple can be cut from a portion of the welded sheet comprising more than one material. In other embodiments, multiple sheets of at least two different materials can be layered, rolled and/or sealed together, for example, and the staple can be cut from a portion of the sheet comprising more than one material. In such embodiments, the COM of the staple can be offset from the center of geometry of the staple. For example, the COM of the staple can be laterally and/or longitudinally offset from the staple's center of geometry.

Figure 62:
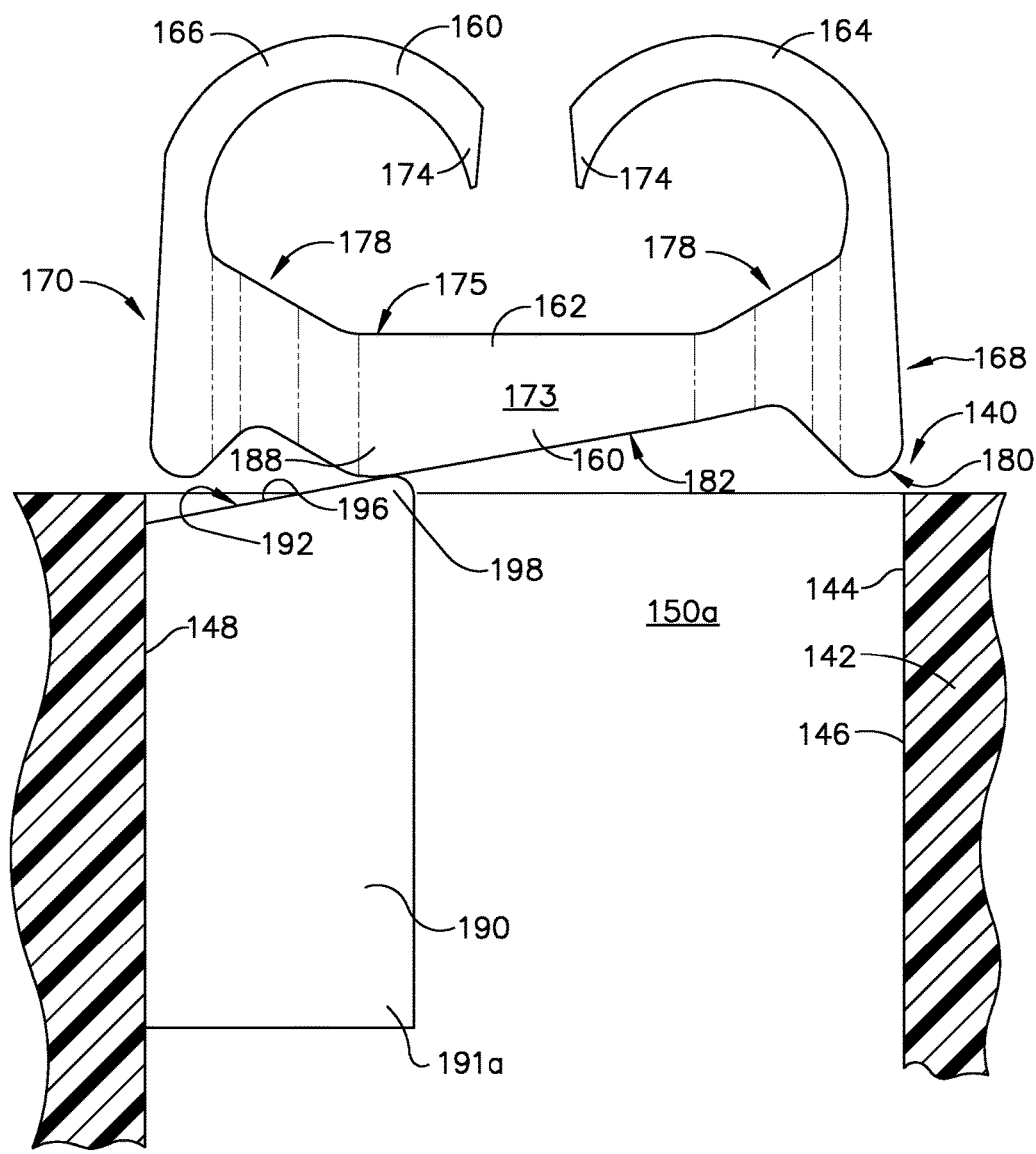
FIG. 62 is a partial, cross-sectional elevation view of the staple cartridge of FIG. 56, depicting the staple in an ejected position and in a deformed configuration, according to various embodiments of the present disclosure.
Figure 63:
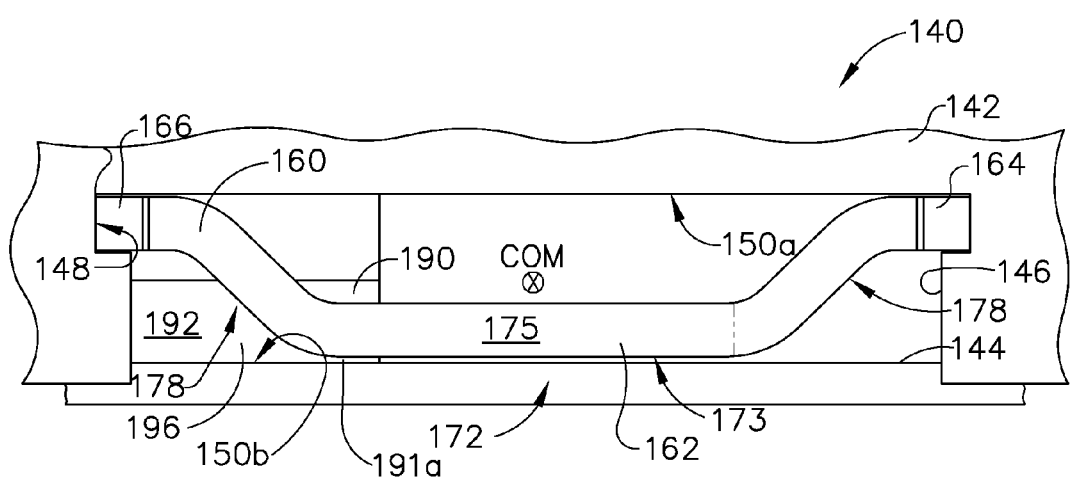
FIG. 63 is a partial plan view of the staple cartridge of FIG. 56, depicting the staple in the ejected position and in the deformed configuration depicted in FIG. 62.
Figure 64:
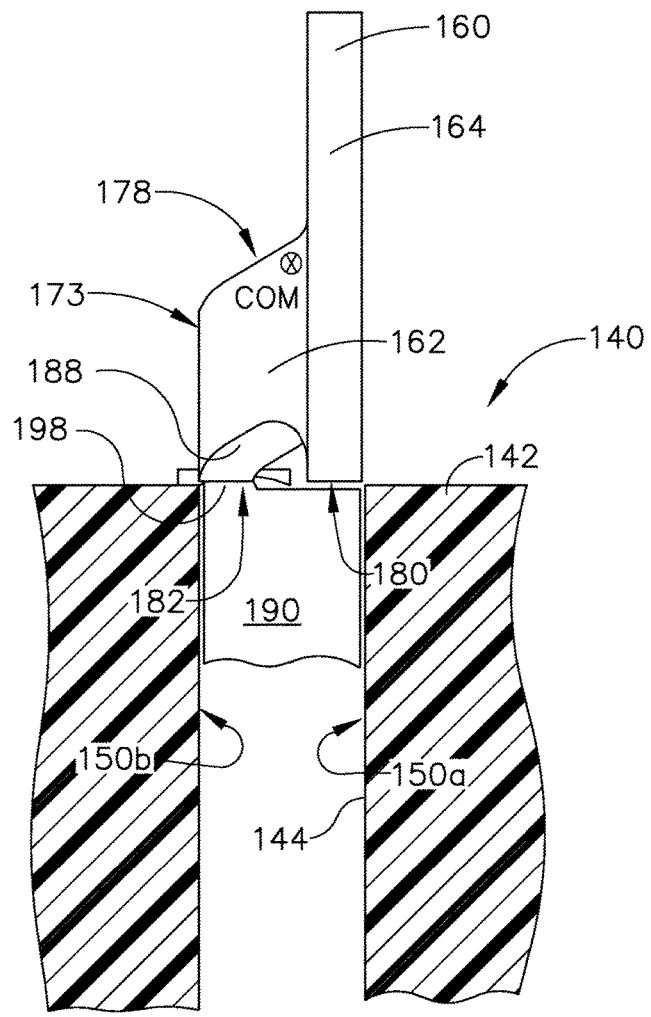
FIG. 64 is a partial, cross-sectional elevation view of the staple cartridge of FIG. 56, depicting the staple in the ejected position and the deformed configuration depicted in FIG. 62.

As depicted in FIGS. 58 and 61, the sled 190 can exert a vertical driving force $D_1$, $D_2$ on the staple 160 during deployment. The reader will appreciate that a driving force generated by the sled 190 can also comprise a horizontal component. In various embodiments, the proximal and/or distal ends 146, 148 of the staple cavity 144 can guide and support the staple legs 164, 166, as the staple 160 is lifted by the sled 190. In various embodiments, the proximal and/or distal ends 146, 148 of the staple cavity 144 can balance the torque generated by the horizontal component of the driving force. For example, as the sled 190 moves distally, the distal end 148 of the staple cavity 144 can resist rotation and/or torquing of the staple 160 during deployment. Referring now to FIGS. 62-64, the trailing surface 196 can continue to lift the staple 160 out of the staple cavity 144. For example, the sled overdrive 198 can contact the staple overdrive 188 to lift the base 162 of the staple 160 out of the cartridge body 140.

Figure 47:
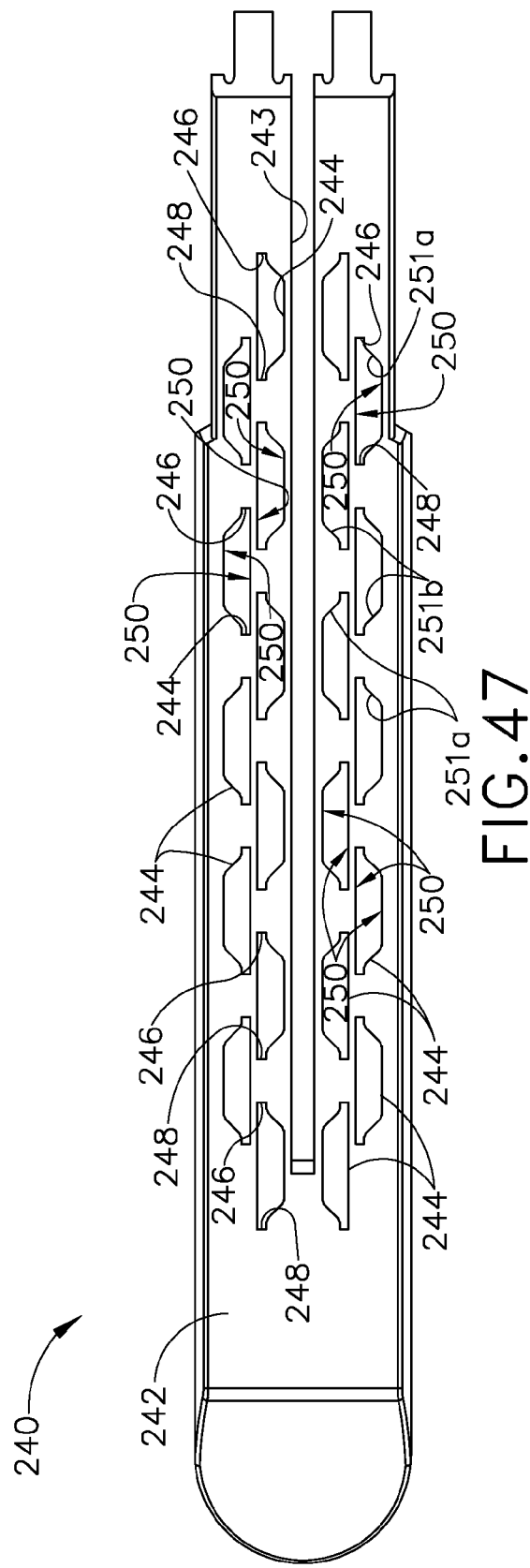
FIG. 47 is a plan view of the staple cartridge of FIG. 45.
Figure 49:
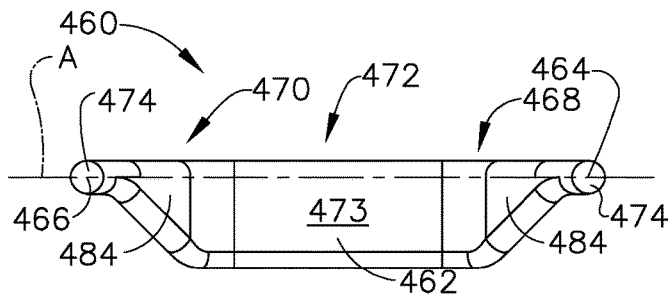
FIG. 49 is a plan view of the staple of FIG. 48.
Figure 48:
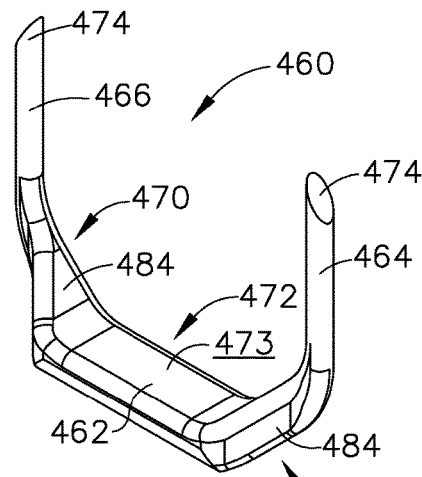
FIG. 48 is a perspective view of a staple according to various embodiments of the present disclosure.
Figure 50:
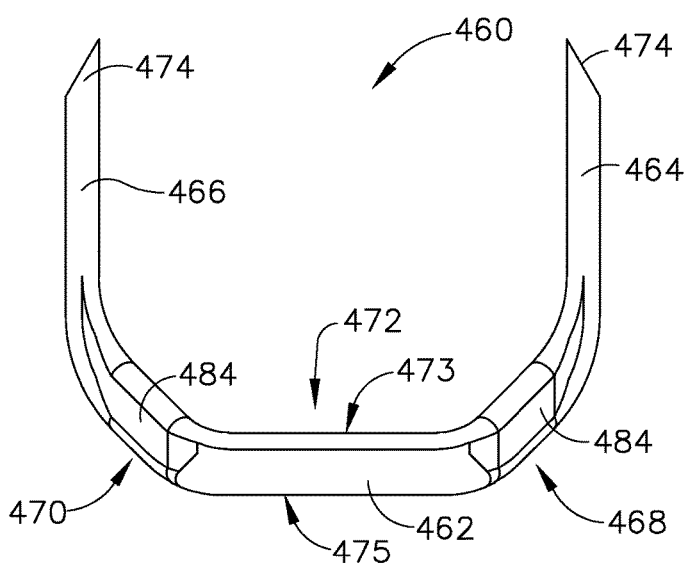
FIG. 50 is a front elevation view of the staple of FIG. 48.
Figure 51:
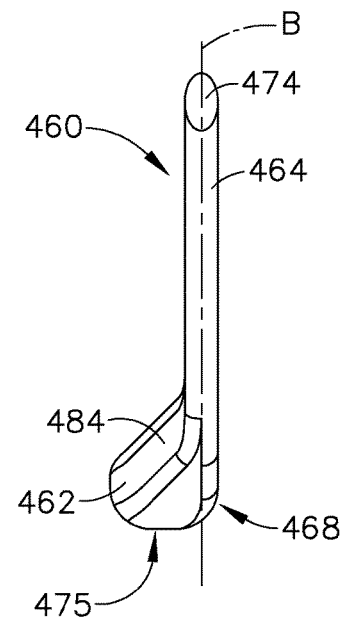
FIG. 51 is a side elevation view of the staple of FIG. 48.

Referring now to FIGS. 45-47, a staple cartridge, such as a staple cartridge 240, for example, can be loaded into the elongate channel 122 of the end effector 120 (FIG. 3). Staples, such as staples 160, for example, can be ejectably positioned in the staple cartridge 240. For example, sleds 190 (FIGS. 14-17) can translate through the staple cartridge 240 to eject the staples 160 therefrom. In various instances, the staple cartridge 240 can include a cartridge body 242 and cavities 244 defined in the cartridge body 242. Staples 160 can be removably positioned in the staple cavities 244, for example. For example, each staple cavity 244 can removably store a single staple 160. Moreover, each staple cavity 244 can have a proximal end 246 and a distal end 248, for example, and longitudinal sidewalls 250 can extend between the proximal end 246 and the distal end 248 of each staple cavity 244. Similar to the cavities 144 described herein, the proximal ends 246, distal ends 248, and/or longitudinal sidewalls 250 can guide and/or support the staples 160 during firing. For example, the longitudinal sidewalls 250 can counterbalance the torque exerted on the staple 160 by the translating sled 190. In various instances, the cavities 244 can also include diagonal guide surfaces 251 between the sidewalls 250. For example, a proximal diagonal guide surface 251a can extend between the proximal end 246 of the cavity 244 and a sidewall 250 of the cavity 244. Additionally or alternatively, a distal diagonal guide surface 251b can extend between the distal end 248 of the cavity 244 and a sidewall 250 of the cavity 244. The diagonal guide surfaces 251a, 251b can guide and/or support the contoured portions 178 (FIGS. 6-13) of the staple 160, for example, as the staple 160 is lifted within the staple cavity 244. For example, a portion of the contoured portion 178 can slide along and/or move against the diagonal guide surfaces 251a, 251b. In such an arrangement, the diagonal guide surfaces 251a, 251b can balance the torque exerted on the staple 160, for example.

Referring now to FIGS. 32A-32C, staples, such as the staples 160, for example, can be cut, formed and/or stamped from a sheet of material, such as a sheet of material 130, for example. The sheet of material 130 can be metallic, for example, and can comprise stainless steel and/or titanium, for example. In various instances, the sheet of material 130 can be substantially flat and/or smooth. Moreover, in certain instances, the sheet of material 130 can be bent, folded, contoured and/or crimped at various regions, such as a first region 134 and a second region 136, for example. The sheet of material 130 can be bent using a punch and/or stamp, for example. Flat or substantially flat portions 135a, 135b, and 135c of the sheet of material 130 can be positioned intermediate the regions 134, 136, for example. The first region 134 can be intermediate the flat portions 135a and 135b, for example, and the second region 136 can be intermediate the flat portions 135b and 135c, for example. In various instances, the flat portions 135a and 135c can be coplanar, for example, and/or the flat portion 135b can be parallel and/or substantially parallel to the flat portions 135a and/or 135c, for example. Referring primarily to FIG. 32A, multiple flat sheets 130a, 130b, 130c, 130d, 130e, 130f can be stacked, and then bent at the regions 134 and 136 simultaneously. In other embodiments, the sheets 130a, 130b, 130c, 130d, 130e, 130f can be individually bent, for example, and then stacked.

In various instances, the staples 160 can be cut, formed and/or stamped from the bent sheets 130. For example, referring primarily to FIG. 32B, a staple outline 132 can be traced, etched, and/or cut into the bent sheets 130. The staple outline 132 can be machined and/or laser cut into the bent sheets 130, for example. In various instances, an electron discharge machining (EDM) wire 138 can be used to cut the staple outline 132. Furthermore, in certain instances, multiple stacked sheets 130 can be cut simultaneously. In certain embodiments, referring primarily to FIG. 32C, the staple outline 132 can form the boundary or perimeter of the staple 160. For example, the staple outline 132 can form the staple 160 (FIGS. 6-13 and 33-36), and/or can form a staple having various similar features to the staple 160, for example. In various instances, multiple staple outlines 132 can be cut into the sheet of material 130, and multiple staples 160 can be formed from a single sheet of material 130. As illustrated in FIGS. 32B and 32C, the EDM wire 138 can pass through more than one sheet of material 130 at a time to cut more than one staple 160 at a time. While six sheets 130 are being simultaneously cut by the EDM wire 138, any suitable number of sheets 130 can be cut at the same time. For instance, a wire 138 can cut less than six sheets 130 at the same time or more than six sheets 130 at the same time.

For example, referring to FIGS. 32C and 33-36, the staple outline 132 can form the base 162 and/or the staple legs 164, 166, for example. Furthermore, the staple outline 132 can include at least one integrally-formed staple drive surface. For example, the staple outline 132 can include the initial drive surface 180 and/or the secondary drive surface 182. In other words, the initial drive surface 180 and/or the secondary drive surface 182 can be machined and/or formed at the time the staple 160 is cut from the sheet of material 130. In certain instances, the bent or contoured regions 134, 136 of the sheet 130 (FIGS. 32A and 32B) can form the contoured portions 178 of the staple 160. Moreover, the lateral flat portions 135a and 135c of the sheet 130 (FIGS. 32A and 32B) can correspond to the staple legs 164 and 166, and the intermediate flat portion 135b of the sheet 130 (FIGS. 32A and 32B) can correspond to the intermediate portion 172 of the base 162, for example.

In various instances, the depth $D_1$ (FIGS. 34 and 36) of the staple 160 can determined by the depth of the sheet of material 130. For example, the sheet of material 130 can be selected based on the depth thereof, and the staple 160 formed from that sheet of material 130 can have the same depth as the sheet of material 130. Furthermore, the height $H_1$ (FIG. 35), and width $W_1$ (FIG. 35) of the base 162 and the staple legs 164, 166 can be determined by the staple outline 132. In various instances, the staple outline 132 can provide variations in the height and/or width of the staple components along the length of each component. For example, the height $H_1$ of the base 162 and/or the width $W_1$ of the staple legs 164, 166 can vary along the length thereof. Furthermore, tapers, steps, and/or other variations can be defined by the staple outline 132, and thus, the geometry of the staple 160 can be selected and/or manipulated based on the purpose, application, and/or design of the staple 160 and/or the end effector 120 with which the staple 160 may be used.

Referring primarily to FIGS. 33-36, in various instances, the staple 160 can be cut such that the height $H_1$ of the base 162 is independent of and/or different than the depth $D_1$ of the staple legs 164, 166. For example, the depth $D_1$ of the staple legs 164, 166 can correspond to the depth of the sheet of material 130, and the base 162 can be cut to an appropriate height $H_1$, which can be independent of the depth of the sheet of material 130 and/or the corresponding leg depth $D_1$, for example The appropriate height $H_1$ can be based on the purpose, application, and/or design of the staples 160 and/or the end effector 120 (FIG. 3) with which the staple 160 may be used, for example. Furthermore, the height $H_1$ of the base 162 can also vary along the length thereof. For example, the height $H_1$ can vary at and/or near a drive surface of the staple 160, and/or at a gusset between one of the staple legs 164, 166 and the base 162, for example. The staple outline 132 can provide at least one taper and/or step along the length of the base 162, for example. The staple outline 132 can comprise a taper or ramp, for example, which can form the secondary drive surface 182 of the base 162. The degree of incline of the secondary drive surface 182 can be selected, designed and implemented via the staple outline 132. In certain embodiments, the height $H_1$ of the base 162 can be greater than the depth $D_1$ of the staple legs 164, 166. In other embodiments, the height $H_1$ of the base 162 can be equal to or less than the depth $D_1$ of the staple legs 164, 166. Comparatively, the geometry of a staple that is formed from a bent wire may be constrained and/or limited based on the dimensions of the initial wire. For example, in a wire-formed staple, the height of the staple base typically corresponds to the width of the staple legs, which typically corresponds to the diameter of the wire. Though drawing and/or rolling, for example, can modify the diameter of the wire, the volume of material limits and/or restrains the permissible modifications.

In various instances, the width $W_1$ of the staple legs 164, 166 can also be independent of the depth $D_1$ of the staple legs 164, 166 and the height $H_1$ of the base 162, for example. The staple legs 164, 166 can be cut to an appropriate width $W_1$ based on the application, purpose and/or design of the staple 160 and/or the end effector 120 (FIG. 3) with which the staple 160 may be used, for example. In certain embodiments, the staple legs 164, 166 can comprise different widths, for example, and/or the width of the staple legs 164, 166 can taper, step, or otherwise vary along the length thereof. For example, the staple legs 164, 166 can taper at the tips 174 to form a piercing edge or point.

Referring now to FIGS. 37-40, a staple outline 232 can be traced, cut, etched, and/or machined into the sheet of material 130 (FIGS. 32A and 32B), and a staple 260, similar to the staple 160 (FIGS. 33-36), for example, can be formed from the sheet of material 130. For example, the staple 260 can include a base 262 and staple legs 264, 266 extending from the base 262. In various embodiments, the staple 260 can include contoured portions 278, which can correspond to the bent and/or contoured regions 134, 136 of the sheet of material 130 (FIGS. 32A and 32B) from which the staple 260 was formed. In certain embodiments, the staple 260 can include an intermediate portion 272 between the contoured portions 278, for example. Moreover, at least one drive surface 280, 282 can be formed along the perimeter of the staple 260 via the staple outline 232.

Similar to the staple 160, the depth $D_1$ of the staples legs 264, 266 can correspond to the depth of the sheet of material 130. Furthermore, in various instances, the height $H_2$ of the staple base 262 can be independent of the depth $D_1$ of the staple legs 264, 266 and/or independent of the depth of the sheet of material 130. For example, as depicted in FIGS. 37-40, the height $H_2$ of the staple base 262 is less than the height $H_1$ of the staple base 162 (FIGS. 33-36), and the depth $D_2$ of the staples legs 264, 266 is equal to the depth $D_1$ of the staple legs 164, 166, for example. In various embodiments, the width $W_2$ of the staple legs 264, 266 can also be independent of the depth $D_2$ of the staple legs 264, 266. The height $H_1$ of the staple base 262 and the width $W_2$ of the staple legs 264, 266 can be selected based on the purpose, application, and/or design of the staple 260 and/or the end effector 120 (FIG. 3), for example.

Referring now to FIGS. 41-44, a staple outline 332 can be traced, cut, etched, and/or machined into the sheet of material 130 (FIGS. 32A and 32B), and a staple 360, similar to the staples 160 and 260 (FIGS. 33-40), for example, can be formed from the sheet of material 130. For example, the staple 360 can include a base 362 and staple legs 364, 366 extending from the base 362. In various embodiments, the staple 360 can include contoured portions 378, which can correspond to the bent and/or contoured regions 134, 136 of the sheet of material 130 (FIGS. 32A and 32B) from which the staple 360 was formed. In certain embodiments, the staple 360 can include an intermediate portion 372 between the contoured portions 378, for example. Moreover, at least one drive surface 380 and 382 can be formed along the perimeter of the staple 360 via the staple outline 332.

Similar to the staples 160 and 260, the depth $D_3$ of the staples legs 364, 366 can correspond to the depth of the sheet of material 130. Furthermore, in various instances, the height $H_3$ of the staple base 362 can be independent of the depth $D_3$ of the staple legs 364, 366 and/or independent of the depth of the sheet of material 130. For example, as depicted in FIGS. 41-44, the height $H_3$ of the staple base 362 is greater than the height $H_1$ of the staple base 162 (FIGS. 33-36) and greater than the height $H_2$ of the staple base 262 (FIGS. 37-40), and the depth $D_3$ of the staples legs 364, 366 is equal to the depth $D_1$ of the staple legs 164, 166 and equal to the depth $D_2$ of the staple legs 264, 266, for example. In various embodiments, the width $W_3$ of the staple legs 364, 366 can also be independent of the depth $D_3$ of the staple legs 364, 366. The height $H_3$ of the staple base 362 and the width $W_3$ of the staple legs 364, 366 can be selected based on the purpose, application, and/or design of the staple 360 and/or the end effector 120 (FIG. 3), for example.

Referring now to FIGS. 48-51, a staple, such as a staple 460, for example, can be used in a staple cartridge, such as the staple cartridge 140 (FIGS. 3-5) and/or the staple cartridge 240 (FIGS. 45-47), for example. The staple 460 can include a base 462 having a proximal portion 468 and a distal portion 470. An intermediate base portion 472 can be positioned between the proximal portion 468 and the distal portion 470, for example. As depicted in FIGS. 48-51, a first staple leg 464 can extend from the proximal portion 468 of the base 462, and a second staple leg 466 can extend from the distal portion 470 of the base. In various instances, the staple legs 464, 466 can be cylindrical or substantially cylindrical, for example, and can include a staple tip 474, which can be tapered and/or include a sharp edge or point for piercing tissue, for example. In other embodiments, the staple legs 464, 466 can include a rounded and/or polygonal perimeter, for example. The intermediate portion 472 of the staple base 462 can include a tissue-contacting surface 473, which can be flat or substantially flat, for example. In various instances, the staple 460 can be formed from a wire, for example, which can be bent, twisted, and/or otherwise manipulated to form the staple legs 464, 466 and/or the staple base 462, for example. In various embodiments, the diameter of the wire can define the width and depth of the staple legs 464, 466, for example. In some embodiments, the wire can be drawn and/or rolled to modify the dimensions of the staple 460. In certain instances, the intermediate portion 462 of the wire base 462 can be formed and/or flattened to form the tissue-contacting surface 473. In various instances, the base 462 can be flattened between two parallel or substantially parallel plates, for example, such that the tissue-contacting surface 473 and a bottom surface 475 of the base 462 are flat or substantially flat and/or parallel or substantially parallel. Modifications to the base 162 may be limited and/or constrained by the volume of material of the wire, for example.

Referring still to FIGS. 48-51, the staple 460 can include chamfers and/or gussets. For example, a chamfer 484 can extend between the first staple leg 464 and the base 462, and/or a chamfer 484 can extend between the second staple leg 466 and the base 462. In certain embodiments, the chamfers 484 can be asymmetrical relative to a longitudinal axis G (FIG. 49) extending between the first staple leg 464 and the second staple leg 466, and/or relative to a vertical axis H (FIG. 51) extending along the length of the staple legs 464, 466, for example. The chamfers 484 can extend away from the axis G and/or the axis H, for example, and thus, in certain embodiments, the intermediate portion 472 of the base 462 can be offset from the axis G and/or the axis H. For example, the center of mass of the base 462 can be offset from the plane defined by the axis G and the axis H. In various instances, the offset intermediate portion 472 of the base 462 can form a wide and/or flat surface for contacting captured tissue, which can provide a broad and/or smooth surface for applying and/or distributing pressure on the captured tissue. In such embodiments, tissue tearing and/or trauma within the staple 460 may be reduced and/or minimized. Moreover, similar to the staples 160, 260, and/or 360 described herein, the staple 460 can include a leg formation plane, e.g., the plane defined by the axis G and the axis H, which can be offset from the center of mass of the base 462 of the staple 460, for example.

Referring now to FIGS. 52-55, a staple, such as a staple 560, for example, can be used in a staple cartridge, such as the staple cartridge 140 (FIGS. 3-5) and/or the staple cartridge 240 (FIGS. 45-47), for example. The staple 560 can include a base 562 having a proximal portion 568 and a distal portion 570. An intermediate base portion 572 can be positioned between the proximal portion 568 and the distal portion 570, for example. As depicted in FIGS. 52-55, a first staple leg 564 can extend from the proximal portion 568 of the base 562, and a second staple leg 566 can extend from the distal portion 570 of the base 562. In certain embodiments, the intermediate portion 572 of the base 560 can extend along an axis D (FIG. 53), which can be parallel and/or substantially parallel to an axis C (FIG. 53) defined between the first staple leg 564 and the second staple leg 566, for example.

In various instances, the staple legs 564, 566 can be cylindrical or substantially cylindrical, for example, and can include a staple tip 574, which can be tapered and/or include a sharp edge or point for piercing tissue, for example. In various instances, the staple 560 can be formed from a wire. For example, a wire can be bent, twisted and/or otherwise manipulated to form the staple 560. Referring still to FIGS. 52-55, the wire can be manipulated at curves 579a, 579b, 579c, and/or 579d. For example, the staple base 562 can include angled portions 578, which can be angularly oriented relative to the intermediate portion 572 of the staple base 562 and/or relative to the axis C defined between the first and second staple legs 564, 566, for example. In various embodiments, the wire forming the staple 560 can curve at 579a between the first staple leg 564 and the angled portion 578a, curve at 579b between the angled portion 578a and the intermediate portion 572, curve at 579c between the intermediate portion 572 and the angled portion 578b, and/or curve at 579d between the angled portion 578b and second staple leg 566, for example. For example, the intermediate portion 572 of the base 562 can be laterally offset from the axis C (FIG. 53) extending between the first staple leg 564 and the second staple leg 566.

In various embodiments, the diameter of the wire can define the width and depth of the staple legs 564, 566 and/or the staple base 562, for example. In some embodiments, the wire and/or portions thereof can be drawn and/or rolled to modify the dimensions of the staple 560 and/or elements of the staple 560. Furthermore, the wire can have a rounded and/or polygonal perimeter. In certain embodiments, the wire can be cut at an angle to form the staple tips 574, for example. Similar to the staples 160, 260, 360 and/or 460 described herein, the staple 560 can include a leg formation plane, e.g., the plane defined by the axis C, which can be offset from the center of mass of the base 562 of the staple 560, for example.

Figure 65:
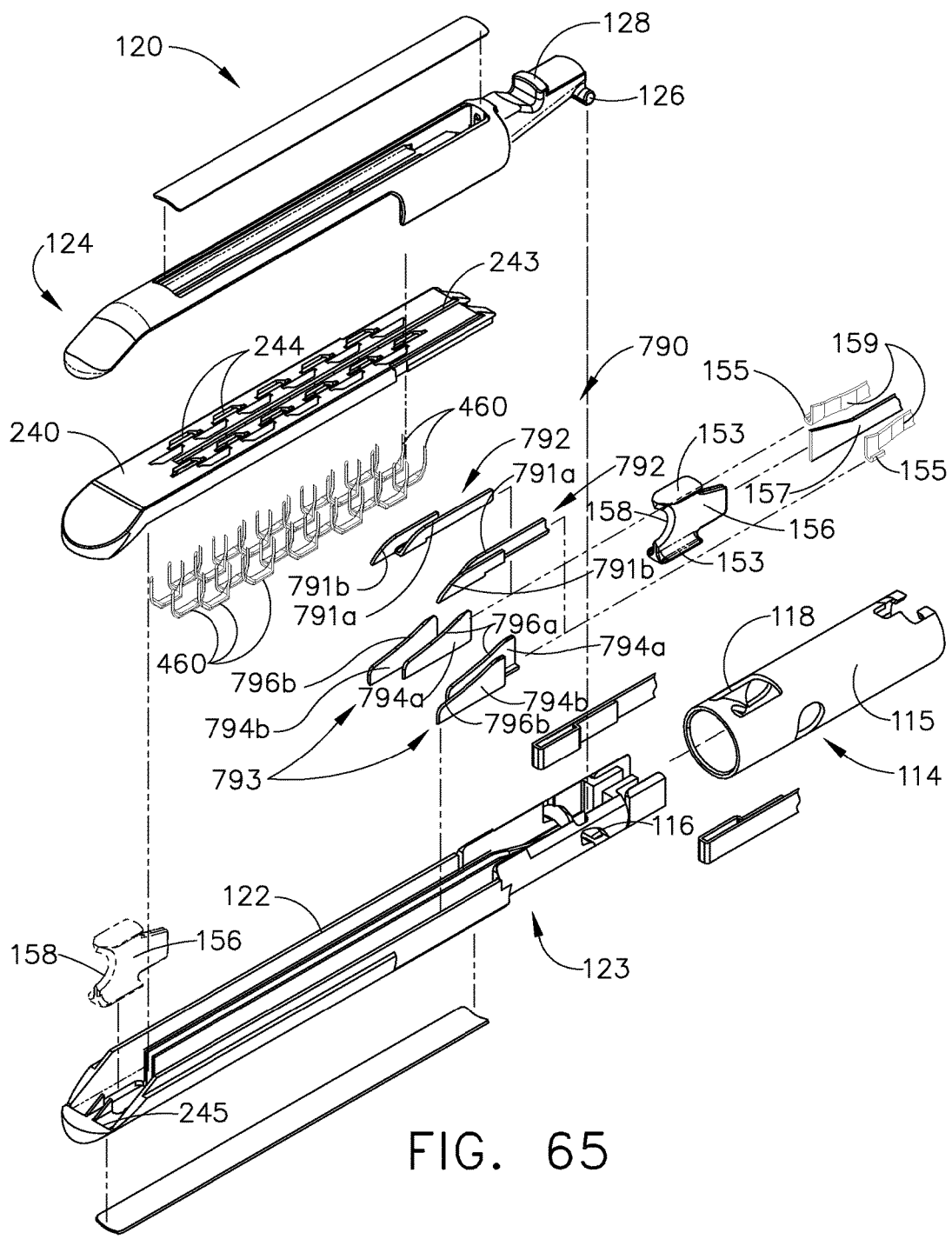
FIG. 65 is an exploded perspective view of an end effector comprising a plurality of fasteners and a firing actuator configured to eject the fasteners from the end effector according to various embodiments of the present disclosure.

Further to the above, turning now to FIG. 65, an end effector, such as end effector 120, for example, can include a staple cartridge 240 positioned within an elongate channel 122 and, in addition, an anvil 124 positionable opposite the staple cartridge 240. In various instances, the cartridge 240 can include a plurality of staple cavities 244, a fastener, such as staple 460, for example, positioned in each of the staple cavities 244, and a longitudinal slot 243 configured to slidably receive a knife 158 therein. While staples 460 are depicted in connection with the embodiment depicted in FIG. 65, any suitable staple or fastener could be used with this embodiment, such as staples 160, for example. Referring generally to FIGS. 73 and 74, the end effector 120 can extend from a shaft 114 which can include a closure tube 115. When the closure tube 115 is advanced distally, the closure tube 115 can contact the anvil 124 and rotate the anvil 124 between an open position (FIG. 73) and a closed position (FIG. 74). Once the anvil 124 has been closed, the knife 158 can be advanced distally to transect tissue captured between the anvil 124 and the cartridge 240. In certain end effectors disclosed herein, the cartridge positioned within the end effector 120 can further include a fastener firing actuator, such as sled 190, for example, which is pushed distally by the knife 158 to deploy staples from the cartridge at the same time that the knife 158 transects the tissue. With regard to the embodiment depicted in FIG. 65, a staple cartridge can include a fastener firing actuator, such as sled assembly 790, for example, which can be advanced distally with, or alongside, the knife 158 to eject the staples 460 from the cartridge 240. For instance, the shaft 114 of the stapler can include a firing bar 157 configured to advance the knife 158 and, in addition, pusher bars 159 configured to advance the sled assembly 790. While the firing bar 157 and the pusher bars 159 may be advanced concurrently, in various circumstances, their operation can be timed in such a way that their initial distal movement can be staggered relative to one another, as described in greater detail further below. In addition to the initial relative movement between the firing bar 157 and the pusher bars 159, the sled assembly 790 can include two or more portions which can move relative to one another, as will also be described in greater detail further below.

Figure 66:
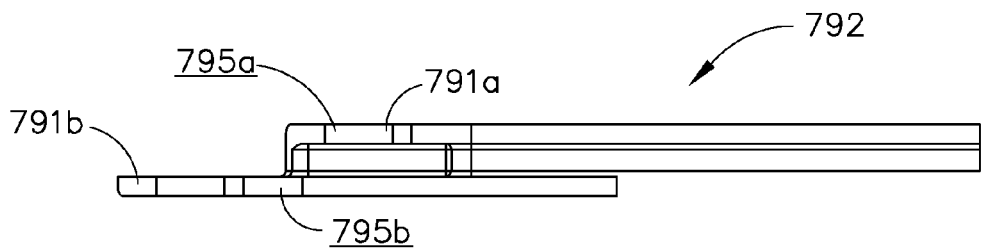
FIG. 66 is a plan view of a first portion of the fastener firing actuator of FIG. 65.
Figure 67:
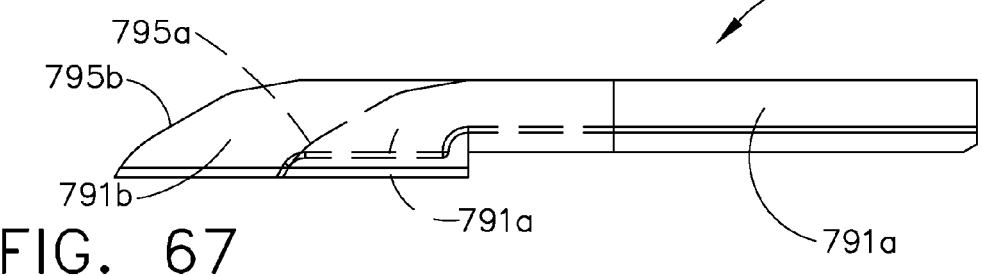
FIG. 67 is an elevational view of the first portion of FIG. 66.
Figure 68:
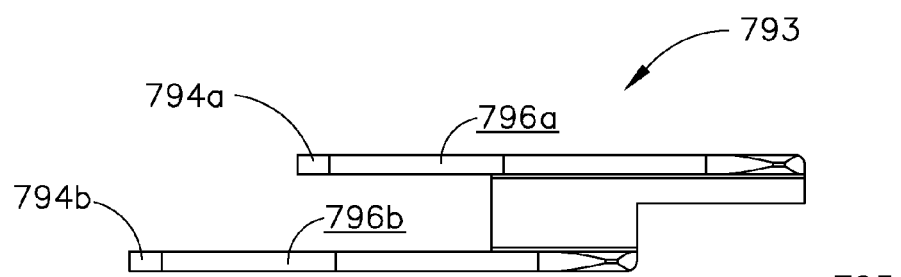
FIG. 68 is a plan view of a second portion of the fastener firing actuator of FIG. 65.
Figure 69:
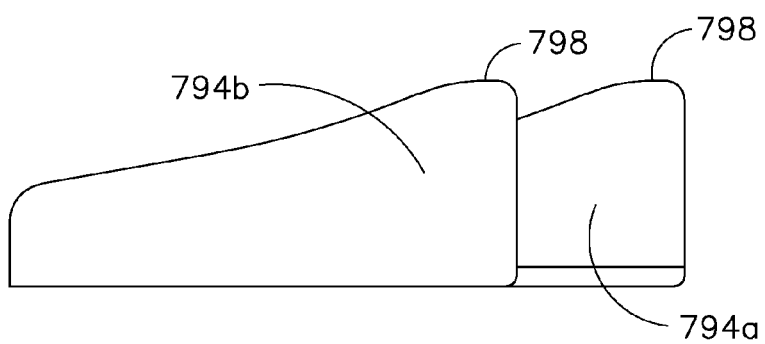
FIG. 69 is an elevational view of the second portion of FIG. 68.
Figure 75:
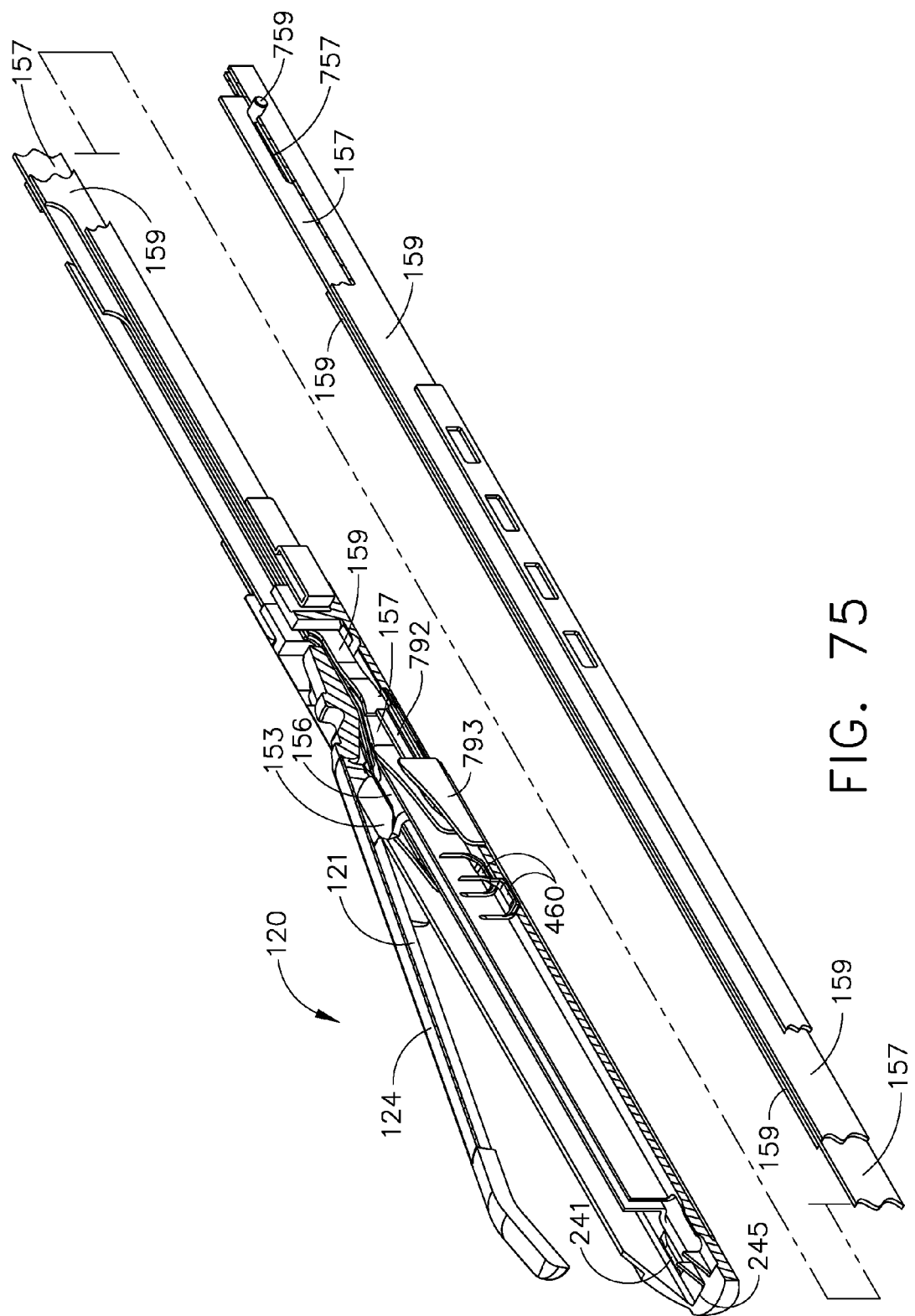
FIG. 75 is a cross-sectional perspective view of the end effector of FIG. 65 illustrated in the configuration depicted in FIG. 73.
Figure 76:
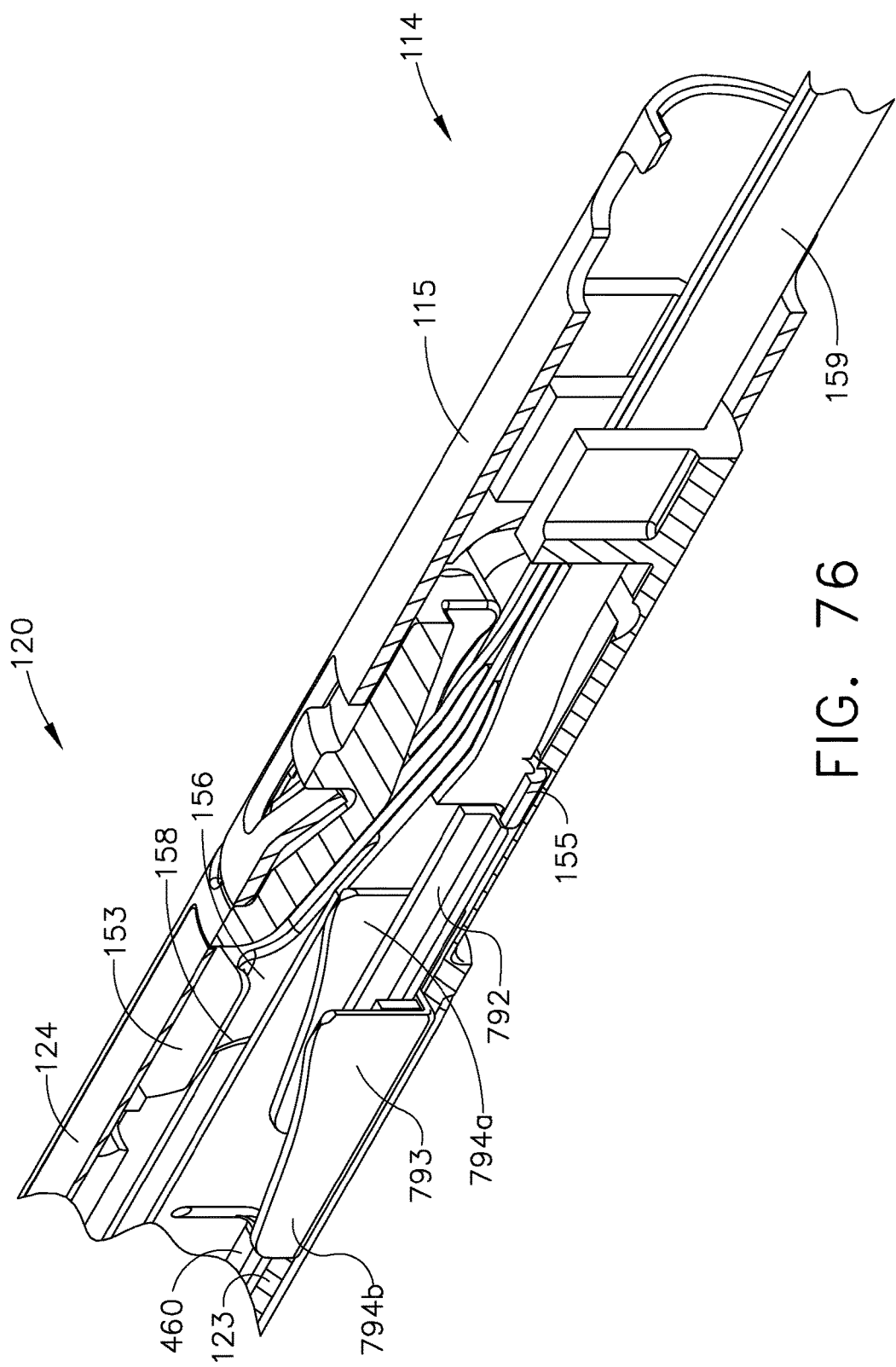
FIG. 76 is a cross-sectional view of the end effector of FIG. 65 illustrated in the configuration depicted in FIG. 74.

Referring primarily to FIGS. 66-69, the sled assembly 790 can include a first sled portion 792 and a second sled portion 793. The first sled portion 792 can include an inner ramp portion 791a and an outer ramp portion 791b. As illustrated in FIGS. 66 and 67, the outer ramp portion 791b is positioned laterally with respect to the inner ramp portion 791a. The outer ramp portion 791b also extends distally with respect to the inner ramp portion 791a. Similarly, the second sled portion 793 can include an inner ramp portion 794a and an outer ramp portion 794b. As illustrated in FIGS. 68 and 69, the outer ramp portion 794b is positioned laterally with respect to the inner ramp portion 794a. The outer ramp portion 794b also extends distally with respect to the inner ramp portion 794a. In various instances, the inner ramp portion 791a can be configured to lift, or at least partially lift, an inner row of staples while the outer ramp portion 791b can be configured to lift, or at least partially lift, an outer row of staples. As primarily depicted in FIG. 67, the inner ramp portion 791a and the outer ramp portion 791b can each include a ramp surface, such as ramp surfaces 795a and 795b, respectively, which can slide underneath the staples in the inner row of staples and the outer row of staples, respectively. The ramp surfaces 795a and 795b of the inner ramp portion 791a and the outer ramp portion 791b can be configured to lift staples from an unfired position to an at least partially-fired position. In various instances, the ramp surfaces 795a and 795b of the inner ramp portion 791a and the outer ramp portion 791b can each comprise at least one inclined surface, curved surface, actuate surface, and/or convex surface, for example.

Further to the above, the inner ramp portion 794a of the second sled portion 793 can include an inner ramp surface 796a and, similarly, the outer ramp portion 794b of the second sled portion 793 can include an outer ramp surface 796b. In various instances, the inner ramp surface 795a of the first sled portion 792 can be configured to co-operate with the inner ramp surface 796a of the second sled portion 793 to lift the staples in the inner row of staples from their unfired positions and their fully-fired positions. More particularly, the inner ramp portion 791a can lift the staples in the inner row of staples from an unfired position to a partially-fired position wherein the inner ramp portion 794a can then lift the staples from their partially-fired positions to a fully-fired position, for instance. In such circumstances, the lifting motion of the staples in the inner row of staples can be initiated by the inner ramp portion 791a of the first sled portion 792, transferred to the inner ramp surface 796a of the second ramp portion 793, and then completed by the second ramp portion 793. Similarly, the outer ramp surface 795b of the first sled portion 792 can be configured to co-operate with the outer ramp surface 796b of the second sled portion 793 to lift the staples in the outer row of staples from their unfired positions and their fully-fired positions. More particularly, the outer ramp portion 791b can lift the staples in the outer row of staples from an unfired position to a partially-fired position wherein the outer ramp portion 794b can then lift the staples from their partially-fired positions to a fully-fired position, for instance. In such circumstances, the lifting motion of the staples in the outer row of staples can be initiated by the outer ramp portion 791b of the first sled portion 792, transferred to the outer ramp surface 796b of the second ramp portion 793, and then completed by the second ramp portion 793. The firing, or lifting, motion of the staples in the inner row of staples can be completed once the apex 798 of the inner ramp portion 794a has passed underneath the staples. Similarly, the firing, or lifting, motion of the staples in the outer row of staples can be completed once the apex 798 of the outer ramp portion 794b has passed underneath the staples.

Referring again to FIG. 65, the sled assembly 790 can include more than one first sled portion 792 and/or more than one second sled portion 793. In various instances, the sled assembly 790 can comprise a first set of sled portions comprising a first sled portion 792 and a second sled portion 793 and a second set of sled portions comprising a first sled portion 792 and a second sled portion 793. In certain instances, the second set of sled portions can constitute a mirror image of the first set. For the purposes of simplifying the description of the sled assembly 790 herein, reference may be made to only one set of sled portions; however, the reader should appreciate that the description regarding the operation of one set of sled portions could also apply to the concurrent operation of any suitable number sets of sled portions.

Further to the above, the outer staple rows of the cartridge 240, i.e., the rows furthest away from the channel 243, can lead the inner staple rows, i.e., the rows closest to the channel 243. Stated another way, the deformation of the staples in the outer row can begin before, or at least slightly before, the deformation of the laterally adjacent staples in the inner row. In other instances, the outer staple rows of the cartridge 240, i.e., the rows furthest away from the channel 243, can lag the inner staple rows, i.e., the rows closest to the channel 243. Stated another way, the deformation of the staples in the inner row can begin before, or at least slightly before, the deformation of the laterally adjacent staples in the outer row. Moreover, while two staples rows are disclosed on each side of the channel 243 defined in the cartridge 240, other embodiments are envisioned in which more than two staple rows, such as three staple rows, for example, are present on each side of the channel 243. In such embodiments, the sled assemblies can be configured to deploy an additional row of staples at the same time as the inner row of staples, at the same time as the outer row of staples, and/or at a time which is staged sequentially with respect to the inner row of staples and the outer row of staples.

As mentioned above, the first sled portion 792 is movable relative to the second sled portion 793 of the sled assembly 790. Turning now to FIGS. 70-72, the sled assembly 790 is movable between an initial, unfired configuration (FIG. 70) and a second, extended configuration (FIGS. 71 and 72). In the initial, unfired configuration of sled assembly 790, referring primarily to FIG. 70, the first sled portion 792 is collapsed within, or retracted relative to, the second sled portion 793. In at least one such instance, the distal end of the first sled portion 792 may not extend beyond the distal end of the second sled portion 793. In other instances, although not illustrated, the distal end of the first sled portion 792 may extend beyond the distal end of the second sled portion 793 when the first sled portion 792 is collapsed within the second portion 793. With further reference to FIG. 70, the reader will further appreciate that the staples 460 are in an unfired position as they have not yet been lifted toward the anvil 124. Upon comparing FIGS. 70 and 71, the reader will notice that the first sled portion 792 has been extended relative to the second sled portion 793. In such circumstances, the distal end of the first sled portion 792 is positioned distally with respect to the distal end of the second sled portion 793. The movement of the first sled portion 792 from its initial, unfired position to its extended position can position the inner ramp portion 791a and/or the outer ramp portion 791b of the first sled portion 792 underneath one or more staples 460. In other configurations, the movement of the first sled portion 792 from its initial, unfired position to its extended position may not position the inner ramp portion 791a and/or the outer ramp portion 791b underneath one or more staples 460. In any event, as illustrated in FIG. 71, the extension of the first sled portion 792 can at least partially lift at least one staple 460 toward the anvil 124 and/or at least partially deform at least one staple 460 against the anvil 124. In certain instances, the extension of the first sled portion 792 can completely lift, or completely deform, at least one staple 460 against the anvil 124. In various circumstances, the second sled portion 793 may not be advanced distally when the first sled portion 792 is moved into its extended position; however, in certain circumstances, at least some distal movement of the second sled portion 793 may occur when the first sled portion 792 is moved into its extended position.

Upon comparing FIGS. 71 and 72, it can be noted that the first sled portion 792 and the second sled portion 793 have been advanced distally to lift staples 460 toward the anvil 124. The first sled portion 792 and the second sled portion 793 can then be advanced to the distal end of the end effector 120 to complete the firing stroke of the end effector 120, which will be discussed in greater detail further below. In any event, the initial progression of the sled assembly 790 during the firing stroke of the end effector 120 is depicted in FIGS. 70-72. FIG. 70 depicts the sled assembly 790 in a retracted, unfired position; FIG. 71 depicts the sled assembly 790 in an extended, partially-fired position; and FIG. 72 depicts the sled assembly 790 in an extended, fired position. As outlined above, the pusher bar, or bars, 159 can be moved distally in order to advance the sled assembly 790 through the progression depicted in FIGS. 70-72. With reference to FIG. 70, a pusher bar 159 is illustrated in an initial, unfired position in which it is in contact with the proximal end of the first sled portion 792. In various embodiments, the pusher bar 159 can include a contact flange 155 extending from the distal end thereof which can engage the first sled portion 792. With further reference to FIG. 70, the pusher bar 159 may not be in contact with the second sled portion 793 when the pusher bar 159 is in its initial, unfired position. As the pusher bar 159 is advanced distally, the pusher bar 159 can move the first sled portion 792 distally until the contact flange 155 comes into contact with the proximal end of the second sled portion 793, as illustrated in FIG. 71. It is this relative motion between the first sled portion 792 and the second sled portion 793 which extends the sled assembly 790 as discussed above. Thereafter, the pusher bar 159 can be advanced distally in order to advance the first sled portion 792 and the second sled portion 793 distally at the same time, as illustrated in FIG. 72.

Figure 77:
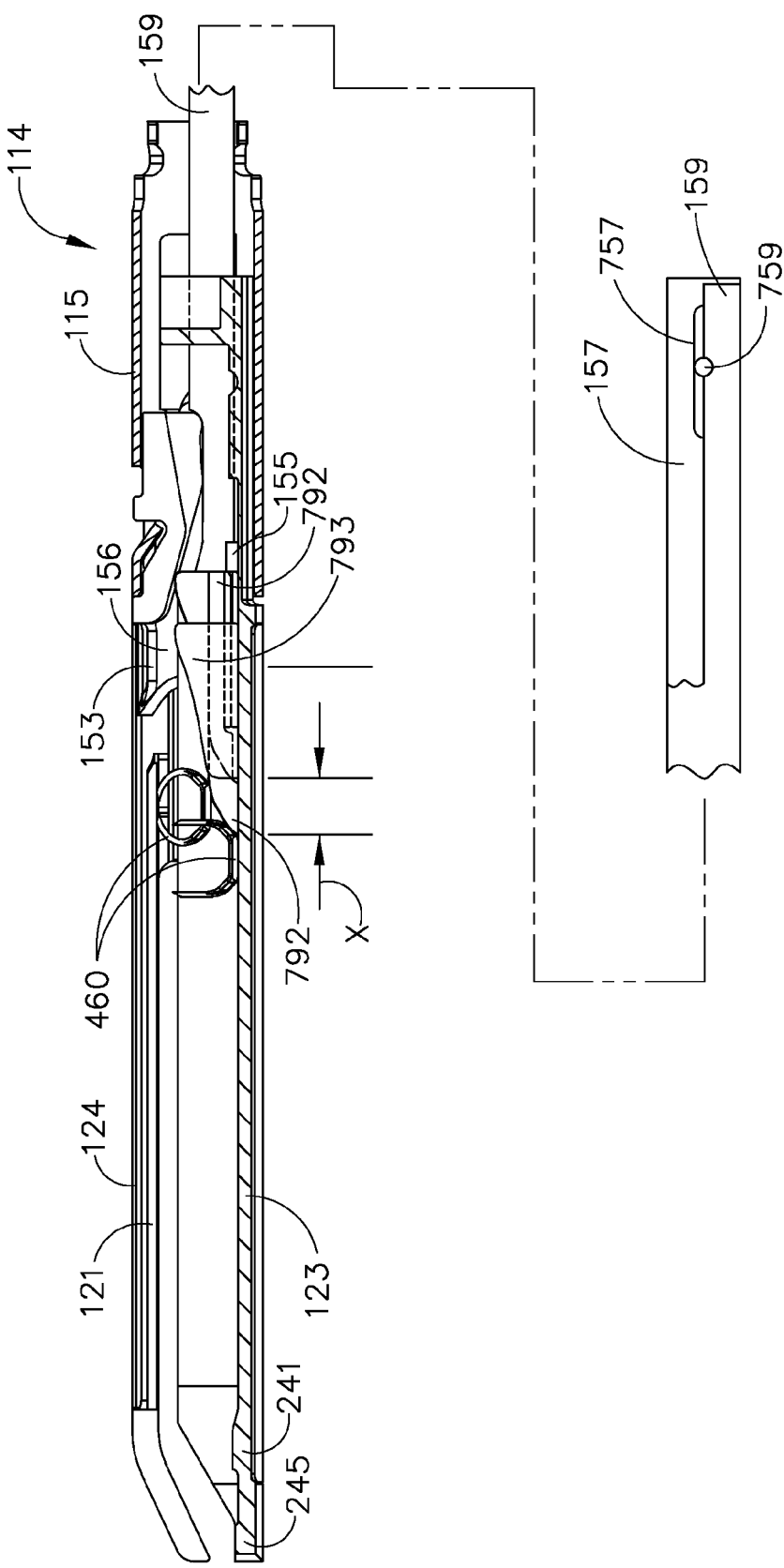
FIG. 77 is a cross-sectional view of the end effector of FIG. 65 illustrating the firing actuator in an extended condition and, in addition, a knife member in an unadvanced position.
Figure 78:
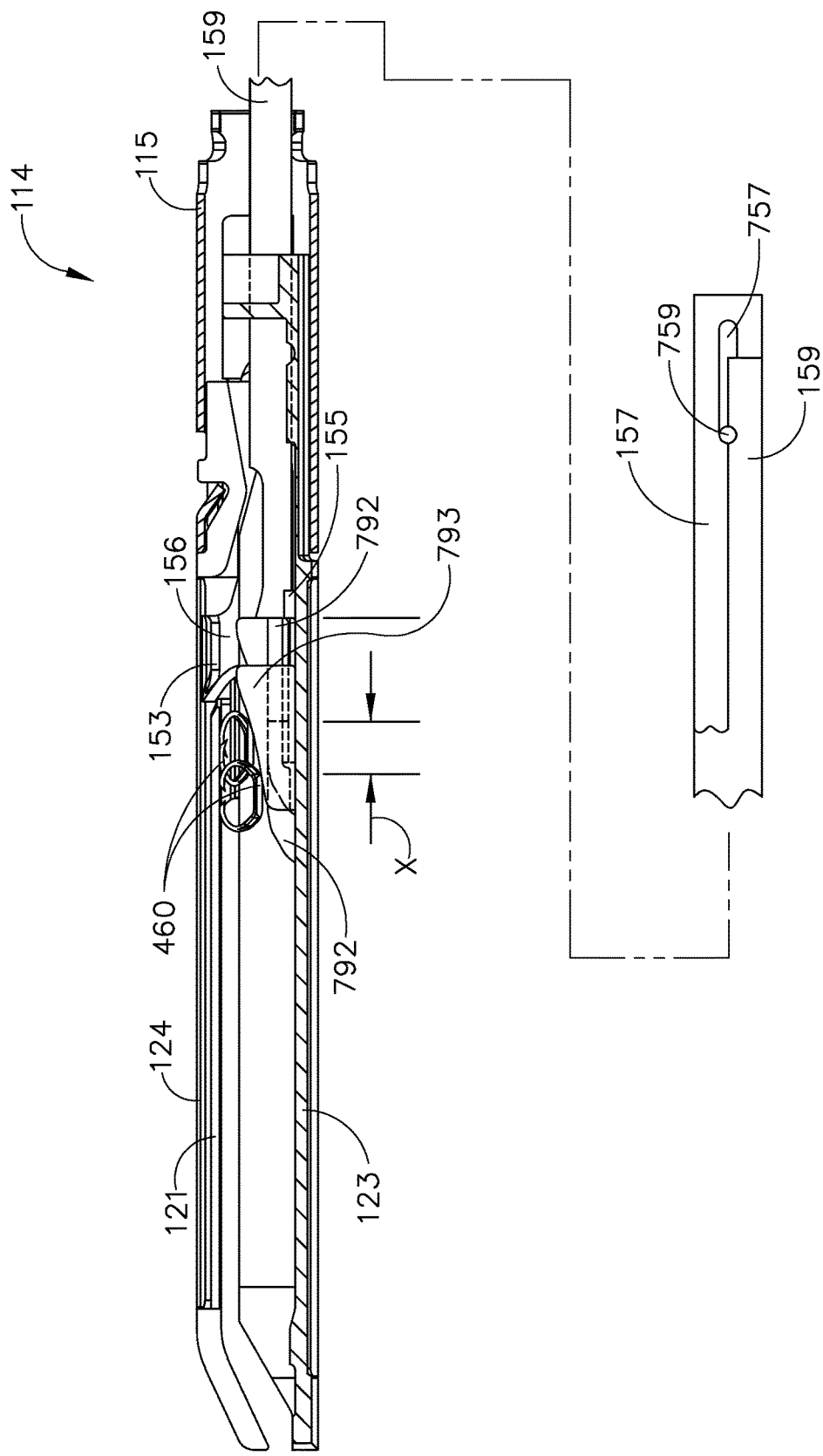
FIG. 78 is a cross-sectional view of the end effector of FIG. 65 illustrating the firing actuator in an advanced, extended condition and the knife member in an advanced position.
Figure 79:
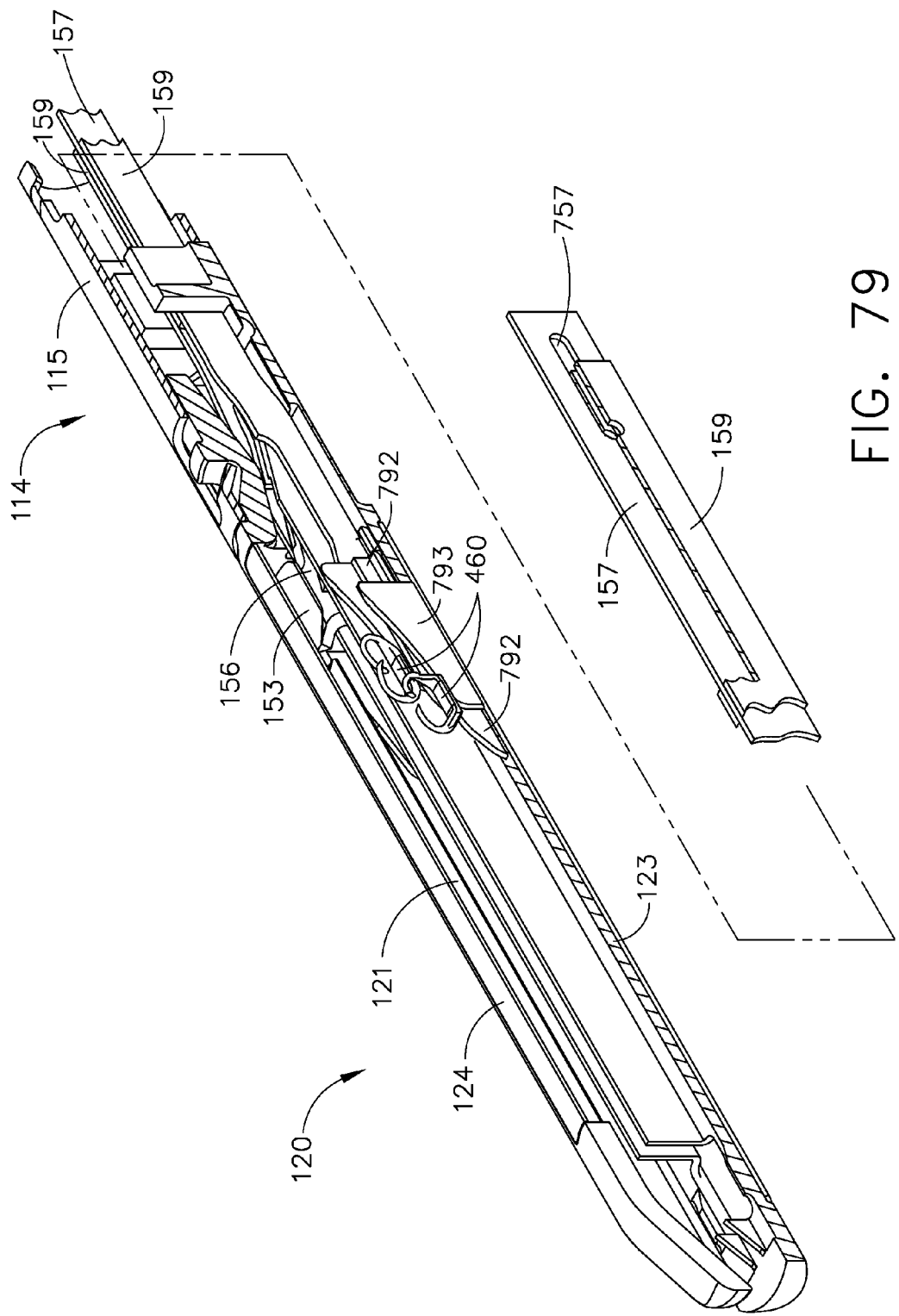
FIG. 79 is a cross-sectional perspective view of the end effector of FIG. 65 illustrated in the configuration depicted in FIG. 78.

As discussed above, the end effector 120 can be configured to staple and transect tissue at the same time. Referring again to FIG. 65, the end effector 120 can include a firing member, or knife bar, 156 comprising a knife edge 158 configured to transect the tissue as the knife bar 156 is advanced distally. Referring again to FIGS. 70 and 71, the initial distal movement of the pusher bar, or bars, 159 may not be transferred to the knife bar 156. Stated another way, the knife bar 156 may remain stationary, or at least substantially stationary, while the sled assembly 790 is moved between its retracted position (FIG. 70) and its extended position (FIG. 71). In such circumstances, relative movement between the pusher bars 159 and the knife bar 156 can occur, at least during the initial portion of the end effector firing stroke. Upon comparing FIGS. 74 and 77, it can be seen that, one, the pusher bars 159 have been advanced distally to extend the sled assembly 790 and, two, the knife bar 156 has not been advanced distally. Particular attention can be paid to the proximal ends of the knife bar 156 and the pusher bars 159. More particularly, the pusher bars 159 can include a drive pin 759 extending therebetween which extends through a drive slot 757 defined in the drive bar 157 extending proximally from the knife bar 156. When the pusher bars 159 are in their proximal unfired position, as illustrated in FIG. 74, the drive pin 759 is positioned in the proximal end of the drive slot 757. When the pusher bars 159 are advanced distally, as illustrated in FIG. 77, the drive pin 759 can slide distally within the drive slot 757 until the drive pin 759 reaches the distal end of the drive slot 757. In such a position, the sled 790 has been fully extended and the knife bar 156 has not yet been advanced distally with the pusher bars 159. Once the drive pin 759 is in contact with the distal end of the drive slot 757, as illustrated in FIGS. 78 and 79, the pusher bars 156 and the knife bar 159 can be advanced distally together.

Further to the above, the knife bar 156 can include flanges 153 and 155 which can be configured to engage the anvil 124 and the staple cartridge channel 123, respectively. When the knife bar 156 is in its proximal, unadvanced position, as illustrated in FIG. 77, the flange 153 can be positioned proximally with respect to a slot 121 defined in the anvil 124. In such a position of the knife bar 156, the flange 155 may or may not be positioned within a slot defined within and/or in the exterior of the cartridge channel 123. As the knife bar 156 is advanced distally, the flange 153 can enter into the anvil slot 121 and the flange 155 can be positioned within the cartridge channel slot. In such circumstances, the knife bar 156 can set the gap, or tissue gap distance, between the anvil 124 and the staple cartridge positioned within the cartridge channel 123. In various circumstances, the knife bar 156 can control the forming height and/or the compression of the tissue within the end effector 120 as the knife bar 156 is advanced distally.

The arrangement described above in which the pusher bars 159 move the sled assembly 790 before the pusher bars 159 advance the knife 158 can be advantageous in many circumstances. For instance, it is often desirable to staple tissue before it is incised and, thus, the formation of the staples leads, or at least sufficiently leads, the transection of the tissue by the knife bar 156. The staggered deployment of the sled 790 and the knife bar 156 can facilitate such a relative progression between the staple formation and the tissue incision. Moreover, the sled 790 can be compactly stored in the end effector 120 in its retracted, unfired configuration in order to permit a shorter proximal-to-distal, or longitudinal, length of the end effector 120. Stated another way, less longitudinal room may be required for a sled assembly that can begin its firing stroke in at least partially collapsed state. Furthermore, owing to the longitudinal extendibility of the sled assembly 790, the staple lifting surfaces of the sled assembly 790 can be longer and can include a shallower, or less aggressive, ramp angle than a unitary sled, for instance. Stated another way, the mechanical advantage of the sled assembly 790 can be improved owing to longer longitudinal lengths available for the ramps of the sled assembly 790.

Figure 82:
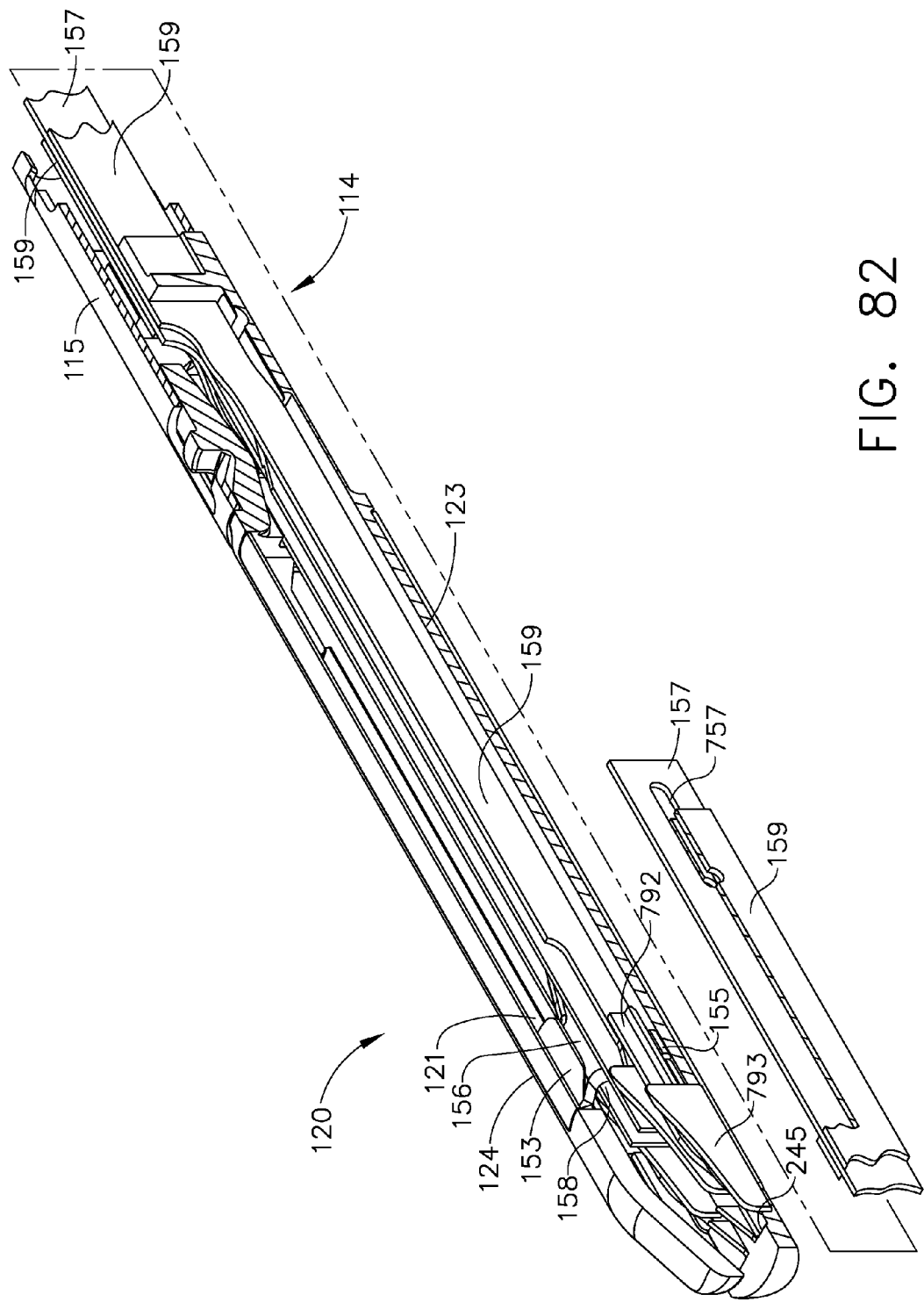
FIG. 82 is a cross-sectional perspective view of the end effector of FIG. 65 illustrated in the configuration depicted in FIG. 80.

Turning now to FIGS. 80-82, the sled assembly 790 and the knife bar 156 can be advanced distally toward the distal end of the end effector 120 to complete the firing stroke of the end effector 120. As the sled 790 approaches the distal end of the end effector 120, in various instances, the first sled portion 792 can contact a distal end 245 of the staple cartridge and retract relative to and/or within the second sled portion 793. More particularly, the distal end 245 can block the distal movement of the first sled portion 792 while the second sled portion 793 is advanced distally relative to the first sled portion 792 in order to complete the firing stroke. In various instances, the second sled portion 793 can be advanced distally until it also contacts the distal end 245 of the staple cartridge while, in other instances, the firing stroke can be completed before the second sled portion 793 contacts the distal end 245. In either event, in embodiments where the distal flanges 155 of the pusher bars 159 push the first sled portion 792 and the second sled portion 793 toward the distal end of the end effector 120, the first sled portion 792 may become disengaged from the pusher bars 159 when the first sled portion 792 reaches the distal end so that that the pusher bars 159 can push the second sled portion 793 relative to the first sled portion 792. In at least one such instance, referring primarily to FIG. 77, the distal end of the staple cartridge can include a boss 241 which can be configured to lift the first sled portion 792 upwardly toward the anvil 124 so that the pusher bars 159 can slide underneath the first sled portion 792. In such circumstances, the first sled portion 792 can be operatively disengaged from the second sled portion 793 and the pusher bars 159. In various instances, the boss 241 can be positioned and arranged such that the first sled portion 792 is lifted upwardly after all of the staples of the staple cartridge have been deployed and/or transferred to the second sled portion 793, as discussed above. Moreover, further to the above, the distal end of the staple cartridge can include a first boss 241 configured to lift a first sled portion 792 and a second boss 241 configured to lift an additional first sled portion 792. In various instances, the bosses 241 can be configured to synchronously lift the first sled portions 792 at the same time. In some instances, the bosses 241 can be configured to lift the first sled portions 792 sequentially.

Figure 86:
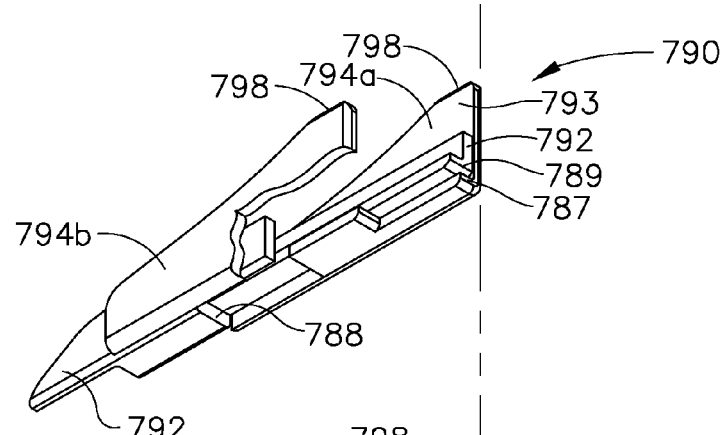
FIG. 86 is a perspective view of the firing member of the end effector of FIG. 65 illustrated in the extended configuration depicted in FIG. 77.
Figure 87:
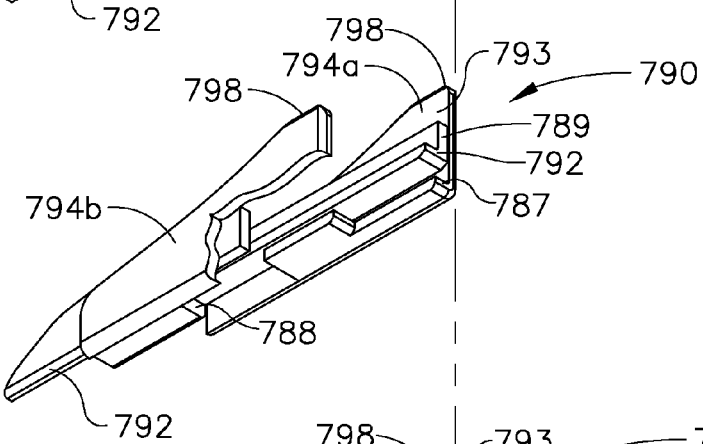
FIG. 87 is a perspective view of the firing member of the end effector of FIG. 65 illustrated in a configuration just prior to the fully-fired configuration depicted in FIG. 80.
Figure 88:
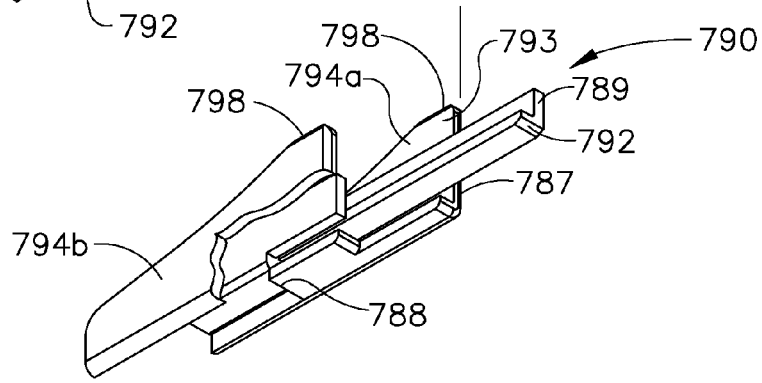
FIG. 88 is a perspective view of the firing member of the end effector of FIG. 65 illustrated in the fully-fired configuration depicted in FIG. 80.

Referring now to FIGS. 85-88, FIG. 85 depicts the sled assembly 790 in its initial, unfired configuration. Further to the above, a pusher bar 159 can contact a proximal end 789 of the first sled portion 792 and push the first sled portion 792 distally until the proximal end 789 of the first sled portion 792 is flush with a proximal end 787 of the second sled portion 793, as illustrated in FIG. 86. At such point, the first sled portion 792 can be fully extended relative to the second sled portion 793. Thereafter, the pusher bar 156 can push on the proximal end 787 and the proximal end 789 simultaneously to advance the sled assembly 790 distally. As also discussed above, referring now to FIG. 87, the first sled portion 792 can be stopped by the distal end 245 of the staple cartridge and lifted upwardly by the boss 241 of the staple cartridge, for instance. At such point, the first sled portion 792 can be elevated relative to the second sled portion 793, and the distal flange 155, such that the second sled portion 793 can be slid relative to, and at least partially underneath, the first sled portion 792, in order to collapse the sled assembly 790, as illustrated in FIG. 88. Upon comparing FIGS. 87 and 88, it can be seen that the second sled portion 793 is moved closer toward ledge 788 defined in the bottom surface of the first sled portion 792 and that the distal end 789 of the first sled portion 792 is no longer aligned with the distal end 787 of the second sled portion 793.

Figure 83:
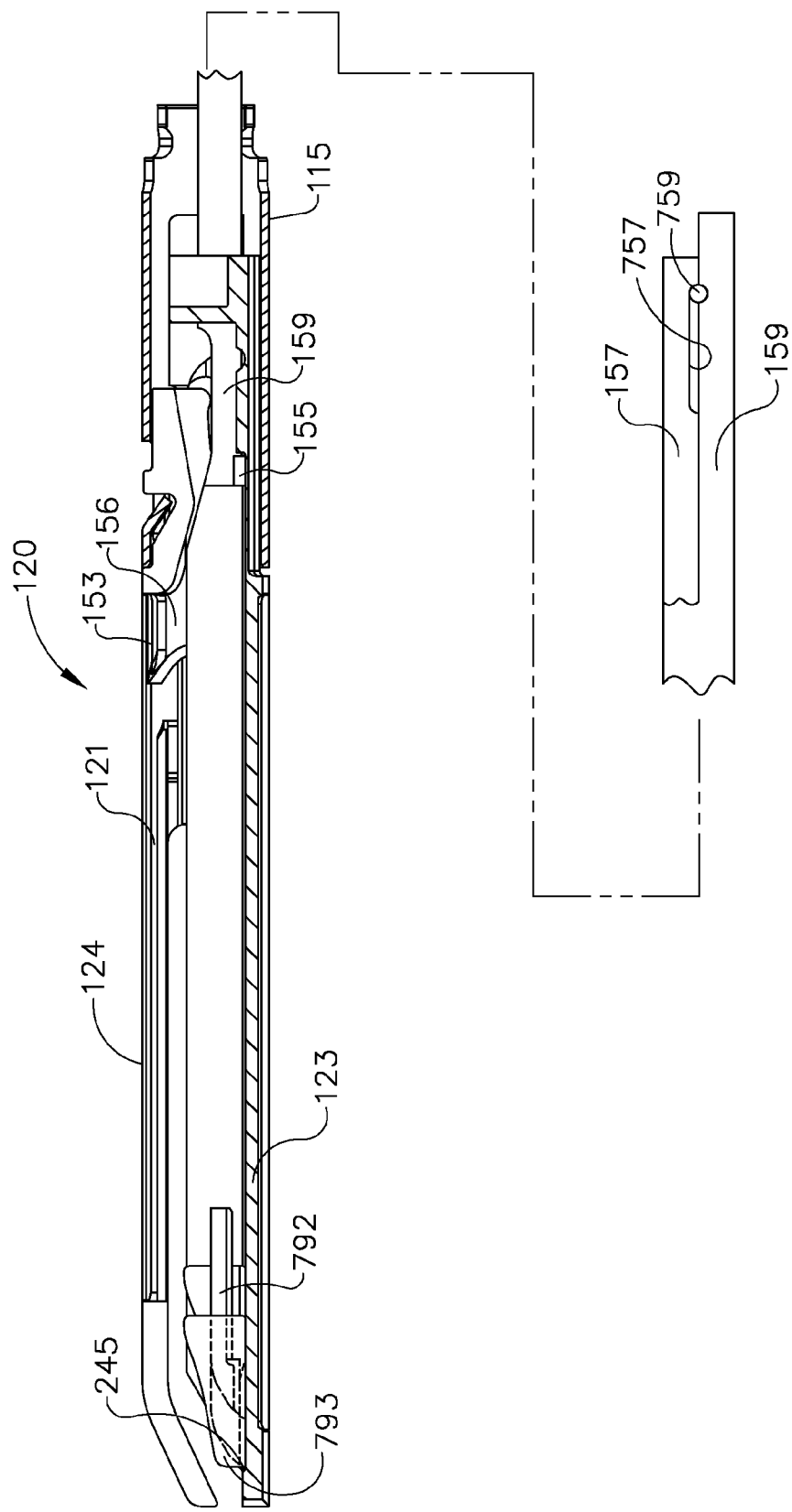
FIG. 83 is a cross-sectional elevational view of the end effector of FIG. 65 illustrating the knife member in a retracted position.
Figure 84:
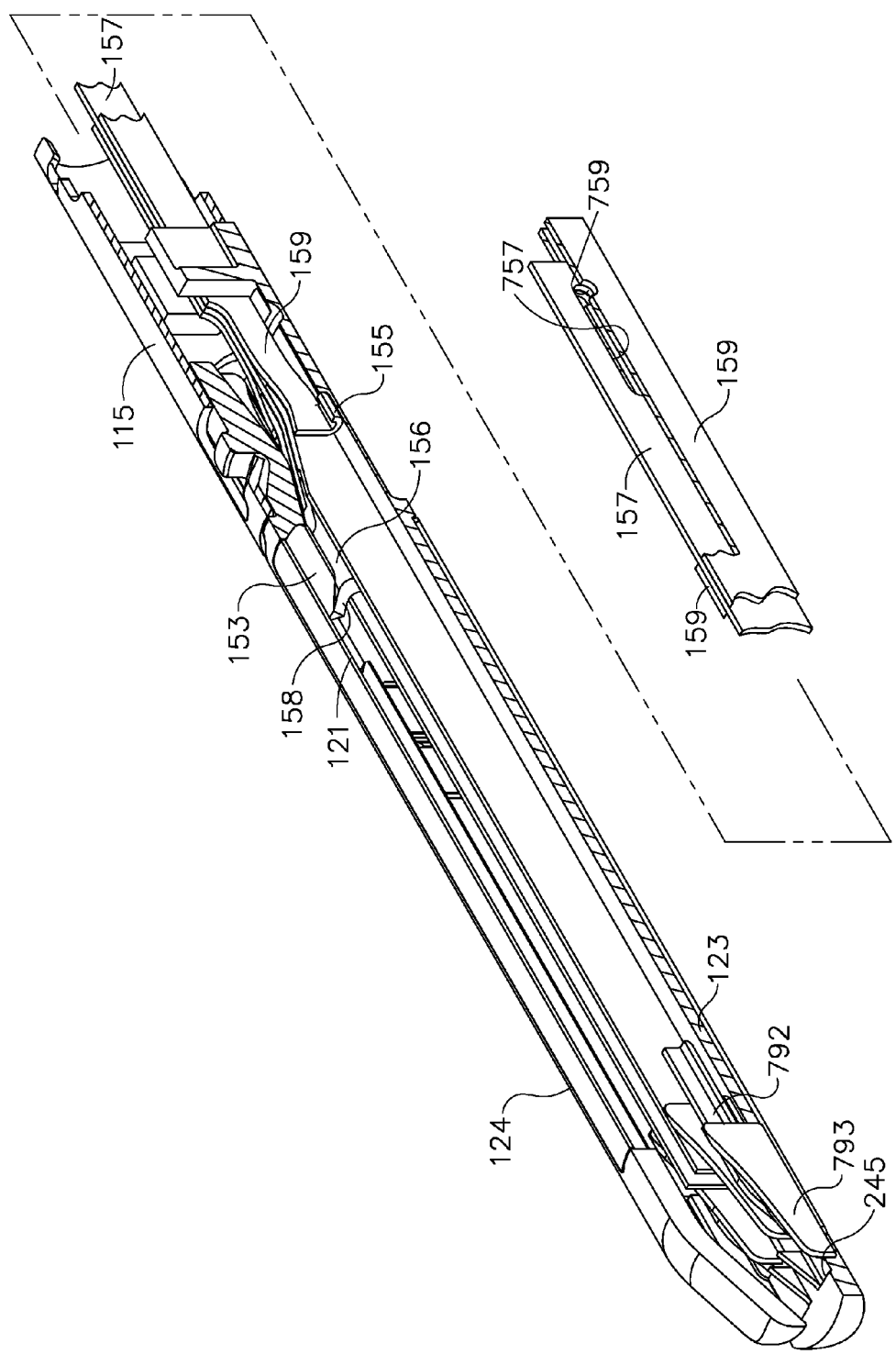
FIG. 84 is a cross-sectional perspective view of the end effector of FIG. 65 illustrated in the configuration depicted in FIG. 83.
Figure 85:
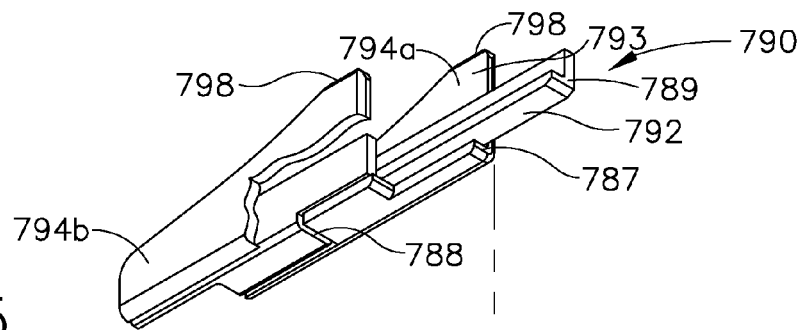
FIG. 85 is a perspective view of the firing member of the end effector of FIG. 65 illustrated in the unextended configuration depicted in FIG. 74.

After the firing stroke has been completed, referring now to FIGS. 83 and 84, the knife bar 156 and the pusher bars 159 can be retracted proximally. In various circumstances, the knife bar 156 can be pulled proximally by the pusher bars 159. More particularly, the pusher bars 159 can be retracted proximally relative to the knife bar 159 until the drive pin 759 contacts the proximal end of the drive slot 759. At such point, the pusher bars 159 can pull the knife bar 156 proximally until the flange 153 of the knife bar 156 is no longer positioned within the slot 121 of the anvil 124. Thereafter, the anvil 124 can be moved into its open position when the closure tube 115 is pulled proximally. In certain instances, the staple cartridge can comprise a replaceable staple cartridge. In such instances, the spent staple cartridge can be removed from the cartridge channel 122 and, if desired, an unspent staple cartridge can be positioned within the cartridge channel 122 so that the surgical instrument can be used once again.

As illustrated in FIGS. 83 and 84, the collapsed sled assembly 790 can be left behind in the distal end of the end effector 120 when the knife bar 156 and the pusher bars 159 are retracted. In the event that the spent staple cartridge is removed from the cartridge channel 122, the collapsed sled assembly 790 can be removed from the end effector 120 with the cartridge. In certain instances, a staple cartridge may not be completely spent before the pusher bars 159 and the knife bar 156 are retracted. In such instances, the sled assembly 790 may only be partially advanced within the staple cartridge and may not be collapsed back into its unextended configuration. When the staple cartridge is then removed from the cartridge channel 123, some of the staples may still be positioned within their staple cavities.

As discussed herein, a firing actuator, or sled, of a staple cartridge and/or stapling instrument can include one or more inclined ramp surfaces configured to lift, or deploy, staples between an unfired position and a fired position. For instance, a sled can include a first inclined ramp surface configured to deploy a first row of staples, a second inclined ramp surface configured to deploy a second row of staples, and so forth. Each inclined ramp surface can comprise a contiguous surface which is configured to engage each staple in the corresponding row of staples and lift the staples until they have been fully deformed against an anvil positioned opposite the staple cartridge. The contiguous surface which defines each inclined ramp surface can include any suitable number of contours such as, for instance, one or more linear surfaces and/or one or more curved surfaces. In various instances, the contiguous surface can directly engage each staple in the corresponding row of staples and can remain continuously engaged with a staple in that row as it moved from its unfired position to its fully-fired position. After a staple has reached its fully-fired position, the inclined ramp surface may become disengaged from that staple. This arrangement can be possible for sleds with relatively movable components, such as sled assembly 790, for instance, and/or sleds that are not comprised of relatively movable components, such as sleds comprised of a unitary piece of material, for example.

Figure 89:
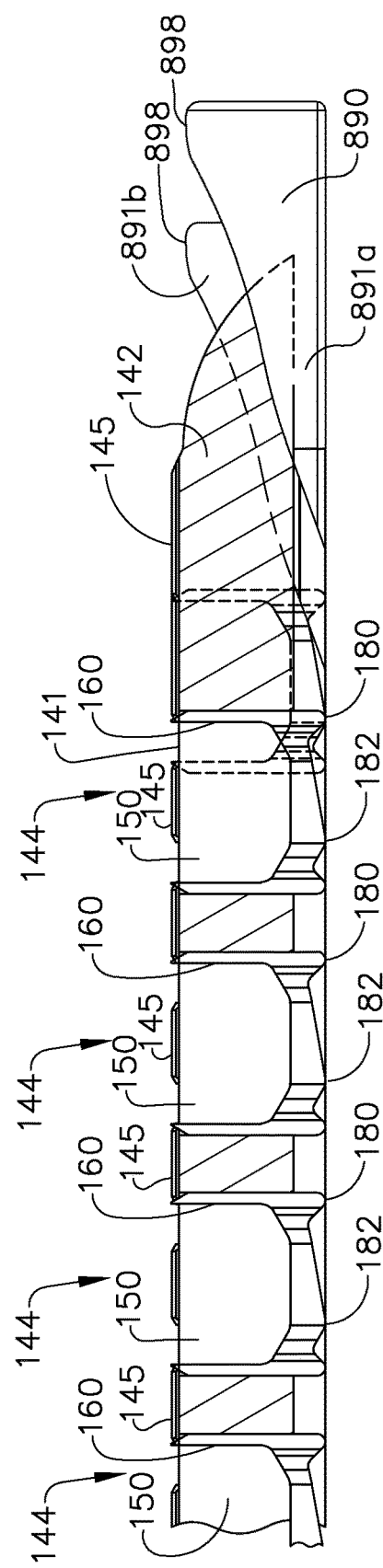
FIG. 89 is a cross-sectional view of an end effector including a firing actuator configured to eject fasteners from a fastener cartridge illustrating the firing actuator in an unfired position.
Figure 90:
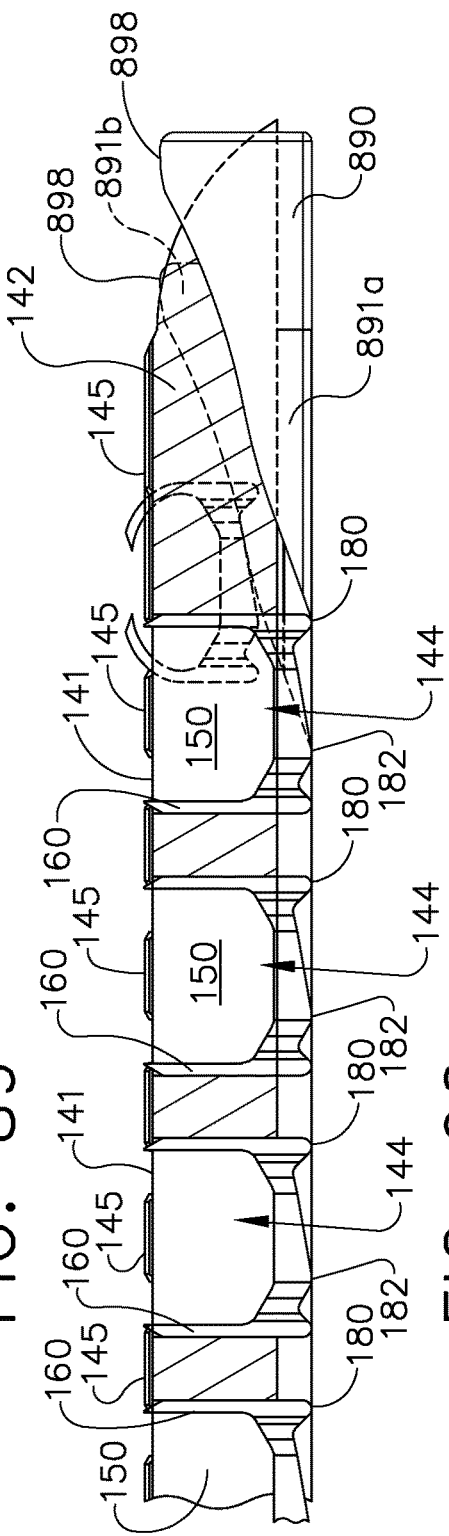
FIG. 90 is a cross-sectional view of the end effector of FIG. 89 illustrating the firing actuator in a partially fired position.
Figure 91:
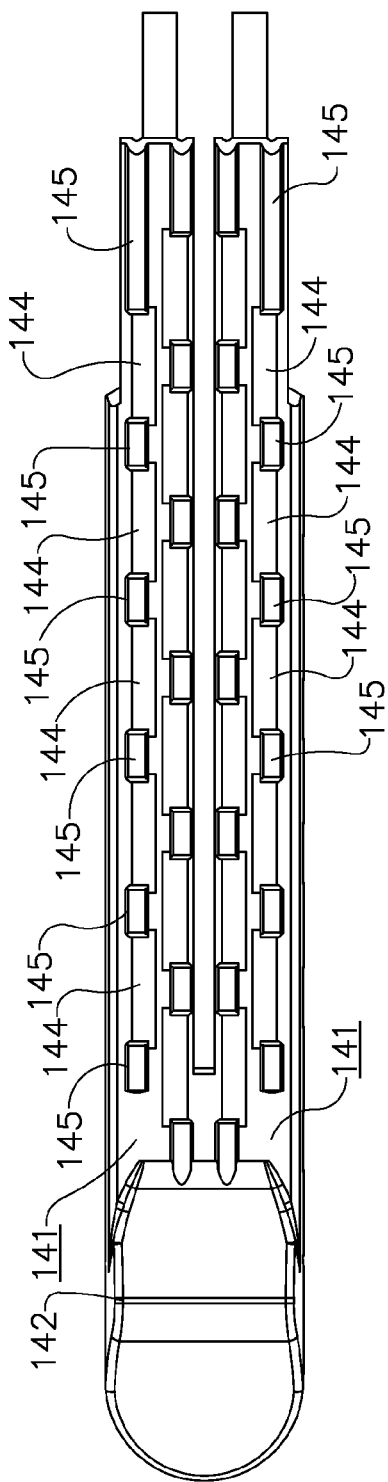
FIG. 91 is a plan view of a staple cartridge body of the end effector of FIG. 89.
Figure 92:
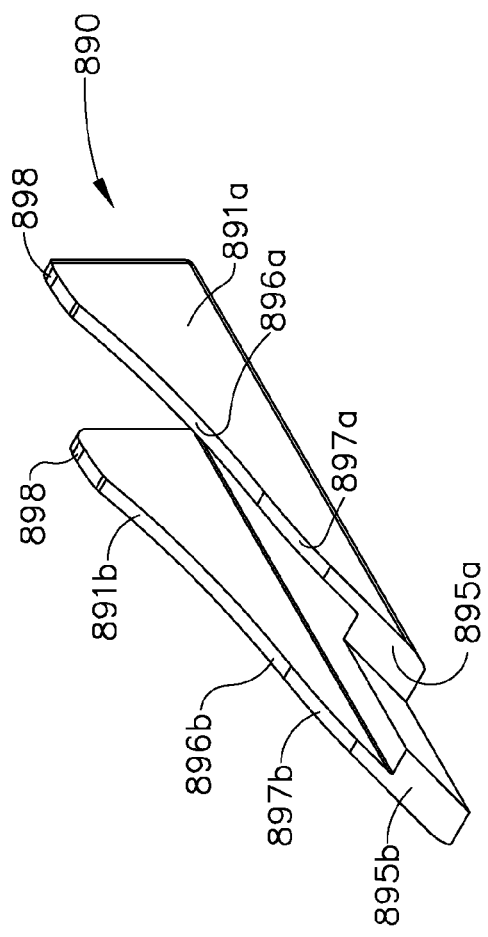
FIG. 92 is a perspective view of a firing actuator for use with the cartridge body of FIG. 91.

In various circumstances, a firing actuator, or sled, can comprise one or more inclined ramp surfaces, wherein each inclined ramped surface is comprised of two or more co-operating drive surfaces. For instance, turning now to FIG. 92, a sled 890 can include a first inclined ramp surface 891a which is comprised of an initial, or first, drive surface 895a and a second, or final, drive surface 896a. The initial drive surface 895a and the final drive surface 896a of the first inclined ramp surface 891a can be configured to co-operatively lift the staples in a first staple row between an unfired position and a fired position. As the sled 890 is moved distally through a staple cartridge, referring to FIGS. 89-92, the initial drive surface 895a can contact a staple 160, for instance, and lift the staple 160 from its unfired position (FIG. 89) to a partially-fired position (FIG. 90). Thereafter, the sled 890 can be advanced distally such that the final drive surface 896a can lift the staple 160 between its partially-fired position and its fully-fired position. In various instances, the initial drive surface 895a can contact the initial drive surfaces 180 of the staples 160 to lift the staples 160 into their partially-fired positions and the final drive surface 896a can contact the second drive surfaces 182 of the staples 160 to lift the staples 160 into their finally-fired positions. In such instances, the staples 160 can be transferred from the initial drive surface 895a to the final drive surface 896a to complete the deployment, or firing, thereof. Referring to FIG. 92, the deployment, or firing, of a staple 160 can be complete once the apex 898 of the first inclined ramp surface 891a has passed under the second drive surface 182 of the staple 160.

Further to the above, referring again to FIG. 92, the initial drive surface 895a and the final drive surface 896a of the first inclined ramp surface 891a can be configured to co-operatively deploy staples within a first row of staples. The sled 890 can include additional inclined ramp surfaces to deploy additional rows of staples. For instance, the sled 890 can include a second inclined ramp surface 891b comprising an initial drive surface 895b and a final drive surface 896b which can be configured to co-operatively deploy staples within a second row of staples. In various instances, the sled 890 can further include any suitable number of inclined ramp surfaces, such as a third inclined ramp surface, similar to first inclined ramp surface 891a, configured to deploy staples within a third row of staples and a fourth inclined ramp surface, similar to second inclined ramp surface 891b, configured to deploy staples within a fourth row of staples, for example. In any event, the drive surfaces of an inclined drive surface, such as drive surfaces 895a, 895b, 896a, and 896b, for example, can include any suitable configuration such as a linear profile and/or a curved profile, for example. With further reference to FIG. 92, the first inclined ramp surface 891a can include a transition drive surface 897a intermediate the initial drive surface 895a and the final drive surface 896a. Similarly, the second inclined ramp surface 891b can include a transition drive surface 897b intermediate the initial drive surface 895b and the final drive surface 896b. In various instances, a transition drive surface can comprise a transition between one drive surface and another drive surface. In some instances, a transition drive surface can comprise a surface which simultaneously drives the initial drive surface 180 and the second drive surface 182 of a staple 160, for example. In various instances, an inclined ramp surface can include any suitable number of drive surfaces.

In various instances, further to the above, the initial drive surface 895a can be positioned laterally with respect to the final drive surface 896a. In certain instances, the initial drive surface 895a and the final drive surface 896a can be connected to one another. In other instances, the initial drive surface 895a and the final drive surface 896a may not be connected to one another. In various circumstances, the initial drive surface 895a can be defined by a first height and the final drive surface 896a can be defined by a second height which is taller than the first height. In certain circumstances, the initial drive surface 895a can be defined along a first longitudinal axis and the final drive surface 896a can be defined along a second longitudinal axis. In certain instances, the first longitudinal axis and the second longitudinal axis can be parallel. In some instances, the initial drive surface 895a can be defined by a first plane and the final drive surface 896a can be defined by a second plane which is parallel to the first plane. In other instances, the first longitudinal axis and the second longitudinal axis can be non-parallel. In some instances, the first longitudinal axis and the second longitudinal axis can extend in directions which converge. In other instances, the first longitudinal axis and the second longitudinal axis can extend in directions which do not converge. In various instances, further to the above, the transition drive surface 897a of the first inclined surface 891a can be defined along an axis which is parallel to the first longitudinal axis and/or the second longitudinal axis. In certain instances, the transition drive surface 897a can be defined along an axis which is not parallel to the first longitudinal axis and/or the second longitudinal axis. In various instances, further to the above, the transition drive surface 897a of the first inclined surface 891a can be defined within a plane which is parallel to the first plane and/or the second plane. In some instances, the transition drive surface 897a can be co-planar with the initial drive surface 895a and/or the final drive surface 896a. In certain instances, the transition drive surface 897a can be defined within a plane which is different than the first plane and/or the second plane. In various instances, further to the above, the transition drive surface 897a can connect the initial drive surface 895a to the final drive surface 896a.

The discussion provided above in connection with inclined ramp surface 891a, initial drive surface 895a, final drive surface 896a, and transition drive surface 897a can be equally applicable to inclined ramp surface 891b, initial drive surface 895b, final drive surface 896b, and transition drive surface 897b, for example.

In various circumstances, further to the above, the first inclined ramp surface 891a can be parallel to the second inclined ramp surface 891b. In other instances, the first inclined ramp surface 891a may not be parallel to the second inclined ramp surface 891b. In various instances, the first inclined ramp surface 891a can be defined by a first height and the second inclined ramp surface 891b can be defined by a second height. In some instances, the first height can be the same as the second height. In such instances, a first row of staples formed by the first inclined ramp surface 891a and a second row of staples formed by the second inclined ramp surface 891b can be formed to the same height. In other instances, the first height can be different that the second height. In such instances, a first row of staples formed by the first inclined ramp surface 891a and a second row of staples formed by the second inclined ramp surface 891b can be formed to different heights. The disclosure of U.S. Pat. No. 8,317,070, entitled SURGICAL STAPLING DEVICES THAT PRODUCE FORMED STAPLES HAVING DIFFERENT LENGTHS, which issued on Nov. 27, 2012, is incorporated by reference in its entirety.

As discussed above, a sled can directly drive and deploy a staple and/or any other suitable fastener stored within a cartridge. Stated another way, the sled can directly contact the staples wherein a driver is not present intermediate the sled and the staples. Such an arrangement is different than arrangements which include a plurality of drivers which support the staples. In such arrangements, the sled engages the drivers to lift the staples. In these arrangements, the drivers are often configured to completely eject the staples from the staple cavities in which they are stored. More particularly, the drivers are configured to lift the staples such that the staples are completely positioned above the top surface, or deck, of the staple cartridge when the staples are in their fully-fired position. In order to completely lift the staples above the deck of the staple cartridge, the drivers may also be at least partially lifted above the deck. Such an arrangement can be characterized as overdriving the staples. Many of the teachings discussed herein can be applied to embodiments including one or more sleds which directly drive staples and, in addition, embodiments including a plurality of drivers which are driven by one or more sleds in order to drive the staples. For instance, sled 890 is discussed in connection with embodiments in which it directly drives staples 160; however, sled 890 could also be used in embodiments which include drivers configured to deploy staples from the staple cavities. In such embodiments, each driver could include a first drive surface similar to first drive surface 180 configured to be engaged by the initial drive surface 895*a*, for instance, and a second drive surface similar to second drive surface 182 configured to be engaged by the final drive surface 896*a*, for instance.

Figures 93, 94:
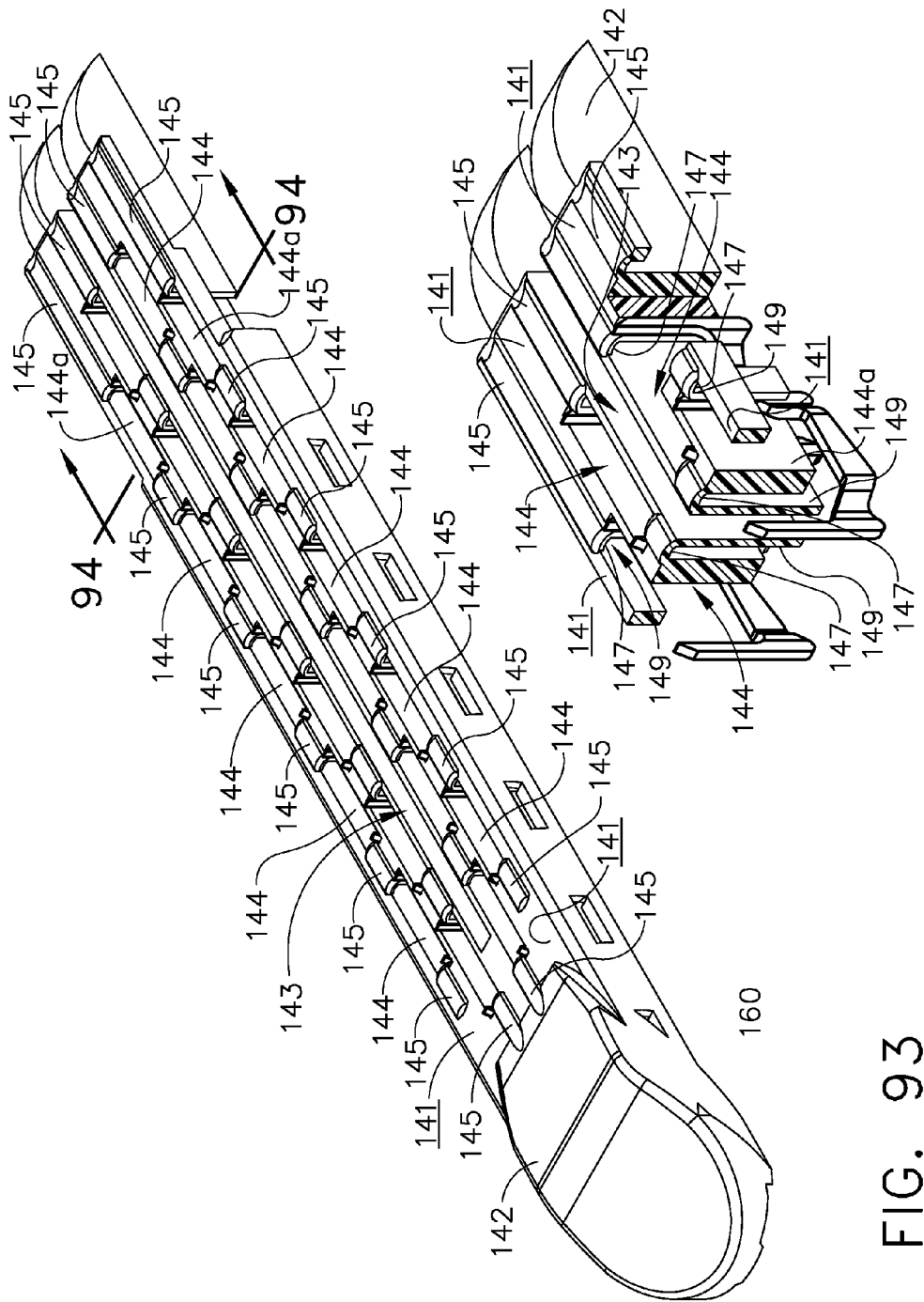
FIG. 93 is a perspective view of the cartridge body of FIG. 91.
FIG. 94 is a cross-sectional view of the cartridge body of FIG. 91 taken along line 94-94 in FIG. 93.

In the embodiments disclosed herein in which the staples are driven directly by the sled, i.e., without the use of drivers, further to the above, the staples can be completely lifted above the deck, or overdriven, by the sled itself. Turning now to FIGS. 91-94, the sled 890 is configured to partially extend above the deck surface 141 of the cartridge 142. More particularly, the apex 898 of the first inclined ramp surface 891*a* and the apex 898 of the second inclined ramp surface 891*b* can extend above the deck surface 141 as the inclined ramp surfaces 891*a* and 891*b* pass through and/or between the cavities 144 to eject the staples 160, for example, from the staple cavities 144. In such circumstances, the sled 890 is configured to partially extend above the staple cavity openings defined in the deck surface 141. In various instances, the cartridge 142 can further comprise a plurality of coverings 145 positioned within and/or aligned with the rows of staple cavities 144. For instance, a covering 145 can be positioned intermediate adjacent staple cavities 144 within a staple cavity row. In certain instances, a covering 145 can be positioned proximally and/or distally with respect to a staple cavity 144. In various instances, referring primarily to FIG. 94, the apexes 898 of the inclined ramp surfaces 891 can pass underneath the coverings 145. In such instances, each covering 145 can include a bottom surface, such as an arched bottom surface 147, for example, configured to permit the inclined ramp surfaces 891 to pass thereunder. With further reference to FIG. 94, the cartridge 142 can include a first longitudinal slot 149 configured to slidably receive the first inclined ramp surface 891*a* therein and a second longitudinal slot 149 configured to receive the second inclined ramp surface 891*b*, for example. In various instances, the cartridge 142 can include a plurality of longitudinal slots 149 configured to receive the inclined ramp surfaces of the sled 890. In certain instances, the longitudinal slots 149 can be defined by the coverings 145 and the staple cavities 144. In some circumstances, each longitudinal slot 149 can correspond to a longitudinal row of staple cavities 144 wherein a longitudinal slot 149 can place the staple cavities 144 within a staple cavity row in communication with each other such that an inclined ramp surface passing through the longitudinal slot 149 can pass through the staple cavities 144 as outlined above.

In various instances, the deck of a cartridge can be configured to directly contact the tissue being fastened and/or support the tissue being fastened. In certain circumstances, a cartridge assembly can include a layer positioned on the deck, such as a tissue thickness compensator, for example, which is disclosed in U.S. patent application Ser. No. 12/894,369, entitled IMPLANTABLE FASTENER CARTRIDGE COMPRISING A SUPPORT RETAINER, now U.S. Patent Application Publication No. 2012/0080344, which was filed on Sep. 30, 2010, U.S. patent application Ser. No. 13/097,856, entitled STAPLE CARTRIDGE COMPRISING STAPLES POSITIONED WITHIN A COMPRESSIBLE PORTION THEREOF, now U.S. Patent Application Publication No. 2012/0080336, which was filed on Apr. 29, 2011, and U.S. patent application Ser. No. 13/242,066, entitled CURVED END EFFECTOR FOR A STAPLING INSTRUMENT, now U.S. Patent Application Publication No. 2012/0080498, which was filed on Sep. 23, 2011. The entire disclosures of U.S. patent application Ser. No. 12/894,369, entitled IMPLANTABLE FASTENER CARTRIDGE COMPRISING A SUPPORT RETAINER, now U.S. Patent Application Publication No. 2012/0080344, which was filed on Sep. 30, 2010, U.S. patent application Ser. No. 13/097,856, entitled STAPLE CARTRIDGE COMPRISING STAPLES POSITIONED WITHIN A COMPRESSIBLE PORTION THEREOF, now U.S. Patent Application Publication No. 2012/0080336, which was filed on Apr. 29, 2011, and U.S. patent application Ser. No. 13/242,066, entitled CURVED END EFFECTOR FOR A STAPLING INSTRUMENT, now U.S. Patent Application Publication No. 2012/0080498, which was filed on Sep. 23, 2011, are incorporated herein by reference. In various instances, referring again to FIG. 93, the deck 141 and the coverings 145 can be configured to directly contact tissue. In such instances, coverings 145 can extend above the deck 141 and, as a result, the deck 141 and the coverings 145 can comprise an uneven support surface. The coverings 145, in various instances, can apply an additional compressive pressure to the tissue positioned directly above and/or adjacent to each longitudinal row of staples. This additional compressive pressure can push fluids present within the tissue away from the staple lines prior to, during, and/or after the staple forming process which, as a result, can promote better staple formation and/or staple retention within the tissue. The coverings 145 can also be configured to grip the tissue positioned between a staple cartridge and an anvil, especially along the staple lines where the staple formation occurs. The coverings can also be configured to support the staples as the staples are being ejected from the staple pockets to provide a localized control over the staple forming process. The entire disclosures of U.S. patent application Ser. No. 12/893,461, entitled STAPLE CARTRIDGE, which was filed on Sep. 29, 2010, now U.S. Pat. No. 8,733,613, and U.S. patent application Ser. No. 13/851,676, entitled TISSUE THICKNESS COMPENSATOR COMPRISING A CUTTING MEMBER PATH, which was filed on Mar. 27, 2013, now U.S. Patent Application Publication No. 2014/0291379, are incorporated by reference herein.

As discussed above, referring primarily to FIGS. 58, 61, and 64, a staple cavity, such as staple cavity 144, for example, can include a first sidewall 150*a* and a second sidewall 150*b* which can be configured to guide a staple, such as a staple 160, for example, as it is lifted between an unfired position and a fired position. In various instances, the sidewalls 150a, 150b can be configured and arranged such that the entirety of the staple 160 is positioned intermediate the sidewalls 150a, 150b when the staple 160 is in its unfired position. In other circumstances, referring primarily to FIGS. 22-31, the sidewalls 150 of the staple cavity 144 may be configured such that less than the entirety of the staple 160 is positioned intermediate the sidewalls 150 when the staple 160 is in its unfired position. For instance, the base 162 of the staples 160 in the outermost rows of staple cavities 144 defined in the cartridge body 142 may be unsupported by at least one of the sidewalls 150 when the staples 160 are in their unfired positions. As the staples 160 are lifted upwardly, however, the bases 162 of the staples 160 may then be supported by both of the sidewalls 150. Turning now to FIGS. 93 and 94, some of the staple cavities 144 of the cartridge 142, such as cavities 144a, for example, may only support both sides of the bases 162 at the end of their lifting motion. In any event, even though the sidewalls of the staple cavities 144 defined in the cartridge body 142 may not entirely support the staples 160 in their unfired positions, the cartridge channel 123 of jaw 122, referring again to FIGS. 3 and 65, may at least partially support the staples 160. Stated another way, the cartridge body 142 and the cartridge channel 123 may co-operate to define the staple cavities 144 in order to support and/or surround the staples 160 throughout the lifting motion of the staples 160. For instance, the cartridge body 142 and the cartridge channel 123 can co-operate to support and/or surround a staple 160 when the staple 160 is in its unlifted position. At some point during the lifting motion of the staple 160, in some circumstances, the cartridge channel 123 may no longer support and/or the staple 160 and, in such circumstances, the cartridge body 142 may entirely support the staple 160 for the remainder of the lifting motion. In at least one embodiment, the cartridge channel 123 and the cartridge body 142 may co-operate to support the staple 160 for half, or approximately half, of the lifting motion. In other embodiments, the cartridge channel 123 and the cartridge body 142 may co-operate to support the staple 160 for less than half or more than half of the lifting motion. In some instances, the cartridge body 142 and the cartridge channel 123 may co-operatively support and/or surround the staple 160 throughout the entire lifting motion of the staple 160.

Various embodiments described herein are described in the context of linear end effectors and/or linear fastener cartridges. Such embodiments, and the teachings thereof, can be applied to non-linear end effectors and/or non-linear fastener cartridges, such as, for example, circular and/or contoured end effectors. For example, various end effectors, including non-linear end effectors, are disclosed in U.S. patent application Ser. No. 13/036,647, filed Feb. 28, 2011, entitled SURGICAL STAPLING INSTRUMENT, now U.S. Pat. No. 8,561,870, which is hereby incorporated by reference in its entirety. Additionally, U.S. patent application Ser. No. 12/893,461, filed Sep. 29, 2012, entitled STAPLE CARTRIDGE, now U.S. Pat. No. 8,733,613, is hereby incorporated by reference in its entirety. U.S. patent application Ser. No. 12/031,873, filed Feb. 15, 2008, entitled END EFFECTORS FOR A SURGICAL CUTTING AND STAPLING INSTRUMENT, now U.S. Pat. No. 7,980,443, is also hereby incorporated by reference in its entirety. The entire disclosure of U.S. Pat. No. 7,845,537, entitled SURGICAL INSTRUMENT HAVING RECORDING CAPABILITIES, which issued on Dec. 7, 2010 is incorporated by reference herein. The entire disclosure of U.S. application Ser. No. 13/118,241, entitled SURGICAL STAPLING INSTRUMENTS WITH ROTATABLE STAPLE DEPLOYMENT ARRANGEMENTS, which was filed on May 27, 2011, now U.S. Pat. No. 9,072,535, is incorporated by reference herein.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:
1. A system, comprising:
  a seamless staple, comprising:
    a first leg
    a second leg, wherein the first leg and the second leg define a first plane; and
    an integral drive surface, wherein the integral drive surface extends along a longitudinal drive axis in a direction parallel to the first plane, and wherein the longitudinal drive axis is laterally offset from the first plane; and a sled comprising an inclined driving surface configured to directly contact the integral drive surface of the seamless staple, wherein the sled is configured to translate along a longitudinal axis to drive the seamless staple along a firing axis, and wherein the firing axis is transverse to the longitudinal axis.

2. The system of claim 1, wherein the integral drive surface further comprises an inclined surface.

3. The system of claim 1, further comprising a plurality of seamless staples, wherein the sled is configured to contact the plurality of seamless staples.

4. The system of claim 1, wherein the sled further comprises a plurality of inclined driving surfaces.

5. The system of claim 4, wherein the seamless staple further comprises a plurality of integral drive surfaces.

6. The system of claim 1, wherein the sled further comprises an overdrive portion.

7. A system, comprising:
a surgical staple, comprising:
a base comprising an inclined drive surface;
a first leg extending from the base; and
a second leg extending from the base, wherein the base, the first leg and the second leg define a seamless unitary piece, wherein the first leg and the second leg define a first plane, wherein the inclined drive surface extends along a longitudinal drive axis in a direction parallel to the first plane, and wherein the longitudinal drive axis is laterally offset from the first plane; and
a sled configured to directly contact the inclined drive surface of the surgical staple, wherein the sled is configured to translate along a longitudinal axis to drive the surgical staple along a firing axis, and wherein the firing axis is transverse to the longitudinal axis.

8. The system of claim 7, wherein the inclined drive surface is positioned intermediate the first leg and the second leg.

9. The system of claim 7, wherein the base further comprises:
a first portion comprising an initial drive surface, wherein the first leg extends from the first portion; and
a second portion, wherein the second leg extends from the second portion.

10. The system of claim 9, wherein the initial drive surface comprises a nub.

11. The system of claim 7, wherein the base is asymmetrical.

12. A system, comprising:
a surgical staple, comprising:
a base;
a first leg extending from the base; and
a second leg extending from the base, wherein the base, the first leg and the second leg define a seamless unitary piece;
wherein said base comprises:
an inclined drive surface;
a first portion comprising an initial drive surface, wherein the inclined drive surface is laterally offset from the initial drive surface, and wherein the first leg extends from the first portion; and
a second portion, wherein the second leg extends from the second portion, and wherein the system further comprises:
a sled configured to directly contact the inclined drive surface of the surgical staple, wherein the sled is configured to translate along a longitudinal axis to drive the surgical staple along a firing axis, and wherein the firing axis is transverse to the longitudinal axis.

13. A system, comprising:
a surgical staple, comprising:
a base comprising a drive surface;
a first leg extending from the base; and
a second leg extending from the base, wherein the first leg and the second leg define a first plane;
wherein a longitudinal axis of the drive surface extends along a portion of the base in a direction parallel to the first plane, and wherein the longitudinal axis of the drive surface is laterally offset from the first plane; and
a sled configured to directly contact the drive surface of the surgical staple.

14. The system of claim 13, wherein the drive surface further comprises a ramp.

15. The system of claim 13, wherein the base further comprises:
a first contour intermediate the drive surface and the first leg; and
a second contour intermediate the drive surface and the second leg.

16. The system of claim 13, wherein the base extends non-linearly between the first leg and the second leg.

17. The system of claim 13, wherein the base further comprises a proximal portion, wherein the first leg extends from the proximal portion, and wherein the proximal portion further comprises an initial drive surface.

18. The system of claim 17, wherein the initial drive surface is positioned in the first plane.

19. The system of claim 17, wherein the proximal portion further comprises a nub.

20. The system of claim 13, wherein the base, the first leg, and the second leg define a unitary piece.

21. A system, comprising:
a surgical staple, comprising:
an integral base comprising a drive surface;
a first deformable leg seamlessly extending from the base; and
a second deformable leg seamlessly extending from the base, wherein the first deformable leg and the second deformable leg define a first plane, wherein the drive surface extends along a longitudinal drive axis in a direction parallel to the first plane, wherein the longitudinal drive axis is laterally offset from the first plane, and wherein the base comprises a variable height intermediate the first deformable leg and the second deformable leg; and
a sled configured to directly drive the surgical staple, wherein the sled is configured to translate along a longitudinal axis to drive the surgical staple along a firing axis, and wherein the firing axis crosses the longitudinal axis.

22. A system, comprising:
a surgical staple, comprising:
a base comprising a drive surface, wherein the drive surface extends along a longitudinal axis;
a first leg extending from the base; and
a second leg extending from the base, wherein the first leg and the second leg define a leg plane, and wherein the leg plane is laterally offset from the longitudinal axis; and
a sled configured to directly contact the drive surface of the surgical staple.

* * * * *